United States Patent [19]

Reitz, Jr. et al.

[11] Patent Number: 5,420,030

[45] Date of Patent: May 30, 1995

[54] MOLECULAR CLONES OF HIV-1 VIRAL STRAINS MN-ST1 AND BA-L AND USES THEREOF

[75] Inventors: Marvin S. Reitz, Jr., Derwood, Md.; Genoveffa Franchini, Washington, D.C.; Phillip D. Markham, Rockville, Md.; Robert C. Gallo, Bethesda, Md.; Franco C. Lori, Bethesda, Md.; Mikulas Popovic, Bethesda, Md.; Suzanne Gartner, N. Potomac, Md.

[73] Assignee: The United States of America as represented by the Department of Health and Human Services, Washington, D.C.

[21] Appl. No.: 22,835

[22] Filed: Feb. 25, 1993

Related U.S. Application Data

[63] Continuation of Ser. No. 599,491, Oct. 17, 1990, abandoned.

[51] Int. Cl.$^6$ ............................................. C12N 7/00
[52] U.S. Cl. ............................ 435/235.1; 435/239; 435/6; 435/69.1; 435/69.3; 536/23.72; 530/324
[58] Field of Search .................... 435/69.1, 69.3, 235.1, 435/239, 6; 530/350, 395, 403, 324; 536/23.72; 935/1

[56] References Cited

PUBLICATIONS

Science, vol. 241, issued 22 Jul. 1988, W. C. Koff et al, Development and Testing of AIDS Vaccines, pp. 426–432.
Nature, vol. 312, issued 20/27 Dec. 1984, P. A. Luciw et al, Molecular cloning of AIDS-associated retrovirus, pp. 760–763.
Science, vol. 226, issued 07 Dec. 1984, G. M. Shaw et al, Molecular Characterization of Human T-Cell Leukemia (Lymphotropic) Virus Type III in the AIDS, pp. 1165–1171.
Nature, vol. 312, issued 20/27 Dec. 1984, M. Alizon et al, "Molecular cloning of lymphadenopathy-associated virus," pp. 757–760.
Journal of Medical Virology, vol. 19, issued 1986, H. R. bsamen–Waigmann et al, "Isolation of Variants of Luymphocytopathic Retroviruses From the Peripheral Blood and Cerebrospinal Fluid of Patients With ARC of AIDS," pp. 335–344.
Nature, vol. 313, issued 24 Jan. 1985, L. Ratner et al, "Complete nucleotide sequence of the AIDS virus, HTLV–III," pp. 277–284.
Cell, vol. 40, issued Jan. 1985, S. Wain–Hobson et al, "Nucleotide Sequence of the AIDS virus, LAV," pp. 9–17.
Science, vol. 227, issued 01 Feb. 1985, R. Sanchez-Pescador et al, "Nucleotide Sequence and Expression of an AIDS–Associated Retrovirus (ARV-2)," pp. 484–492.
Nature, vol. 313, issued 07 Feb. 1985, M. A. Muesing et al, "Nucleic acid structure and expression of the human AIDS/lymphadenopathy retrovirus," pp. 450–458.
Nature, vol. 320, issued 10 Apr. 1986, S.-L. Hu et al, "Expression of AIDS virus envelope gene in recombinant vaccinia viruses," pp. 537–540.
Nature, vol. 320, issued 10 Apr. 1986, S. Chatrabarti et al, "Expression of the HTLV–III envelope gene by a recombinant vaccinia virus," pp. 535–537.

(List continued on next page.)

Primary Examiner—Christine M. Nucker
Assistant Examiner—Jeffrey Stucker
Attorney, Agent, or Firm—Morgan & Finnegan

[57] ABSTRACT

The present invention relates to the HIV-1 strains MN-ST1 and BA-L which are typical United States HIV-1 isotypes. The present invention relates to DNA segments encoding the envelope protein of MN-ST1 or BA-L, to DNA constructs containing such DNA segments and to host cells transformed with such constructs. The viral isolates and envelope proteins of the present invention are of value for use in vaccines and bioassays for the detection of HIV-1 infection in biological samples, such as blood bank samples.

10 Claims, 54 Drawing Sheets

PUBLICATIONS

Bio/Technology, vol. 3 issued Oct. 1985, T. W. Chang et al, "Detection of Antibodies to Human T-Cell Lymphotropic Virus-III (HTLV-III) with an Immunoassay Employing a Recombinant *Escherichia coli*-Derived Viral Antigenic Peptide," pp. 905-909.

Proc. Natl. Acad. Sci. USA, vol. 84, issued Oct. 1987, J. R. Rusche et al, "Humoral immune response to the entire human immunodeficiency virus envelope glycoprotein made in insect cell," pp. 6924-6928.

J. Virology, vol. 63, No. 3, issued Mar. 1989, M. Hadzopoulou-Cladaras et al, "The rev (trs/art) Protein of Human Immunodeficiency Virus Type 1 Affects Viral mRNA and Protein Expression via a cis-Acting Sequence in the env Region," pp. 1265-1274.

J. Virology, vol. 64, No. 9, issued Sep. 1990, P. J. Dillion et al, "Function of the Human Immunodeficiency Virus Types 1 and 2 Rev Proteins Is Dependent on Their Ability To interact with a Structured Region Present in env Gene mRNA," pp. 4428-4437.

Cell, vol. 45, issued 06 Jun. 1986, B. R. Starcich et al, "Identification and Characterization of Conserved and Variable Regions in the Envelope Gene of HTLV-III/LAV, the Retrovirus of AIDS," pp. 637-648.

J. Virology, vol. 61, No. 2, issued Feb. 1986, S. Modrow et al, "Computer-Assisted Analysis of Envelope Protein Sequences of Seven Human Immunodeficiency Virus Isolates: Pediction of Antigenic Epitopes in Conserved and Viriable Regions," pp. 570-578.

Analytical Biochemistry, vol. 151, issued 1985, D. Pauletti et al, "Application of a Modified Computer Algorithm in Determining Potential Antigenic Determinants Associated with the AIDS Virus Glycoprotein," pp. 540-546.

Virology, vol. 164, issued 1988, C. Gurgo et al, "Envelope Sequences of Two New United States HIV-1 Isolates," pp. 531-536.

J. Virology, vol. 64, No. 5, issued May 1990, A. Aldovini et al, "Mutations of RNA and Protein Sequences Involved in Human Immunodeficiency Virus Type 1 Packaging Result in Production of Noninfectious Virus," pp. 1920-1926.

Figure 2A

```
         10         20         30         40         50         60
TGGAAGGGCT AATTCACTCC CAACGAAGAC AAGATATCCT TGATCTGTGG ATCTACCACA 70         80         90        100        110        120
CACAAGGCTA CTTCCCTGAT TAGCAGAACT ACACACCAGG GCCAGGGATC AGATATCCAC 130        140        150        160        170        180
TGACCTTTGG ATGGTGCTAC AAGCTAGTAC CAGTTGAGCC AGAGAAGTTA GAAGAAGCCA 190        200        210        220        230        240
ACAAAGGAGA GAACACCAGC TTGTTACACC CTGTGAGCCT GCATGGAATG GATGACCCGG 250        260        270        280        290        300
AGAGAGAAGT GTTAGAGTGG AGGTTTGACA GCCGCCTAGC ATTTCATCAC ATGGCCCGAG 310        320        330        340        350        360
AGCTGCATCC GGAGTACTTC AAGAACTGCT GACATCGAGC TTGCTACAAG GGACTTTCCG 370        380        390        400        410        420
CTGGGGACTT TCCAGGGAGG CGTGGCCTGG GCGGGACTGG GGAGTGGCGA GCCCTCAGAT 430        440        450        460        470        480
CCTGCATATA AGCAGCTGCT TTTTGCCTGT ACTGGGTCTC TCTGGTTAGA CCAGATCTGA 490        500        510        520        530        540
GCCTGGGAGC TCTCTGGCTA ACTAGGGAAC CCACTGCTTA AGCCTCAATA AAGCTTGCCT 550        560        570        580        590        600
TGAGTGCTTC AAGTAGTGTG TGCCCGTCTG TTATGTGACT CTGGTAGCTA GAGATCCCTC 610        620        630        640        650        660
AGATCCTTTT AGGCAGTGTG GAAAATCTCT AGCAGTGGCG CCCGAACAGG GACTTGAAAG 670        680        690        700        710        720
CGAAAGAAAA ACCAGAGCTC TCTCGACGCA GGACTCGGCT TGCTGAAGCG CGCACGGCAA 730        740        750        760        770        780
GAGGCGAGGG GCGGCGACTG GTGAGTACGC CAAAAATTCT TGACTAGCGG AGGCTAGAAG 790        800        810        820        830        840
GAGAGAGATG GGTGCGAGAG CGTCGGTATT AAGCGGGGGA GAATTAGATC GATGGGAAAA 850        860        870        880        890        900
CATTCGGTTA AGGCCAGGGG GAAAGAAAAA ATATAAATTA AAACATGTAG TATGGGCAAG 910        920        930        940        950        960
CAGGGAGCTA GAACGATTCG CAGTCAATCC TGGCCTGTTA GAAACATCAG AAGGCTGTAG 970        980        990       1000       1010       1020
ACAAATACTG GGACAGCTAC AACCATCCCT TCAGACAGGA TCAGAAGAAC TTAAATCATT 1030       1040       1050       1060       1070       1080
ATATAATACA GTAGCAACCC TCTATTGTGT GCATCAAAAG ATAGAGATAA AAGACACCAA 1090       1100       1110       1120       1130       1140
GGAAGCTTTA GAGAAAATAG AGGAAGAGCA AAACAAAAGT AAGAAAAAAG CACAGCAAGC 1150       1160       1170       1180       1190       1200
AGCAGCTGAC ACAGGAAACA GAGGAAACAG CAGCCAAGTC AGCCAAAATT ACCCCATAGT 1210       1220       1230       1240       1250       1260
GCAGAACATC GAGGGGCAAA TGGTACATCA GGCCATATCA CCTAGAACTT TAAATGCATG
```

Figure 2B

```
      1270       1280       1290       1300       1310       1320
GGTAAAAGTA GTAGAAGAGA AGGCTTTCAG CCCAGAAGTA ATACCCATGT TTTCAGCATT 1330       1340       1350       1360       1370       1380
ATCAGAAGGA GCCACCCCAC AAGATTTAAA CACCATGCTA AACACAGTGG GGGGACATCA 1390       1400       1410       1420       1430       1440
AGCAGCCATG CAAATGTTAA AAGAGACCAT CAATGAGGAA GCTGCAGAAT GGGATAGATT 1450       1460       1470       1480       1490       1500
GCATCCAGTG CATGCAGGGC CTATTACACC AGGCCAGATG AGAGAACCAA GGGGAAGTGA 1510       1520       1530       1540       1550       1560
CATAGCAGGA ACTACTAGTA CCCTTCAGGA ACAAATAGGA TGGATGACAA ATAATCCACC 1570       1580       1590       1600       1610       1620
TATCCCAGTA GGAGAAATCT ATAAAAGATG GATAATCCTG GGATTAAATA AAATAGTAAG 1630       1640       1650       1660       1670       1680
GATGTATAGC CCTTCCAGCA TTCTGGACAT AAGACAAGGA CCAAAGGAAC CCTTTAGAGA 1690       1700       1710       1720       1730       1740
CTATGTAGAC CGGTTCTATA AAACTCTAAG AGCCGAGCAA GCTTCACAGG AGGTAAAAAA 1750       1760       1770       1780       1790       1800
CCGGACGACA GAAACCTTGT TGGTCCAAAA TGCGAACCCA GATTGTAAGA CTATTTTAAA 1810       1820       1830       1840       1850       1860
AGCATTGGGA CCAGCAGCTA CACTAGAAGA AATGATGACA GCATGTCAGG GAGTGGGAGG 1870       1880       1890       1900       1910       1920
ACCTGGTCAT AAAGCAAGAG TTTTGGCGGA AGCGATGAGC CAAGTAACAA ATTCAGCTAC 1930       1940       1950       1960       1970       1980
CATAATGATG CAGAGAGGCA ATTTTAGGAA TCAAAGAAAG ATTATCAAGT GCTTCAATTG 1990       2000       2010       2020       2030       2040
TGGCAAAGAA GGGCACATAG CCAAAAATTG CAGGGCCCCT AGGAAAAGGG GCTGTTGGAA 2050       2060       2070       2080       2090       2100
ATGTGGAAAG GAAGGACACC AAATGAAAGA TTGTACTGAG AGACAGGCTA ATTTTTTAGG 2110       2120       2130       2140       2150       2160
GAAGATCTGG CCTTCCTGCA AGGGAAGGCG GAATTTTCCT CAGAGCAGAA CAGAGCCAAC 2170       2180       2190       2200       2210       2220
AGCCCCACCA GAAGAGAGCT TCAGGTTTGG GGAAGAGACA ACAACTCCCT ATCAGAAGCA 2230       2240       2250       2260       2270       2280
GGAGAAGAAG CAGGAGACGA TAGACAAGGA CCTGTATCCT TTAGCTTCCC TCAAATCACT 2290       2300       2310       2320       2330       2340
CTTTGGCAAC GACCCATTGT CACAATAAAG ATAGGGGGC AACTAAAGGA AGCTCTATTA 2350       2360       2370       2380       2390       2400
GATACAGGAG CAGATGATAC AGTATTAGGA GAAATGAATT TGCCAAGAAG ATGGAAACCA 2410       2420       2430       2440       2450       2460
AAAATGATAG GGGGAATTGG AGGTTTTATC AAAGTAAGAC AGTATGATCA GATAACCATA 2470       2480       2490       2500       2510       2520
GGAATCTGTG GACATAAAGC TATAGGTACA GTATTAGTAG GACCTACACC TGTCAACATA
```

Figure 2C

```
         2530       2540       2550       2560       2570       2580
    ATTGGAAGAA ATCTGTTGAC TCAGCTTGGG TGCACTTTAA ATTTTCCCAT TAGTCCTATT 2590       2600       2610       2620       2630       2640
    GAAACTGTAC CAGTAAAATT AAAGCCAGGA ATGGATGGCC CAAAAGTTAA ACAATGGCCA 2650       2660       2670       2680       2690       2700
    TTGACAGAAG AAAAAATAAA AGCATTAATA GAAATTTGTA CAGAAATGGA AAAGGAAGGG 2710       2720       2730       2740       2750       2760
    AAAATTTCAA AAATTGGGCC TGAAAATCCA TACAATACTC CAGTATTTGC CATAAAGAAA 2770       2780       2790       2800       2810       2820
    AAAGACAGTA CTAAATGGAG AAAATTAGTA GATTTCAGAG AACTTAATAA GAAAACTCAA 2830       2840       2850       2860       2870       2880
    GACTTCTGGG AAGTTCAATT AGGAATACCA CATCCTGCAG GGTTAAAAAA GAAAAAATCA 2890       2900       2910       2920       2930       2940
    GTAACAGTAC TGGATGTGGG TGATGCATAT TTTTCAGTTC CCTTAGATAA AGACTTCAGG 2950       2960       2970       2980       2990       3000
    AAGTATACTG CATTTACCAT ACCTAGTATA AACAATGAAA CACCAGGGAT TAGATATCAG 3010       3020       3030       3040       3050       3060
    TACAATGTGC TTCCACAGGG ATGGAAAGGA TCACCAGCAA TATTCCAAAG TAGCATGACA 3070       3080       3090       3100       3110       3120
    AAAATCTTAG AGCCTTTTAG AAAACAAAAT CCAGACATAG TTATCTATCA ATACATGGAT 3130       3140       3150       3160       3170       3180
    GATTTGTATG TAGGATCTGA CTTAGAAATA GGGCAGCATA GAGCAAAAAT AGAGGAACTG 3190       3200       3210       3220       3230       3240
    AGACGACATC TGTTGAGGTG GGGATTTACC ACACCAGACA AAAAACATCA GAAAGAACCT 3250       3260       3270       3280       3290       3300
    CCATTCCTTT GGATGGGTTA TGAACTCCAT CCTGATAAAT GGACAGTACA GCCTATAGTG 3310       3320       3330       3340       3350       3360
    CTACCAGAAA AAGACAGCTG GACTGTCAAT GACATACAGA AGTTAGTGGG AAAATTGAAT 3370       3380       3390       3400       3410       3420
    TGGGCAAGTC AGATTTACGC AGGGATTAAA GTAAAGCAAT TATGTAAACT CCTTAGAGGA 3430       3440       3450       3460       3470       3480
    ACCAAAGCAC TAACAGAAGT AATACCACTA ACAGAAGAAG CAGAGCTAGA ACTGGCAGAA 3490       3500       3510       3520       3530       3540
    AACAGGGAAA TTCTAAAAGA ACCAGTACAT GGAGTGTATT ATGACCCATC AAAAGACTTA 3550       3560       3570       3580       3590       3600
    ATAGCAGAAG TACAGAAGCA GGGGCAAGGC CAATGGACAT ATCAAATTTA TCAAGAGCCA 3610       3620       3630       3640       3650       3660
    TTTAAAAATC TGAAAACAGG CAAATATGCA AGAATGAGGG GTGCCCACAC TAATGATGTA 3670       3680       3690       3700       3710       3720
    AAACAATTAA CAGAGGCAGT GCAAAAAATA GCCACAGAAA GCATAGTAAT ATGGGGAAAG 3730       3740       3750       3760       3770       3780
    ACTCCTAAAT TTAGACTACC CATACAAAAA GAAACATGGG AAACATGGTG GACAGAGTAT
```

Figure 2D

```
        3790       3800       3810       3820       3830       3840
   ACGTAAGCCA CCTGGATTCC TGAGTGGGAG GTTGTCAATA CCCCTCCCTT AGTGAAATTA 3850       3860       3870       3880       3890       3900
   TGGTACCAGT TAGAGAAAGA ACCCATAGTA GGTGCAGAAA CTTTCTATGT AGATGGGGCA 3910       3920       3930       3940       3950       3960
   GCTAACAGGG AGACTAAAAA AGGAAAAGCA GGATATGTTA CTAACAGAGG AAGACAAAAG 3970       3980       3990       4000       4010       4020
   GTTGTCTCCC TAACTGACAC AACAAATCAG AAGACTGAGT TACAAGCAAT TCATCTAGCT 4030       4040       4050       4060       4070       4080
   TTGCAAGATT CAGGGTTAGA AGTAAACATA GTAACAGACT CACAATATGC ATTAGGAATC 4090       4100       4110       4120       4130       4140
   ATTCAAGCAC AACCAGATAA AAGTGAATCA GAGTTAGTCA GTCAAATAAT AGAGCAGTTA 4150       4160       4170       4180       4190       4200
   ATAAAAAAGG AAAAGGTCTA TCTGGCATGG GTACCAGCAC ACAAAGGAAT TGGAGGAAAT 4210       4220       4230       4240       4250       4260
   GAACAAGTAG ATAAATTAGT CAGTGCTGGA ATCAGGAAAG TACTATTTTT AGATGGAATA 4270       4280       4290       4300       4310       4320
   GATAAGGCCC AAGAAGACCA TGAGAAATAT CACAGTAATT GGAGAGCAAT GGCTAGTGAC 4330       4340       4350       4360       4370       4380
   TTTAACCTAC CACCTATAGT AGCAAAAGAA ATAGTAGCCA GCTGTGATAA ATGTCAGCTA 4390       4400       4410       4420       4430       4440
   AAAGGAGAAG CCATGCATGG ACAAGTAGAC TGTAGTCCAG GAATATGGCA ACTAGATTGT 4450       4460       4470       4480       4490       4500
   ACACATTTAG AAGGAAAAGT TATCCTGGTA GCAGTTCATG TAGCCAGTGG ATACATAGAA 4510       4520       4530       4540       4550       4560
   GCAGAAGTTA TTCCAGCAGA GACAGGGCAG GAGACAGCAT ACTTTCTCTT AAAATTAGCA 4570       4580       4590       4600       4610       4620
   GGAAGATGGC CAGTAAAAAC AATACATACA GACAATGGCC CCAATTTCAC CAGTACTACG 4630       4640       4650       4660       4670       4680
   GTTAAGGCCG CCTGTTGGTG GACGGGAATC AAGCAGGAAT TTGGCATTCC CTACAATCCC 4690       4700       4710       4720       4730       4740
   CAAAGTCAAG GAGTAATAGA ATCTATGAAT AAAGAATTAA AGAAAATTAT AGGACAGGTA 4750       4760       4770       4780       4790       4800
   AGAGATCAGG CTGAACATCT TAAGAGAGCA GTACAAATGG CAGTATTCAT CCACAATTTT 4810       4820       4830       4840       4850       4860
   AAAAGAAAAG GGGGGATTGG GGGTACAGT GCAGGGGAAA GAATAGTAGG CATAATAGCA 4870       4880       4890       4900       4910       4920
   ACAGACATAC AAACTAAAGA ACTACAAAAA CAAATTACAA AAATTCAAAA TTTTCGGGTT 4930       4940       4950       4960       4970       4980
   TATTACAGGG ACAGCAGAGA TCCACTTTGG AAAGGACCAG CAAAGCTTCT CTGGAAAGGT 4990       5000       5010       5020       5030       5040
   GAAGGGGCAG TAGTAATACA AGATAATAAT GACATAAAAG TAGTGCCAAG AAGAAAAGCA
```

Figure 2E

```
        5050       5060       5070       5080       5090       5100
   AAGGTCATTA GGGATTATGG AAAACAGACG GCAGGTGATG ATTGTGTGGC AAGCAGACAG 5110       5120       5130       5140       5150       5160
   GATGAGGATT AGAACATGGA AAAGTTTAGT AAAACACCAT ATGTATATTT CAAAGAAAGC 5170       5180       5190       5200       5210       5220
   TAAAGGACGG TTTTATAGAC ATCACTATGA AAGCACTCAT CCAAGAATAA GTTCAGAAGT 5230       5240       5250       5260       5270       5280
   ACACATCCCA CTAGGGGATG CTAGATTGGT AATAACAACA TATTGGGGTC TGCATACAGG 5290       5300       5310       5320       5330       5340
   AGAAAGAGAC TGGCATTTAG GTCAGGGAGT CTCCATAGAA TGGAGGAAAA AGAGATATAG 5350       5360       5370       5380       5390       5400
   CACACAAGTA GACCCTGACC TAGCAGACCA CCTAATTCAT CTGCATTACT TTGATTGTTT 5410       5420       5430       5440       5450       5460
   TTCAGACTCT GCCATAAGAA AGGCCATATT AGGACATAGA GTTAGTCCTA TTTGTGAATT 5470       5480       5490       5500       5510       5520
   TCAAGCAGGA CATAACAAGG TAGGACCTCT ACAGTACTTG GCACTAACAG CATTAATAAC 5530       5540       5550       5560       5570       5580
   ACCAAAAAAG ATAAAGCCAC CTTTGCCTAG TGTTAAGAAA CTGACAGAGG ATAGATGGAA 5590       5600       5610       5620       5630       5640
   CAAGCCCCAG AAGACCAAGG GCCACAGAGG GAGCCATACA ATCAATGGGC ACTAGAGCTT 5650       5660       5670       5680       5690       5700
   TTAGAGGAGC TTAAGAATGA AGCTGTTAGA CATTTTCCTA GGATATGGCT CCATGGCTTA 5710       5720       5730       5740       5750       5760
   GGGCAACATA TCTATGAAAC TTATGGGGAT ACTTGGGCAG GAGTGGAAGC CATAATAAGA 5770       5780       5790       5800       5810       5820
   ATTCTACAAC AACTGCTGTT TATTCATTTC AGAATTGGGT GTCGACATAG CAGAATAGGC 5830       5840       5850       5860       5870       5880
   ATTATTCGAC AGAGGAGAGC AAGAAATGGA GCCAGTAGAT CCTAGACTAG AGCCCTGGAA 5890       5900       5910       5920       5930       5940
   GCATCCAGGA AGTCAGCCTA AGACTGCTTG TACCACTTGC TATTGTAAAA AGTGTTGCTT 5950       5960       5970       5980       5990       6000
   TCATTGCCAA GTTTGTTTCA CAAAAAAAGC CTTAGGCATC TCCTATGGCA GGAAGAAGCG 6010       6020       6030       6040       6050       6060
   GAGACAGCGA CGAAGAGCTC CTGAAGACAG TCAGACTCAT CAAGTTTCTC TACCAAAGCA 6070       6080       6090       6100       6110       6120
   GTAAGTAGTA CATGTAATGC AACCTTTAGT AATAGCAGCA ATAGTAGCAT TAGTAGTAGC 6130       6140       6150       6160       6170       6180
   AGGAATAATA GCAATAGTTG TGTGATCCAT AGTATTCATA GAATATAGGA AAATAAGAAG 6190       6200       6210       6220       6230       6240
   ACAAAGAAAA ATAGACAGGT TAATTGATAG AATAAGCGAA AGAGCAGAAG ACAGTGGCAA 6250       6260       6270       6280       6290       6300
   TGAGAGTGAA GGGGATCAGG AGGAATTATC AGCACTGGTG GGGATGGGGC ACGATGCTCC
```

Figure 2F

```
           6310       6320       6330       6340       6350       6360
      TTGGGTTATT AATGATCTGT AGTGCTACAG AAAAATTGTG GGTCACAGTC TATTATGGGG 6370       6380       6390       6400       6410       6420
      TACCTGTGTG GAAAGAAGCA ACCACCACTC TATTTTGTGC ATCAGATGCT AAAGCATATG 6430       6440       6450       6460       6470       6480
      ATACAGAGGT ACATAATGTT TGGGCCACAC AAGCCTGTGT ACCCACAGAC CCCAACCCAC 6490       6500       6510       6520       6530       6540
      AAGAAGTAGA ATTGGTAAAT GTGACAGAAA ATTTTAACAT GTGGAAAAAT AACATGGTAG 6550       6560       6570       6580       6590       6600
      AACAGATGCA TGAGGATATA ATCAGTTTAT GGGATCAAAG CCTAAAGCCA TGTGTAAAAT 6610       6620       6630       6640       6650       6660
      TAACCCCACT CTGTGTTACT TTAAATTGCA CTGATTTGAG GAATACTACT AATACCAATA 6670       6680       6690       6700       6710       6720
      ATAGTACTGC TAATAACAAT AGTAATAGCG AGGGAACAAT AAAGGGAGGA GAAATGAAAA 6730       6740       6750       6760       6770       6780
      ACTGCTCTTT CAATATCACC ACAAGCATAA GAGATAAGAT GCAGAAAGAA TATGCACTTC 6790       6800       6810       6820       6830       6840
      TTTATAAACT TGATATAGTA TCAATAGATA ATGATAGTAC CAGCTATAGG TTGATAAGTT 6850       6860       6870       6880       6890       6900
      GTAATACCTC AGTCATTACA CAAGCTTGTC CAAAGATATC CTTTGAGCCA ATTCCCATAC 6910       6920       6930       6940       6950       6960
      ACTATTGTGC CCCGGCTGGT TTTGCGATTC TAAAATGTAA CGATAAAAAG TTCAGTGGAA 6970       6980       6990       7000       7010       7020
      AAGGATCATG TAAAAATGTC AGCACAGTAC AATGTACACA TGGAATTAGG CCAGTAGTAT 7030       7040       7050       7060       7070       7080
      CAACTCAACT GCTGTTAAAT GGCAGTCTAG CAGAAGAAGA GGTAGTAATT AGATCTGAGA 7090       7100       7110       7120       7130       7140
      ATTTCACTGA TAATGCTAAA ACCATCATAG TACATCTGAA TGAATCTGTA CAAATTAATT 7150       7160       7170       7180       7190       7200
      GTACAAGACC CAACTACAAT AAAAGAAAAA GGATACATAT AGGACCAGGG AGAGCATTTT 7210       7220       7230       7240       7250       7260
      ATACAACAAA AAATATAATA GGAACTATAA GACAAGCACA TTGTAACATT AGTAGAGCAA 7270       7280       7290       7300       7310       7320
      AATGGAATGA CACTTTAAGA CAGATAGTTA GCAAATTAAA AGAACAATTT AAGAATAAAA 7330       7340       7350       7360       7370       7380
      CAATAGTCTT TAATCAATCC TCAGGAGGGG ACCCAGAAAT TGTAATGCAC AGTTTTAATT 7390       7400       7410       7420       7430       7440
      GTGGAGGGGA ATTTTCTAC TGTAATACAT CACCACTGTT TAATAGTACT TGGAATGGTA 7450       7460       7470       7480       7490       7500
      ATAATACTTG GAATAATACT ACAGGGTCAA ATAACAATAT CACACTTCAA TGCAAAATAA 7510       7520       7530       7540       7550       7560
      AACAAATTAT AAACATGTGG CAGGAAGTAG GAAAAGCAAT GTATGCCCCT CCCATTGAAG
```

Figure 2G

```
          7570       7580       7590       7600       7610       7620
     GACAAATTAG ATGTTCATCA AATATTACAG GGCTACTATT AACAAGAGAT GGTGGTAAGG 7630       7640       7650       7660       7670       7680
     ACACGGACAC GAACGACACC GAGATCTTCA GACCTGGAGG AGGAGATATG AGGGACAATT 7690       7700       7710       7720       7730       7740
     GGAGAAGTGA ATTATATAAA TATAAAGTAG TAACAATTGA ACCATTAGGA GTAGCACCCA 7750       7760       7770       7780       7790       7800
     CCAAGGCAAA GAGAAGAGTG GTGCAGAGAG AAAAAAGAGC AGCGATAGGA GCTCTGTTCC 7810       7820       7830       7840       7850       7860
     TTGGGTTCTT AGGAGCAGCA GGAAGCACTA TGGGCGCAGC GTCAGTGACG CTGACGGTAC 7870       7880       7890       7900       7910       7920
     AGGCCAGACT ATTATTGTCT GGTATAGTGC AACAGCAGAA CAATTTGCTG AGGGCCATTG 7930       7940       7950       7960       7970       7980
     AGGCGCAACA GCATATGTTG CAACTCACAG TCTGGGGCAT CAAGCAGCTC CAGGCAAGAG 7990       8000       8010       8020       8030       8040
     TCCTGGCTGT GGAAAGATAC CTAAAGGATC AACAGCTCCT GGGGTTTTGG GGTTGCTCTG 8050       8060       8070       8080       8090       8100
     GAAAACTCAT TTGCACCACT ACTGTGCCTT GGAATGCTAG TTGGAGTAAT AAATCTCTGG 8110       8120       8130       8140       8150       8160
     ATGATATTTG GAATAACATG ACCTGGATGC AGTGGGAAAG AGAAATTGAC AATTACACAA 8170       8180       8190       8200       8210       8220
     GCTTAATATA CTCATTACTA GAAAAATCGC AAACCCAACA AGAAAAGAAT GAACAAGAAT 8230       8240       8250       8260       8270       8280
     TATTGGAATT GGATAAATGG GCAAGTTTGT GGAATTGGTT TGACATAACA AATTGGCTGT 8290       8300       8310       8320       8330       8340
     GGTATATAAA AATATTCATA ATGATAGTAG GAGGCTTGGT AGGTTTAAGA ATAGTTTTTG 8350       8360       8370       8380       8390       8400
     CTGTACTTTC TATAGTGAAT AGAGTTAGGC AGGGATACTC ACCATTGTCG TTGCAGACCC 8410       8420       8430       8440       8450       8460
     GCCCCCCAGT TCCGAGGGGA CCCGACAGGC CCGAAGGAAT CGAAGAAGAA GGTGGAGAGA 8470       8480       8490       8500       8510       8520
     GAGACAGAGA CACATCCGGT CGATTAGTGC ATGGATTCTT AGCAATTATC TGGGTCGACC 8530       8540       8550       8560       8570       8580
     TGCGGAGCCT GTTCCTCTTC AGCTACCACC ACAGAGACTT ACTCTTGATT GCAGCGAGGA 8590       8600       8610       8620       8630       8640
     TTGTGGAACT TCTGGGACGC AGGGGGTGGG AAGTCCTCAA ATATTGGTGG AATCTCCTAC 8650       8660       8670       8680       8690       8700
     AGTATTGGAG TCAGGAACTA AAGAGTAGTG CTGTTAGCTT GCTTAATGCC ACAGCTATAG 8710       8720       8730       8740       8750       8760
     CAGTAGCTGA GGGGACAGAT AGGGTTATAG AAGTACTGCA AAGAGCTGGT AGAGCTATTC 8770       8780       8790       8800       8810       8820
     TCCACATACC TACAAGAATA AGACAGGGCT TGGAAAGGGC TTTGCTATAA GATGGGTGGC
```

Figure 2H

```
         8830       8840       8850       8860       8870       8880
    AAATGGTCAA AACGTGTGAC TGGATGGCCT ACTGTAAGGG AAAGAATGAG ACGAGCTGAA 8890       8900       8910       8920       8930       8940
    CCAGCTGAGC TAGCAGCAGA TGGGGTGGGA GCAGCATCCC GAGACCTGGA AAAACATGGA 8950       8960       8970       8980       8990       9000
    GCACTCACAA GTAGCAATAC AGCAGCTACC AATGCTGATT GTGCCTGGCT AGAAGCACAA 9010       9020       9030       9040       9050       9060
    GAGGAGGAGG AAGTGGGTTT TCCAGTCAAA CCTCAGGTAC CTTTAAGACC AATGACTTAC 9070       9080       9090       9100       9110       9120
    AAAGCAGCTT TAGATCTTAG CCACTTTTTA AAAGAAAAGG GGGGACTGGA TGGGTTAATT 9130       9140       9150       9160       9170       9180
    TACTCCCAAA AGAGACAAGA CATCCTTGAT CTGTGGGTCT ACCACACACA AGGCTACTTC 9190       9200       9210       9220       9230       9240
    CCTGATTGGC AGAACTACAC ACCAGGGCCA GGGATCAGAT ATCCACTGAC CTTTGGATGG 9250       9260       9270       9280       9290       9300
    TGCTTCAAGC TAGTACCAGT TGAGCCAGAG AAGATAGAAG AGGCCAATAA AGGAGAGAAC 9310       9320       9330       9340       9350       9360
    AACTGCTTGT TACACCCTAT GAGCCAGCAT GGATGGATGA CCCGGAGAGA GAAGTGTTAG 9370       9380       9390       9400       9410       9420
    TGTGGAAGTC TGACAGCCAC CTAGCATTTC AGCATTATGC CCGAGAGCTG CATCCGGAGT 9430       9440       9450       9460       9470       9480
    ACTACAAGAA CTGCTGACAT CGAGCTATCT ACAAGGGACT TTCCGCTGGG GACTTTCCAG 9490       9500       9510       9520       9530       9540
    GGAGGTGTGG CCTGGGCGGG ACCGGGAGT GGCGAGCCCT CAGATCGTGC ATATAAGCAG 9550       9560       9570       9580       9590       9600
    CTGCTTTCTG CCTGTACTGG GTCTCTCTGG TTAGACCAGA TCTGAGCCTG GGAGCTCTCT 9610       9620       9630       9640       9650       9660
    GGCTAACTAG GGAACCCACT GCTTAAGCCT CAATAAAGCT TGCCTTGAGT GCTTCAAGTA 9670       9680       9690       9700       9710       9720
    GTGTGTGCCC GTCTGTTATG TGACTCTGGT AGCTAGAGAT CCCTCAGATC CTTTTAGGCA

9730
    GTGTGGAAAA TCTCTAGCA
```

```
          10         20         30         40         50         60
TGGATGGGTTAATTTACTCCCAAAGAGACAAGACATCCTTGATCTGTGGGTCTACCACAC
 W  M  G  *  F  T  P  K  E  T  R  H  P  *  S  V  G  L  P  H
  G  W  V  N  L  L  P  K  R  Q  D  I  L  D  L  W  V  Y  H  T
   D  G  L  I  Y  S  Q  R  D  K  T  S  L  I  C  G  S  T  T 70         80         90        100        110        120
ACAAGGCTACTTCCCTGATTGGCAGAACTACACACCAGGGCCAGGGATCAGATATCCACT
 T  R  L  L  P  *  L  A  E  L  H  T  R  A  R  D  Q  I  S  T
  Q  G  Y  F  P  D  W  Q  N  Y  T  P  G  P  G  I  R  Y  P  L
   H  K  A  T  S  L  I  G  R  T  T  H  Q  G  Q  G  S  D  I  H 130        140        150        160        170        180
GACCTTTGGATGGTGCTTCAAGCTAGTACCAGTTGAGCCAGAGAAGATAGAAGAGGCCAA
 D  L  W  M  V  L  Q  A  S  T  S  *  A  R  E  D  R  R  G  Q
  T  F  G  W  C  F  K  L  V  P  V  E  P  E  K  I  E  E  A  N
   *  P  L  D  G  A  S  S  *  Y  Q  L  S  Q  R  R  *  K  R  P 190        200        210        220        230        240
TAAAGGAGAGAACAACTGCTTGTTACACCCTATGAGCCAGCATGGGATGGATGACCCGGA
 *  R  R  E  Q  L  L  V  T  P  Y  E  P  A  W  D  G  *  P  G
  K  G  E  N  N  C  L  L  H  P  M  S  Q  H  G  M  D  D  P  E
   I  K  E  R  T  T  A  C  Y  T  L  *  A  S  M  G  W  M  T  R 250        260        270        280        290        300
GAGAGAAGTGTTAGTGTGGAAGTCTGACAGCCACCTAGCATTTCAGCATTATGCCCGAGA
 E  R  S  V  S  V  E  V  *  Q  P  P  S  I  S  A  L  C  P  R
  R  E  V  L  V  W  K  S  D  S  H  L  A  F  Q  H  Y  A  R  E
   R  E  K  C  *  C  G  S  L  T  A  T  *  H  F  S  I  M  P  E 310        320        330        340        350        360
GCTGCATCCGGAGTACTACAAGAACTGCTGACATCGAGCTATCTACAAGGGACTTTCCGC
 A  A  S  G  V  L  Q  E  L  L  T  S  S  Y  L  Q  G  T  F  R
  L  H  P  E  Y  Y  K  N  C  *  H  R  A  I  Y  K  G  L  S  A
   S  C  I  R  S  T  T  R  T  A  D  I  E  L  S  T  R  D  F  P 370        380        390        400        410        420
TGGGGACTTTCCAGGGAGGTGTGGCCTGGGCGGGACCGGGGAGTGGCGAGCCCTCAGATG
 W  G  L  S  R  E  V  W  P  G  R  D  R  G  V  A  S  P  Q  M
  G  D  F  P  G  R  C  G  L  G  G  T  G  E  W  R  A  L  R  C
   L  G  T  F  Q  G  G  V  A  W  A  G  P  G  S  G  E  P  S  D 430        440        450        460        470        480
CTGCATATAAGCAGCTGCTTTCTGCCTGTACTGGGTCTCTCTGGTTAGACCAGATCTGAG
 L  H  I  S  S  C  F  L  P  V  L  G  L  S  G  *  T  R  S  E
  C  I  *  A  A  A  F  C  L  Y  W  V  S  L  V  R  P  D  L  S
   A  A  Y  K  Q  L  L  S  A  C  T  G  S  L  W  L  D  Q  I  *

490        500        510        520        530        540
CCTGGGAGCTCTCTGGCTAACTAGGGAACCCACTGCTTAAGCCTCAATAAAGCTTGCCTT
 P  G  S  S  L  A  N  *  G  T  H  C  L  S  L  N  K  A  C  L
  L  G  A  L  W  L  T  R  E  P  T  A  *  A  S  I  K  L  A  L
   A  W  E  L  S  G  *  L  G  N  P  L  L  K  P  Q  *  S  L  P
```

Figure 6B

```
          550       560       570       580       590       600
GAGTGCTTCAAGTAGTGTGTGCCCGTCTGTTATGTGACTCTGGTAGCTAGAGATCCCTCA
 E  C  F  K  *  C  V  P  V  C  Y  V  T  L  V  A  R  D  P  S
  S  A  S  S  S  V  C  P  S  V  M  *  L  W  *  L  E  I  P  Q
*  V  L  Q  V  V  C  A  R  L  L  C  D  S  G  S  *  R  S  L 610       620       630       640       650       660
GATCCTTTTAGGCAGTGTGGAAAATCTCTAGCAGTGGCGCCCGAACAGGGACTTGAAAGC
 D  P  F  R  Q  C  G  K  S  L  A  V  A  P  E  Q  G  L  E  S
  I  L  L  G  S  V  E  N  L  *  Q  W  R  P  N  R  D  L  K  A
   R  S  F  *  A  V  W  K  I  S  S  S  G  A  R  T  G  T  *  K 670       680       690       700       710       720
GAAAGAGAAACCAGAGGAGCTCTCTCGACGCAGGACTCGGCTTGCTGAAGCGCGCACGGC
 E  R  E  T  R  G  A  L  S  T  Q  D  S  A  C  *  S  A  H  G
  K  E  K  P  E  E  L  S  R  R  R  T  R  L  A  E  A  R  T  A
   R  K  R  N  Q  R  S  S  L  D  A  G  L  G  L  L  K  R  A  R 730       740       750       760       770       780
AAGAGGCGAGGGGCGGCGACTGGTGAGTACGCCAAAATTCTTGACTAGCGGAGGCTAGAA
 K  R  R  G  A  A  T  G  E  Y  A  K  I  L  D  *  R  R  L  E
  R  G  E  G  R  R  L  V  S  T  P  K  F  L  T  S  G  G  *  K
   Q  E  A  R  G  G  D  W  *  V  R  Q  N  S  *  L  A  E  A  R 790       800       810       820       830       840
GGAGAGAGATGGGTGCGAGAGCGTCGGTATTAAGCGGGGGAGAATTAGATCGATGGGAAA
 G  E  R  W  V  R  E  R  R  Y  *  A  G  E  N  *  I  D  G  K
  E  R  D  G  C  E  S  V  G  I  K  R  G  R  I  R  S  M  G  K
   R  R  E  M  G  A  R  A  S  V  L  S  G  G  E  L  D  R  W  E 850       860       870       880       890       900
AAATTCGGTTAAGGCCAGGGGGAAAGAAAAAATATAAATTAAAACATGTAGTATGGGCAA
 K  F  G  *  G  Q  G  E  R  K  N  I  N  *  N  M  *  Y  G  Q
  N  S  V  K  A  R  G  K  E  K  I  *  I  K  T  C  S  M  G  K
   K  I  R  L  R  P  G  G  K  K  K  Y  K  L  K  H  V  V  W  A 910       920       930       940       950       960
GCAGGGAGCTAGAACGATTCGCAGTCAATCCTGGCCTGTTAGAAACATCAGAAGGCTGTA
 A  G  S  *  N  D  S  Q  S  I  L  A  C  *  K  H  Q  K  A  V
  Q  G  A  R  T  I  R  S  Q  S  W  P  V  R  N  I  R  R  L  *
   S  R  E  L  E  R  F  A  V  N  P  G  L  L  E  T  S  E  G  C 970       980       990      1000      1010      1020
GACAAATACTGGGACAGCTACAACCATCCCTTCAGACAGGATCAGAAGAACTTAAATCAT
 D  K  Y  W  D  S  Y  N  H  P  F  R  Q  D  Q  K  N  L  N  H
  T  N  T  G  T  A  T  T  I  P  S  D  R  I  R  R  T  *  I  I
   R  Q  I  L  G  Q  L  Q  P  S  L  Q  T  G  S  E  E  L  K  S 1030      1040      1050      1060      1070      1080
TATATAATACAGTAGCAACCCTCTATTGTGTGCATCAAAAGATAGAGATAAAAGACACCA
 Y  I  I  Q  *  Q  P  S  I  V  C  I  K  R  *  R  *  K  T  P
  I  *  Y  S  S  N  P  L  L  C  A  S  K  D  R  D  K  R  H  Q
   L  Y  N  T  V  A  T  L  Y  C  V  H  Q  K  I  E  I  K  D  T
```

Figure 6C

```
          1090       1100       1110       1120       1130       1140
    AGGAAGCTTTAGAGAAAATAGAGGAAGAGCAAAACAAAAGTAAGAAAAAAGCACAGCAAG
     R  K  L  *  R  K  *  R  K  S  K  T  K  V  R  K  K  H  S  K
       G  S  F  R  E  N  R  G  R  A  K  Q  K  *  E  K  S  T  A  S
     K  E  A  L  E  K  I  E  E  E  Q  N  K  S  K  K  K  A  Q  Q 1150       1160       1170       1180       1190       1200
    CAGTAGCTGACACAGGAAACAGAGGAAACAGCAGCCAAGTCAGCCAAAATTACCCCATAG
     Q  *  L  T  Q  E  T  E  E  T  A  A  K  S  A  K  I  T  P  *
       S  S  *  H  R  K  Q  R  K  Q  Q  P  S  Q  P  K  L  P  H  S
     A  V  A  D  T  G  N  R  G  N  S  S  Q  V  S  Q  N  Y  P  I 1210       1220       1230       1240       1250       1260
    TGCAGAACATCCAGGGGCAAATGGTACATCAGGCCATATCACCTAGAACTTTAAATGCAT
     C  R  T  S  R  G  K  W  Y  I  R  P  Y  H  L  E  L  *  M  H
       A  E  H  P  G  A  N  G  T  S  G  H  I  T  *  N  F  K  C  M
     V  Q  N  I  Q  G  Q  M  V  H  Q  A  I  S  P  R  T  L  N  A 1270       1280       1290       1300       1310       1320
    GGGTAAAAGTAGTAGAAGAGAAGGCTTTCAGCCCAGAAGTAATACCCATGTTTTCAGCAT
     G  *  K  *  *  K  R  R  L  S  A  Q  K  *  Y  P  C  F  Q  H
       G  K  S  S  R  R  E  G  F  Q  P  R  S  N  T  H  V  F  S  I
     W  V  K  V  V  E  E  K  A  F  S  P  E  V  I  P  M  F  S  A 1330       1340       1350       1360       1370       1380
    TATCAGAAGGAGCCACCCCACAAGATTTAAACACCATGCTAAACACAGTGGGGGGACATC
     Y  Q  K  E  P  P  H  K  I  *  T  P  C  *  T  Q  W  G  D  I
       I  R  R  S  H  P  T  R  F  K  H  H  A  K  H  S  G  G  T  S
     L  S  E  G  A  T  P  Q  D  L  N  T  M  L  N  T  V  G  G  H 1390       1400       1410       1420       1430       1440
    AAGCAGCCATGCAAATGTTAAAAGAGACCATCAATGAGGAAGCTGCAGAATGGGATAGAT
     K  Q  P  C  K  C  *  K  R  P  S  M  R  K  L  Q  N  G  I  D
       S  S  H  A  N  V  K  R  D  H  Q  *  G  S  C  R  M  G  *  I
     Q  A  A  M  Q  M  L  K  E  T  I  N  E  E  A  A  E  W  D  R 1450       1460       1470       1480       1490       1500
    TGCATCCAGTGCATGCAGGGCCTATTGCACCAGGCCAGATGAGAGAACCAAGGGGAAGTG
     C  I  Q  C  M  Q  G  L  L  H  Q  A  R  *  E  N  Q  G  E  V
       A  S  S  A  C  R  A  Y  C  T  R  P  D  E  R  T  K  G  K  *
     L  H  P  V  H  A  G  P  I  A  P  G  Q  M  R  E  P  R  G  S 1510       1520       1530       1540       1550       1560
    ACATAGCAGGAACTACTAGTACCCTTCAGGAACAAATAGGATGGATGACAAATAATCCAC
     T  *  Q  E  L  L  V  P  F  R  N  K  *  D  G  *  Q  I  I  H
       H  S  R  N  Y  *  Y  P  S  G  T  N  R  M  D  D  K  *  S  T
     D  I  A  G  T  T  S  T  L  Q  E  Q  I  G  W  M  T  N  N  P 1570       1580       1590       1600       1610       1620
    CTATCCCAGTAGGAGAAATCTATAAAAGATGGATAATCCTGGGATTAAATAAAATAGTAA
     L  S  Q  *  E  K  S  I  K  D  G  *  S  W  D  *  I  K  *  *
       Y  P  S  R  R  N  L  *  K  M  D  N  P  G  I  K  *  N  S  K
     P  I  P  V  G  E  I  Y  K  R  W  I  I  L  G  L  N  K  I  V
```

Figure 6D

```
          1630      1640      1650      1660      1670      1680
     GGATGTATAGCCCTTCCAGCATTCTGGACATAAGACAAGGACCAAAGGAACCCTTTAGAG
      G  C  I  A  L  P  A  F  W  T  *  D  K  D  Q  R  N  P  L  E
       D  V  *  P  F  Q  H  S  G  H  K  T  R  T  K  G  T  L  *  R
     R  M  Y  S  P  S  S  I  L  D  I  R  Q  G  P  K  E  P  F  R 1690      1700      1710      1720      1730      1740
     ACTATGTAGACCGGTTCTATAAAACTCTAAGAGCCGAGCAAGCTTCACAGGAGGTAAAAA
      T  M  *  T  G  S  I  K  L  *  E  P  S  K  L  H  R  R  *  K
       L  C  R  P  V  L  *  N  S  K  S  R  A  S  F  T  G  G  K  K
     D  Y  V  D  R  F  Y  K  T  L  R  A  E  Q  A  S  Q  E  V  K 1750      1760      1770      1780      1790      1800
     ATTGGATGACAGAAACCTTGTTGGTCCAAAATGCGAACCCAGATTGTAAGACTATTTTAA
      I  G  *  Q  K  P  C  W  S  K  M  R  T  Q  I  V  R  L  F  *
       L  D  D  R  N  L  V  G  P  K  C  E  P  R  L  *  D  Y  F  K
     N  W  M  T  E  T  L  L  V  Q  N  A  N  P  D  C  K  T  I  L 1810      1820      1830      1840      1850      1860
     AAGCATTGGGACCAGCAGCTACACTAGAAGAAATGATGACAGCATGTCAGGGAGTGGGAG
      K  H  W  D  Q  Q  L  H  *  K  K  *  *  Q  H  V  R  E  W  E
       S  I  G  T  S  S  Y  T  R  R  N  D  D  S  M  S  G  S  G  R
     K  A  L  G  P  A  A  T  L  E  E  M  M  T  A  C  Q  G  V  G 1870      1880      1890      1900      1910      1920
     GACCTGGTCATAAAGCAAGAGTTTTGGCGGAAGCGATGAGCCAAGTAACAAATTCAGCTA
      D  L  V  I  K  Q  E  F  W  R  K  R  *  A  K  *  Q  I  Q  L
       T  W  S  *  S  K  S  F  G  G  S  D  E  P  S  N  K  F  S  Y
     G  P  G  H  K  A  R  V  L  A  E  A  M  S  Q  V  T  N  S  A 1930      1940      1950      1960      1970      1980
     CCATAATGATGCAGAGAGGCAATTTTAGGAATCAAAGAAAGATTATCAAGTGCTTCAATT
      P  *  *  C  R  E  A  I  L  G  I  K  E  R  L  S  S  A  S  I
       H  N  D  A  E  R  Q  F  *  E  S  K  K  D  Y  Q  V  L  Q  L
     T  I  M  M  Q  R  G  N  F  R  N  Q  R  K  I  I  K  C  F  N 1990      2000      2010      2020      2030      2040
     GTGGCAAAGAAGGGCACATAGCCAAAAATTGCAGGGCCCCTAGGAAAAGGGGCTGTTGGA
      V  A  K  K  G  T  *  P  K  I  A  G  P  L  G  K  G  A  V  G
       W  Q  R  R  A  H  S  Q  K  L  Q  G  P  *  E  K  G  L  L  E
     C  G  K  E  G  H  I  A  K  N  C  R  A  P  R  K  R  G  C  W 2050      2060      2070      2080      2090      2100
     AATGTGGAAAGGAAGGACACCAAATGAAAGATTGTACTGAGAGACAGGCTAATTTTTTAG
      N  V  E  R  K  D  T  K  *  K  I  V  L  R  D  R  L  I  F  *
       M  W  K  G  R  T  P  N  E  R  L  Y  *  E  T  G  *  F  F  R
     K  C  G  K  E  G  H  Q  M  K  D  C  T  E  R  Q  A  N  F  L 2110      2120      2130      2140      2150      2160
     GGAAGATCTGGCCTTCCTGCAAGGGAAGGCAGGGAATTTTCCTCAGAGCAGAACAGAGCC
      G  R  S  G  L  P  A  R  E  G  R  E  F  S  S  E  Q  N  R  A
       E  D  L  A  F  L  Q  G  K  A  G  N  F  P  Q  S  R  T  E  P
     G  K  I  W  P  S  C  K  G  R  Q  G  I  F  L  R  A  E  Q  S
```

Figure 6E

```
         2170      2180      2190      2200      2210      2220
    AACAGCCCCACCAGAAGAGAGCTTCAGGTTTGGGGAAGAGACAACAACTCCCTATCAGAA
     N  S  P  T  R  R  E  L  Q  V  W  G  R  D  N  N  S  L  S  E
      T  A  P  P  E  E  S  F  R  F  G  E  E  T  T  T  P  Y  Q  K
    Q  Q  P  H  Q  K  R  A  S  G  L  G  K  R  Q  Q  L  P  I  R 2230      2240      2250      2260      2270      2280
    GCAGGAGAAGAAGCAGGAGACGATAGACAAGGACCTGTATCCTTTAGCTTCCCTCAAATC
     A  G  E  E  A  G  D  D  R  Q  G  P  V  S  F  S  F  P  Q  I
      Q  E  K  K  Q  E  T  I  D  K  D  L  Y  P  L  A  S  L  K  S
    S  R  R  R  S  R  R  R  *  T  R  T  C  I  L  *  L  P  S  N 2290      2300      2310      2320      2330      2340
    ACTCTTTGGCAACGACCCATTGTCACAATAAAGATAGGGGGGCAACTAAAGGAAGCTCTA
     T  L  W  Q  R  P  I  V  T  I  K  I  G  G  Q  L  K  E  A  L
      L  F  G  N  D  P  L  S  Q  *  R  *  G  G  N  *  R  K  L  Y
    H  S  L  A  T  T  H  C  H  N  K  D  R  G  A  T  K  G  S  S 2350      2360      2370      2380      2390      2400
    TTAGATACAGGAGCAGATGATACAGTATTAGAAGAAATGAATTTGCCAGGAAGATGGAAA
     L  D  T  G  A  D  D  T  V  L  E  E  M  N  L  P  G  R  W  K
      *  I  Q  E  Q  M  I  Q  Y  *  K  K  *  I  C  Q  E  D  G  N
    I  R  Y  R  S  R  *  Y  S  I  R  R  N  E  F  A  R  K  M  E 2410      2420      2430      2440      2450      2460
    CCAAAAATGATAGGGGGAATTGGAGGTTTTATCAAAGTAAGACAGTATGATCAGATAACC
     P  K  M  I  G  G  I  G  G  F  I  K  V  R  Q  Y  D  Q  I  T
      Q  K  *  *  G  E  L  E  V  L  S  K  *  D  S  M  I  R  *  P
    T  K  N  D  R  G  N  W  R  F  Y  Q  S  K  T  V  *  S  D  N 2470      2480      2490      2500      2510      2520
    ATAGAAATCTGTGGACATAAAGCTATAGGTACAGTATTAGTAGGACCTACACCTGTCAAC
     I  E  I  C  G  H  K  A  I  G  T  V  L  V  G  P  T  P  V  N
      *  K  S  V  D  I  K  L  *  V  Q  Y  *  *  D  L  H  L  S  T
    H  R  N  L  W  T  *  S  Y  R  Y  S  I  S  R  T  Y  T  C  Q 2530      2540      2550      2560      2570      2580
    ATAATTGGAAGAAATCTGTTGACTCAGCTTGGGTGCACTTTAAATTTTCCCATTAGTCCT
     I  I  G  R  N  L  L  T  Q  L  G  C  T  L  N  F  P  I  S  P
      *  L  E  E  I  C  *  L  S  L  G  A  L  *  I  F  P  L  V  L
    H  N  W  K  K  S  V  D  S  A  W  V  H  F  K  F  S  H  *  S 2590      2600      2610      2620      2630      2640
    ATTGAAACTGTACCAGTAAAATTAAAGCCAGGAATGGATGGCCCAAAAGTTAAACAATGG
     I  E  T  V  P  V  K  L  K  P  G  M  D  G  P  K  V  K  Q  W
      L  K  L  Y  Q  *  N  *  S  Q  E  W  M  A  Q  K  L  N  N  G
    Y  *  N  C  T  S  K  I  K  A  R  N  G  W  P  K  S  *  T  M 2650      2660      2670      2680      2690      2700
    CCATTGACAGAAGAAAAAATAAAAGCATTAATAGAAATTTGTACAGAAATGGAAAAGGAA
     P  L  T  E  E  K  I  K  A  L  I  E  I  C  T  E  M  E  K  E
      H  *  Q  K  K  K  *  K  H  *  *  K  F  V  Q  K  W  K  R  K
    A  I  D  R  R  K  N  K  S  I  N  R  N  L  Y  R  N  G  K  G
```

Figure 6F

```
        2710      2720      2730      2740      2750      2760
     GGGAAAATTTCAAAAATTGGGCCTGAAAATCCATACAATACTCCAGTATTTGCCATAAAG
      G  K  I  S  K  I  G  P  E  N  P  Y  N  T  P  V  F  A  I  K
       G  K  F  Q  K  L  G  L  K  I  H  T  I  L  Q  Y  L  P  *  R
     R  E  N  F  K  N  W  A  *  K  S  I  Q  Y  S  S  I  C  H  K 2770      2780      2790      2800      2810      2820
     AAAAAAGACAGTACTAAATGGAGAAAATTAGTAGATTTCAGAGAACTTAATAAGAAAACT
      K  K  D  S  T  K  W  R  K  L  V  D  F  R  E  L  N  K  K  T
       K  K  T  V  L  N  G  E  N  *  *  I  S  E  N  L  I  R  K  L
     E  K  R  Q  Y  *  M  E  K  I  S  R  F  Q  R  T  *  *  E  N 2830      2840      2850      2860      2870      2880
     CAAGACTTCTGGGAAGTTCAATTAGGAATACCACATCCTGCAGGGTTAAAAAAGAAAAAA
      Q  D  F  W  E  V  Q  L  G  I  P  H  P  A  G  L  K  K  K  K
       K  T  S  G  K  F  N  *  E  Y  H  I  L  Q  G  *  K  R  K  N
     S  R  L  L  G  S  S  I  R  N  T  T  S  C  R  V  K  K  E  K 2890      2900      2910      2920      2930      2940
     TCAGTAACAGTACTGGATGTGGGTGATGCATATTTTTCAGTTCCCTTAGATAAAGACTTC
      S  V  T  V  L  D  V  G  D  A  Y  F  S  V  P  L  D  K  D  F
       Q  *  Q  Y  W  M  W  V  M  H  I  F  Q  F  P  *  I  K  T  S
     I  S  N  S  T  G  C  G  *  C  I  F  F  S  S  L  R  *  R  L 2950      2960      2970      2980      2990      3000
     AGGAAGTATACTGCATTTACCATACCTAGTATAAACAATGAAACACCAGGGATTAGATAT
      R  K  Y  T  A  F  T  I  P  S  I  N  N  E  T  P  G  I  R  Y
       G  S  I  L  H  L  P  Y  L  V  *  T  M  K  H  Q  G  L  D  I
     Q  E  V  Y  C  I  Y  H  T  *  Y  K  Q  *  N  T  R  D  *  I 3010      3020      3030      3040      3050      3060
     CAGTACAATGTGCTTCCACAGGGATGGAAAGGATCACCAGCAATATTCCAAAGTAGCATG
      Q  Y  N  V  L  P  Q  G  W  K  G  S  P  A  I  F  Q  S  S  M
       S  T  M  C  F  H  R  D  G  K  D  H  Q  Q  Y  S  K  V  A  *
     S  V  Q  C  A  S  T  G  M  E  R  I  T  S  N  I  P  K  *  H 3070      3080      3090      3100      3110      3120
     ACAAAAATCTTAGAGCCTTTTAGAAAACAAAATCCAGACATAGTTATCTATCAATACATG
      T  K  I  L  E  P  F  R  K  Q  N  P  D  I  V  I  Y  Q  Y  M
       Q  K  S  *  S  L  L  E  N  K  I  Q  T  *  L  S  I  N  T  W
     D  K  N  L  R  A  F  *  K  T  K  S  R  H  S  Y  L  S  I  H 3130      3140      3150      3160      3170      3180
     GATGATTTGTATGTAGGATCTGACTTAGAAATAGGGCAGCATAGAGCAAAAATAGAGGAA
      D  D  L  Y  V  G  S  D  L  E  I  G  Q  H  R  A  K  I  E  E
       M  I  C  M  *  D  L  T  *  K  *  G  S  I  E  Q  K  *  R  N
     G  *  F  V  C  R  I  *  L  R  N  R  A  A  *  S  K  N  R  G 3190      3200      3210      3220      3230      3240
     CTGAGACGACATCTGTTGAGGTGGGGATTTACCACACCAGACAAAAAACATCAGAAAGAA
      L  R  R  H  L  L  R  W  G  F  T  T  P  D  K  K  H  Q  K  E
       *  D  D  I  C  *  G  G  D  L  P  H  Q  T  K  N  I  R  K  N
     T  E  T  T  S  V  E  V  G  I  Y  H  T  R  Q  K  T  S  E  R
```

Figure 6G

```
         3250      3260      3270      3280      3290      3300
    CCTCCATTCCTTTGGATGGGTTATGAACTCCATCCTGATAAATGGACAGTACAGCCTATA
      P  P  F  L  W  M  G  Y  E  L  H  P  D  K  W  T  V  Q  P  I
       L  H  S  F  G  W  V  M  N  S  I  L  I  N  G  Q  Y  S  L  *
        T  S  I  P  L  D  G  L  *  T  P  S  *  *  M  D  S  T  A  Y 3310      3320      3330      3340      3350      3360
    GTGCTGCCAGAAAAAGACAGCTGGACTGTCAATGACATACAGAAGTTAGTGGGAAAATTG
      V  L  P  E  K  D  S  W  T  V  N  D  I  Q  K  L  V  G  K  L
       C  C  Q  K  K  T  A  G  L  S  M  T  Y  R  S  *  W  E  N  *
        S  A  A  R  K  R  Q  L  D  C  Q  *  H  T  E  V  S  G  K  I 3370      3380      3390      3400      3410      3420
    AATTGGGCAAGTCAAATTTACGCAGGGATTAAAGTAAAGCAATTATGTAAACTCCTTAGA
      N  W  A  S  Q  I  Y  A  G  I  K  V  K  Q  L  C  K  L  L  R
       I  G  Q  V  K  F  T  Q  G  L  K  *  S  N  Y  V  N  S  L  E
        E  L  G  K  S  N  L  R  R  D  *  S  K  A  I  M  *  T  P  *

3430      3440      3450      3460      3470      3480
    GGAACCAAAGCACTAACAGAAGTAATACCACTAACAGAAGAAGCAGAGCTAGAACTGGCA
      G  T  K  A  L  T  E  V  I  P  L  T  E  E  A  E  L  E  L  A
       E  P  K  H  *  Q  K  *  Y  H  *  Q  K  K  Q  S  *  N  W  Q
        R  N  Q  S  T  N  R  S  N  T  T  N  R  R  S  R  A  R  T  G 3490      3500      3510      3520      3530      3540
    GAAAACAGGGAAATTCTAAAAGAACCAGTACATGGAGTGTATTATGACCCATCAAAAGAC
      E  N  R  E  I  L  K  E  P  V  H  G  V  Y  Y  D  P  S  K  D
       K  T  G  K  F  *  K  N  Q  Y  M  E  C  I  M  T  H  Q  K  T
        R  K  Q  G  N  S  K  R  T  S  T  W  S  V  L  *  P  I  K  R 3550      3560      3570      3580      3590      3600
    TTAATAGCAGAAGTACAGAAGCAGGGGCAAGGCCAATGGACATATCAAATTTATCAAGAG
      L  I  A  E  V  Q  K  Q  G  Q  G  Q  W  T  Y  Q  I  Y  Q  E
       *  *  Q  K  Y  R  S  R  G  K  A  N  G  H  I  K  F  I  K  S
        L  N  S  R  S  T  E  A  G  A  R  P  M  D  I  S  N  L  S  R 3610      3620      3630      3640      3650      3660
    CCATTTAAAAATCTGAAAACAGGCAAATATGCAAGAATGAGGGGTGCCCACACTAATGAT
      P  F  K  N  L  K  T  G  K  Y  A  R  M  R  G  A  H  T  N  D
       H  L  K  I  *  K  Q  A  N  M  Q  E  *  G  V  P  T  L  M  M
        A  I  *  K  S  E  N  R  Q  I  C  K  N  E  G  C  P  H  *  *

3670      3680      3690      3700      3710      3720
    GTAAAACAATTAACAGAGGCAGTGCAAAAAATAGCCACAGAAAGCATAGTAATATGGGGA
      V  K  Q  L  T  E  A  V  Q  K  I  A  T  E  S  I  V  I  W  G
       *  N  N  *  Q  R  Q  C  K  K  *  P  Q  K  A  *  *  Y  G  E
        C  K  T  I  N  R  G  S  A  K  N  S  H  R  K  H  S  N  M  G 3730      3740      3750      3760      3770      3780
    AAGACTCCTAAATTTAGACTACCCATACAAAAAGAAACATGGGAAACATGGTGGACAGAG
      K  T  P  K  F  R  L  P  I  Q  K  E  T  W  E  T  W  W  T  E
       R  L  L  N  L  D  Y  P  Y  K  K  K  H  G  K  H  G  G  Q  S
        K  D  S  *  I  *  T  T  H  T  K  R  N  M  G  N  M  V  D  R
```

Figure 6H

```
       3790      3800      3810      3820      3830      3840
   TATTGGCAAGCCACCTGGATTCCTGAGTGGGAGTTTGTCAATACCCCTCCCTTAGTGAAA
    Y  W  Q  A  T  W  I  P  E  W  E  F  V  N  T  P  P  L  V  K
     I  G  K  P  P  G  F  L  S  G  S  L  S  I  P  L  P  *  *  N
   V  L  A  S  H  L  D  S  *  V  G  V  C  Q  Y  P  S  L  S  E 3850      3860      3870      3880      3890      3900
   TTATGGTACCAGTTAGAGAAAGAACCCATAGTAGGAGCAGAAACTTTCTATGTAGATGGG
    L  W  Y  Q  L  E  K  E  P  I  V  G  A  E  T  F  Y  V  D  G
     Y  G  T  S  *  R  K  N  P  *  *  E  Q  K  L  S  M  *  M  G
   I  M  V  P  V  R  E  R  T  H  S  R  S  R  N  F  L  C  R  W 3910      3920      3930      3940      3950      3960
   GCAGCTAACAGGGAGACTAAAAAAGGAAAAGCAGGATATGTTACTAACAGAGGAAGACAA
    A  A  N  R  E  T  K  K  G  K  A  G  Y  V  T  N  R  G  R  Q
     Q  L  T  G  R  L  K  K  E  K  Q  D  M  L  L  T  E  E  D  K
   G  S  *  Q  G  D  *  K  R  K  S  R  I  C  Y  *  Q  R  K  T 3970      3980      3990      4000      4010      4020
   AAGGTTGTCTCCCTAACTGACACAACAAATCAGAAGACTGAGTTACAAGCAATTCATCTA
    K  V  V  S  L  T  D  T  T  N  Q  K  T  E  L  Q  A  I  H  L
     R  L  S  P  *  L  T  Q  Q  I  R  R  L  S  Y  K  Q  F  I  *
   K  G  C  L  P  N  *  H  N  K  S  E  D  *  V  T  S  N  S  S 4030      4040      4050      4060      4070      4080
   GCTTTGCAAGATTCAGGGTTAGAAGTAAACATAGTAACAGACTCACAATATGCATTAGGA
    A  L  Q  D  S  G  L  E  V  N  I  V  T  D  S  Q  Y  A  L  G
     L  C  K  I  Q  G  *  K  *  T  *  *  Q  T  H  N  M  H  *  E
   S  F  A  R  F  R  V  R  S  K  H  S  N  R  L  T  I  C  I  R 4090      4100      4110      4120      4130      4140
   ATCATTCAAGCACAACCAGATAAAAGTGAATCAGAGTTAGTCAGTCAAATAATAGAGCAG
    I  I  Q  A  Q  P  D  K  S  E  S  E  L  V  S  Q  I  I  E  Q
     S  F  K  H  N  Q  I  K  V  N  Q  S  *  S  V  K  *  *  S  S
   N  H  S  S  T  T  R  *  K  *  I  R  V  S  Q  S  N  N  R  A 4150      4160      4170      4180      4190      4200
   TTAATAAAAAAGGAAAAGGTCTATCTGGCATGGGTACCAGCACACAAAGGAATTGGAGGA
    L  I  K  K  E  K  V  Y  L  A  W  V  P  A  H  K  G  I  G  G
     *  *  K  R  K  R  S  I  W  H  G  Y  Q  H  T  K  E  L  E  E
   V  N  K  K  G  K  G  L  S  G  M  G  T  S  T  Q  R  N  W  R 4210      4220      4230      4240      4250      4260
   AATGAACAAGTAGATAAATTAGTCAGTGCTGGAATCAGGAAAGTACTATTTTTAGATGGA
    N  E  Q  V  D  K  L  V  S  A  G  I  R  K  V  L  F  L  D  G
     M  N  K  *  I  N  *  S  V  L  E  S  G  K  Y  Y  F  *  M  E
   K  *  T  S  R  *  I  S  Q  C  W  N  Q  E  S  T  I  F  R  W 4270      4280      4290      4300      4310      4320
   ATAGATAAGGCCCAAGAAGACCATGAGAAATATCACAGTAATTGGAGAGCAATGGCTAGT
    I  D  K  A  Q  E  D  H  E  K  Y  H  S  N  W  R  A  M  A  S
     *  I  R  P  K  K  T  M  R  N  I  T  V  I  G  E  Q  W  L  V
   N  R  *  G  P  R  R  P  *  E  I  S  Q  *  L  E  S  N  G  *
```

Figure 6I

```
          4330      4340      4350      4360      4370      4380
GACTTTAACCTACCACCTATAGTAGCAAAAGAAATAGTAGCCAGCTGTGATAAATGTCAG
  D  F  N  L  P  P  I  V  A  K  E  I  V  A  S  C  D  K  C  Q
   T  L  T  Y  H  L  *  *  Q  K  K  *  *  P  A  V  I  N  V  S
 *  L  *  P  T  T  Y  S  S  K  R  N  S  S  Q  L  *  *  M  S 4390      4400      4410      4420      4430      4440
CTAAAAGGAGAAGCCATGCATGGACAAGTAGACTGTAGTCCAGGAATATGGCAACTAGAT
  L  K  G  E  A  M  H  G  Q  V  D  C  S  P  G  I  W  Q  L  D
    *  K  E  K  P  C  M  D  K  *  T  V  V  Q  E  Y  G  N  *  I
  A  K  R  R  S  H  A  W  T  S  R  L  *  S  R  N  M  A  T  R 4450      4460      4470      4480      4490      4500
TGTACACATTTAGAAGGAAAAGTTATCCTGGTAGCAGTTCATGTAGCCAGTGGATACATA
  C  T  H  L  E  G  K  V  I  L  V  A  V  H  V  A  S  G  Y  I
    V  H  I  *  K  E  K  L  S  W  *  Q  F  M  *  P  V  D  T  *
  L  Y  T  F  R  R  K  S  Y  P  G  S  S  S  C  S  Q  W  I  H 4510      4520      4530      4540      4550      4560
GAAGCAGAAGTTATTCCAGCAGAGACAGGGCAGGAGACAGCATACTTTCTCTTAAAATTA
  E  A  E  V  I  P  A  E  T  G  Q  E  T  A  Y  F  L  L  K  L
    K  Q  K  L  F  Q  Q  R  Q  G  R  R  Q  H  T  F  S  *  N  *
  R  S  R  S  Y  S  S  R  D  R  A  G  D  S  I  L  S  L  K  I 4570      4580      4590      4600      4610      4620
GCAGGAAGATGGCCAGTAAAAACAATACATACAGACAATGGCCCCAATTTCACCAGTACT
  A  G  R  W  P  V  K  T  I  H  T  D  N  G  P  N  F  T  S  T
    Q  E  D  G  Q  *  K  Q  Y  I  Q  T  M  A  P  I  S  P  V  L
  S  R  K  M  A  S  K  N  N  T  Y  R  Q  W  P  Q  F  H  Q  Y 4630      4640      4650      4660      4670      4680
ACGGTTAAGGCCGCCTGTTGGTGGGCGGGGATCAAGCAGGAATTTGGCATTCCCTACAAT
  T  V  K  A  A  C  W  W  A  G  I  K  Q  E  F  G  I  P  Y  N
    R  L  R  P  P  V  G  G  R  G  S  S  R  N  L  A  F  P  T  I
  Y  G  *  G  R  L  L  V  G  G  D  Q  A  G  I  W  H  S  L  Q 4690      4700      4710      4720      4730      4740
CCCCAAAGTCAAGGAGTAATAGAATCTATGAATAAAGAATTAAAGAAAATTATAGGACAG
  P  Q  S  Q  G  V  I  E  S  M  N  K  E  L  K  K  I  I  G  Q
    P  K  V  K  E  *  *  N  L  *  I  K  N  *  R  K  L  *  D  R
  S  P  K  S  R  S  N  R  I  Y  E  *  R  I  K  E  N  Y  R  T 4750      4760      4770      4780      4790      4800
GTAAGAGATCAGGCTGAACATCTTAAGACAGCAGTACAAATGGCAGTATTCATCCACAAT
  V  R  D  Q  A  E  H  L  K  T  A  V  Q  M  A  V  F  I  H  N
    *  E  I  R  L  N  I  L  R  Q  Q  Y  K  W  Q  Y  S  S  T  I
  G  K  R  S  G  *  T  S  *  D  S  S  T  N  G  S  I  H  P  Q 4810      4820      4830      4840      4850      4860
TTTAAAAGAAAAGGGGGGATTGGGGGGTACAGTGCAGGGGAAAGAATAGTAGACATAATA
  F  K  R  K  G  G  I  G  G  Y  S  A  G  E  R  I  V  D  I  I
    L  K  E  K  G  G  L  G  G  T  V  Q  G  K  E  *  *  T  *  *
  F  *  K  K  R  G  D  W  G  V  Q  C  R  G  K  N  S  R  H  N
```

Figure 6J

```
         4870      4880      4890      4900      4910      4920
    GCAACAGACATACAAACTAAAGAACTACAAAAACAAATTACAAAAATTCAAAATTTTCGG
     A  T  D  I  Q  T  K  E  L  Q  K  Q  I  T  K  I  Q  N  F  R
      Q  Q  T  Y  K  L  K  N  Y  K  N  K  L  Q  K  F  K  I  F  G
    S  N  R  H  T  N  *  R  T  T  K  T  N  Y  K  N  S  K  F  S 4930      4940      4950      4960      4970      4980
    GTTTATTACAGGGACAGCAGAGATCCACTTTGGAAAGGACCAGCAAAGCTTCTCTGGAAA
     V  Y  Y  R  D  S  R  D  P  L  W  K  G  P  A  K  L  L  W  K
      F  I  T  G  T  A  E  I  H  F  G  K  D  Q  Q  S  F  S  G  K
    G  L  L  Q  G  Q  Q  R  S  T  L  E  R  T  S  K  A  S  L  E 4990      5000      5010      5020      5030      5040
    GGTGAAGGGGCAGTAGTAATACAAGATAATAGTGACATAAAAGTAGTGCCAAGAAGAAAA
     G  E  G  A  V  V  I  Q  D  N  S  D  I  K  V  V  P  R  R  K
      V  K  G  Q  *  *  Y  K  I  I  V  T  *  K  *  C  Q  E  E  K
    R  *  R  G  S  S  N  T  R  *  *  *  H  K  S  S  A  K  K  K.

5050      5060      5070      5080      5090      5100
    GCAAAGATCATTAGGGATTATGGAAAACAGATGGCAGGTGATGATTGTGTGGCAAGTAGA
     A  K  I  I  R  D  Y  G  K  Q  M  A  G  D  D  C  V  A  S  R
      Q  R  S  L  G  I  M  E  N  R  W  Q  V  M  I  V  W  Q  V  D
    S  K  D  H  *  G  L  W  K  T  D  G  R  *  *  L  C  G  K  *

5110      5120      5130      5140      5150      5160
    CAGGATGAGGATTAGAACATGGAAAAGTTTAGTAAAACACCATATGTATATTTCAAAGAA
     Q  D  E  D  *  N  M  E  K  F  S  K  T  P  Y  V  Y  F  K  E
      R  M  R  I  R  T  W  K  S  L  V  K  H  H  M  Y  I  S  K  K
    T  G  *  G  L  E  H  G  K  V  *  *  N  T  I  C  I  F  Q  R 5170      5180      5190      5200      5210      5220
    AGCTAAAGGATGGTTTTATAGACATCACTATGAAAGCACTCATCCAAGAATAAGTTCAGA
     S  *  R  M  V  L  *  T  S  L  *  K  H  S  S  K  N  K  F  R
      A  K  G  W  F  Y  R  H  H  Y  E  S  T  H  P  R  I  S  S  E
    K  L  K  D  G  F  I  D  I  T  M  K  A  L  I  Q  E  *  V  Q 5230      5240      5250      5260      5270      5280
    AGTACACATCCCACTAGGGGATGCTAGATTGGTAATAACAACATATTGGGGTCTGCATAC
     S  T  H  P  T  R  G  C  *  I  G  N  N  N  I  L  G  S  A  Y
      V  H  I  P  L  G  D  A  R  L  V  I  T  T  Y  W  G  L  H  T
    K  Y  T  S  H  *  G  M  L  D  W  *  *  Q  H  I  G  V  C  I 5290      5300      5310      5320      5330      5340
    AGGAGAAAGAGACTGGCATTTAGGTCAGGGAGTCTCCATAGAATGGAGGAAAAAGAGATA
     R  R  K  R  L  A  F  R  S  G  S  L  H  R  M  E  E  K  E  I
      G  E  R  D  W  H  L  G  Q  G  V  S  I  E  W  R  K  K  R  Y
    Q  E  K  E  T  G  I  *  V  R  E  S  P  *  N  G  G  K  R  D 5350      5360      5370      5380      5390      5400
    TAGCACACAAGTAGACCCTGACCTAGCAGACCACCTAATTCATCTGCATTACTTTGATTG
     *  H  T  S  R  P  *  P  S  R  P  P  N  S  S  A  L  L  *  L
      S  T  Q  V  D  P  D  L  A  D  H  L  I  H  L  H  Y  F  D  C
    I  A  H  K  *  T  L  T  *  Q  T  T  *  F  I  C  I  T  L  I
```

Figure 6K

```
         5410       5420       5430       5440       5450       5460
   TTTTTCAGACTCTGCCATAAGAAAGGCCATATTAGGACATAGAGTTAGTCCTATTTGTGA
    F  F  R  L  C  H  K  K  G  H  I  R  T  *  S  *  S  Y  L  *
     F  S  D  S  A  I  R  K  A  I  L  G  H  R  V  S  P  I  C  E
   V  F  Q  T  L  P  *  E  R  P  Y  *  D  I  E  L  V  L  F  V 5470       5480       5490       5500       5510       5520
   ATTTCAAGCAGGACATAACAAGGTAGGATCTCTACAGTACTTGGCACTAACAGCATTAAT
    I  S  S  R  T  *  Q  G  R  I  S  T  V  L  G  T  N  S  I  N
     F  Q  A  G  H  N  K  V  G  S  L  Q  Y  L  A  L  T  A  L  I
   N  F  K  Q  D  I  T  R  *  D  L  Y  S  T  W  H  *  Q  H  *

5530       5540       5550       5560       5570       5580
   AACACCAAAAAAGATAAAGCCACCTTTGCCTAGTGTTAAGAAACTGACAGAGGATAGATG
    N  T  K  K  D  K  A  T  F  A  *  C  *  E  T  D  R  G  *  M
     T  P  K  K  I  K  P  P  L  P  S  V  K  K  L  T  E  D  R  W
   *  H  Q  K  R  *  S  H  L  C  L  V  L  R  N  *  Q  R  I  D 5590       5600       5610       5620       5630       5640
   GAACAAGCCCCAGAAGACCAAGGGCCACAGAGGGAGCCATACAATCAATGGGCATTAGAG
    E  Q  A  P  E  D  Q  G  P  Q  R  E  P  Y  N  Q  W  A  L  E
     N  K  P  Q  K  T  K  G  H  R  G  S  H  T  I  N  G  H  *  S
   G  T  S  P  R  R  P  R  A  T  E  G  A  I  Q  S  M  G  I  R 5650       5660       5670       5680       5690       5700
   CTTTTAGAGGAGCTTAAGAATGAAGCTGTTAGACATTTTCCTAGGATATGGCTCCATGGC
    L  L  E  E  L  K  N  E  A  V  R  H  F  P  R  I  W  L  H  G
     F  *  R  S  L  R  M  K  L  L  D  I  F  L  G  Y  G  S  M  A
   A  F  R  G  A  *  E  *  S  C  *  T  F  S  *  D  M  A  P  W 5710       5720       5730       5740       5750       5760
   TTAGGGCAACATATCTATGAAACTTATGGGGATACTTGGGCAGGAGTGGAAGCCATAATA
    L  G  Q  H  I  Y  E  T  Y  G  D  T  W  A  G  V  E  A  I  I
     *  G  N  I  S  M  K  L  M  G  I  L  G  Q  E  W  K  P  *  *
   L  R  A  T  Y  L  *  N  L  W  G  Y  L  G  R  S  G  S  H  N 5770       5780       5790       5800       5810       5820
   AGAATTCTACAACAACTGCTGTTTATTCATTTCAGAATTGGGTGTCGACATAGCAGAATA
    R  I  L  Q  Q  L  L  F  I  H  F  R  I  G  C  R  H  S  R  I
     E  F  Y  N  N  C  C  L  F  I  S  E  L  G  V  D  I  A  E  *
   K  N  S  T  T  T  A  V  Y  S  F  Q  N  W  V  S  T  *  Q  N 5830       5840       5850       5860       5870       5880
   GGCATTATTCGACAGAGGAGAGCAAGAAATGGAGCCAGTAGATCCTAGACTAGAGCCCTG
    G  I  I  R  Q  R  R  A  R  N  G  A  S  R  S  *  T  R  A  L
     A  L  F  D  R  G  E  Q  E  M  E  P  V  D  P  R  L  E  P  W
   R  H  Y  S  T  E  E  S  K  K  W  S  Q  *  I  L  D  *  S  P 5890       5900       5910       5920       5930       5940
   GAAGCATCCAGGAAGTCAGCCTAAGACTGCTTGTACCACTTGCTATTGTAAAAAGTGTTG
    E  A  S  R  K  S  A  *  D  C  L  Y  H  L  L  L  *  K  V  L
     K  H  P  G  S  Q  P  K  T  A  C  T  T  C  Y  C  K  K  C  C
   G  S  I  Q  E  V  S  L  R  L  L  V  P  L  A  I  V  K  S  V
```

Figure 6L

```
         5950      5960      5970      5980      5990      6000
CTTTCATTGCCAAGTTTGTTTCACAAAAAAAGCCTTAGGCATCTCCTATGGCAGGAAGAA
 L  S  L  P  S  L  F  H  K  K  S  L  R  H  L  L  W  Q  E  E
  F  H  C  Q  V  C  F  T  K  K  A  L  G  I  S  Y  G  R  K  K
A  F  I  A  K  F  V  S  Q  K  K  P  *  A  S  P  M  A  G  R 6010      6020      6030      6040      6050      6060
GCGGAGACAGCGACGAAGAGCTCCTGAAGACAGTCAGACTCATCAAGTTTCTCTACCAAA
 A  E  T  A  T  K  S  S  *  R  Q  S  D  S  S  S  F  S  T  K
  R  R  Q  R  R  R  A  P  E  D  S  Q  T  H  Q  V  S  L  P  K
S  G  D  S  D  E  E  L  L  K  T  V  R  L  I  K  F  L  Y  Q 6070      6080      6090      6100      6110      6120
GCAGTAAGTAGTACATGTAATGCAACCTTTAGTAATAGCAGCAATAGTAGCATTAGTAGT
 A  V  S  S  T  C  N  A  T  F  S  N  S  S  N  S  S  I  S  S
  Q  *  V  V  H  V  M  Q  P  L  V  I  A  A  I  V  A  L  V  V
S  S  K  *  Y  M  *  C  N  L  *  *  *  Q  Q  *  *  H  *  *

6130      6140      6150      6160      6170      6180
AGCAGGAATAATAGCAATAGTTGTGTGATCCATAGTATTCATAGAATATAGGAAAATAAG
 S  R  N  N  S  N  S  C  V  I  H  S  I  H  R  I  *  E  N  K
  A  G  I  I  A  I  V  V  *  S  I  V  F  I  E  Y  R  K  I  R
*  Q  E  *  *  Q  *  L  C  D  P  *  Y  S  *  N  I  G  K  *

6190      6200      6210      6220      6230      6240
AAGACAAAGAAAAATAGACAGGGTAATTGACAGAATAAGCGAAAGAGCAGAAGACAGTGG
 K  T  K  K  N  R  Q  G  N  *  Q  N  K  R  K  S  R  R  Q  W
  R  Q  R  K  I  D  R  V  I  D  R  I  S  E  R  A  E  D  S  G
E  D  K  E  K  *  T  G  *  L  T  E  *  A  K  E  Q  K  T  V 6250      6260      6270      6280      6290      6300
CAATGAGAGTGAAGGGGATCAGGAGGAATTATCAGCACTGGTGGGGATGGGGCACGATGC
 Q  *  E  *  R  G  S  G  G  I  I  S  T  G  G  D  G  A  R  C
  N  E  S  E  G  D  Q  E  E  L  S  A  L  V  G  M  G  H  D  A
A  M  R  V  K  G  I  R  R  N  Y  Q  H  W  W  G  W  G  T  M 6310      6320      6330      6340      6350      6360
TCCTTGGGTTATTAATGATCTGTAGTGCTACAGAAAAATTGTGGGTCACAGTCTATTATG
 S  L  G  Y  *  *  S  V  V  L  Q  K  N  C  G  S  Q  S  I  M
  P  W  V  I  N  D  L  *  C  Y  R  K  I  V  G  H  S  L  L  W
L  L  G  L  L  M  I  C  S  A  T  E  K  L  W  V  T  V  Y  Y 6370      6380      6390      6400      6410      6420
GGGTACCTGTGTGGAAAGAAGCAACCACCACTCTATTTTGTGCATCAGATGCTAAAGCAT
 G  Y  L  C  G  K  K  Q  P  P  L  Y  F  V  H  Q  M  L  K  H
  G  T  C  V  E  R  S  N  H  H  S  I  L  C  I  R  C  *  S  I
G  V  P  V  W  K  E  A  T  T  T  L  F  C  A  S  D  A  K  A 6430      6440      6450      6460      6470      6480
ATGATACAGAGGTACATAATGTTTGGGCCACACATGCCTGTGTACCCACAGACCCCAACC
 M  I  Q  R  Y  I  M  F  G  P  H  M  P  V  Y  P  Q  T  P  T
  *  Y  R  G  T  *  C  L  G  H  T  C  L  C  T  H  R  P  Q  P
Y  D  T  E  V  H  N  V  W  A  T  H  A  C  V  P  T  D  P  N
```

Figure 6M

```
            6490      6500      6510      6520      6530      6540
        CACAAGAAGTAGAATTGGTAAATGTGACAGAAAATTTTAACATGTGGAAAAATAACATGG
         H  K  K  *  N  W  *  M  *  Q  K  I  L  T  C  G  K  I  T  W
          T  R  S  R  I  G  K  C  D  R  K  F  *  H  V  E  K  *  H  G
           P  Q  E  V  E  L  V  N  V  T  E  N  F  N  M  W  K  N  N  M 6550      6560      6570      6580      6590      6600
        TAGAACAGATGCATGAGGATATAATCAGTTTATGGGATCAAAGCCTAAAGCCATGTGTAA
         *  N  R  C  M  R  I  *  S  V  Y  G  I  K  A  *  S  H  V  *
          R  T  D  A  *  G  Y  N  Q  F  M  G  S  K  P  K  A  M  C  K
           V  E  Q  M  H  E  D  I  I  S  L  W  D  Q  S  L  K  P  C  V 6610      6620      6630      6640      6650      6660
        AATTAACCCCACTCTGTGTTACTTTAAATTGCACTGATTTGAGGAATACTACTAATACCA
         N  *  P  H  S  V  L  L  *  I  A  L  I  *  G  I  L  L  I  P
          I  N  P  T  L  C  Y  F  K  L  H  *  F  E  E  Y  Y  *  Y  Q
           K  L  T  P  L  C  V  T  L  N  C  T  D  L  R  N  T  T  N  T 6670      6680      6690      6700      6710      6720
        ATAATAGTACTGCTAATAACAATAGTAATAGCGAGGGAACAATAAAGGGAGGAGAAATGA
          I  I  V  L  L  I  T  I  V  I  A  R  E  Q  *  R  E  E  K  *
           *  *  Y  C  *  *  Q  *  *  *  R  G  N  N  K  G  R  R  N  E
         N  N  S  T  A  N  N  N  S  N  S  E  G  T  I  K  G  G  E  M 6730      6740      6750      6760      6770      6780
        AAAACTGCTCTTTCAATATCACCACAAGCATAAGAGATAAGATGCAGAAAGAATATGCAC
         K  T  A  L  S  I  S  P  Q  A  *  E  I  R  C  R  K  N  M  H
          K  L  L  F  Q  Y  H  H  K  H  K  R  *  D  A  E  R  I  C  T
           K  N  C  S  F  N  I  T  T  S  I  R  D  K  M  Q  K  E  Y  A 6790      6800      6810      6820      6830      6840
        TTCTTTATAAACTTGATATAGTATCAATAAATAATGATAGTACCAGCTATAGGTTGATAA
         F  F  I  N  L  I  *  Y  Q  *  I  M  I  V  P  A  I  G  *  *
          S  L  *  T  *  Y  S  I  N  K  *  *  *  Y  Q  L  *  V  D  K
           L  L  Y  K  L  D  I  V  S  I  N  N  D  S  T  S  Y  R  L  I 6850      6860      6870      6880      6890      6900
        GTTGTAATACCTCAGTCATTACACAAGCTTGTCCAAAGATATCCTTTGAGCCAATTCCCA
         V  V  I  P  Q  S  L  H  K  L  V  Q  R  Y  P  L  S  Q  F  P
          L  *  Y  L  S  H  Y  T  S  L  S  K  D  I  L  *  A  N  S  H
           S  C  N  T  S  V  I  T  Q  A  C  P  K  I  S  F  E  P  I  P 6910      6920      6930      6940      6950      6960
        TACACTATTGTGCCCCGGCTGGTTTTGCGATTCTAAAGTGTAACGATAAAAAGTTCAGTG
         Y  T  I  V  P  R  L  V  L  R  F  *  S  V  T  I  K  S  S  V
          T  L  L  C  P  G  W  F  C  D  S  K  V  *  R  *  K  V  Q  W
           I  H  Y  C  A  P  A  G  F  A  I  L  K  C  N  D  K  K  F  S 6970      6980      6990      7000      7010      7020
        GAAAAGGATCATGTAAAAATGTCAGCACAGTACAATGTACACATGGAATTAGGCCAGTAG
         E  K  D  H  V  K  M  S  A  Q  Y  N  V  H  M  E  L  G  Q  *
          K  R  I  M  *  K  C  Q  H  S  T  M  Y  T  W  N  *  A  S  S
           G  K  G  S  C  K  N  V  S  T  V  Q  C  T  H  G  I  R  P  V
```

Figure 6N

```
          7030      7040      7050      7060      7070      7080
     TATCAACTCAACTGCTGTTAAATGGCAGTCTAGCAGAAGAAGAGGTAGTAATTAGATCTG
       Y  Q  L  N  C  C  *  M  A  V  *  Q  K  K  R  *  *  L  D  L
        I  N  S  T  A  V  K  W  Q  S  S  R  R  R  G  S  N  *  I  *
      V  S  T  Q  L  L  L  N  G  S  L  A  E  E  E  V  V  I  R  S 7090      7100      7110      7120      7130      7140
     AGAATTTCAATGATAATGCTAAAACCATCATAGTACATCTGAATGAATCTGTACAAATTA
       R  I  S  M  I  M  L  K  P  S  *  Y  I  *  M  N  L  Y  K  L
        E  F  Q  *  *  C  *  N  H  H  S  T  S  E  *  I  C  T  N  *
      E  N  F  N  D  N  A  K  T  I  I  V  H  L  N  E  S  V  Q  I 7150      7160      7170      7180      7190      7200
     ATTGTACAAGACCCAACTACAATAAAAGAAAAAGGATACATATAGGACCAGGGAGAGCAT
       I  V  Q  D  P  T  T  I  K  E  K  G  Y  I  *  D  Q  G  E  H
        L  Y  K  T  Q  L  Q  *  K  K  K  D  T  Y  R  T  R  E  S  I
      N  C  T  R  P  N  Y  N  K  R  K  R  I  H  I  G  P  G  R  A 7210      7220      7230      7240      7250      7260
     TTTATACAACAAAAAATATAATAGGAACTATAAGACAAGCACATTGTAACATTAGTAGAG
       F  I  Q  Q  K  I  *  *  E  L  *  D  K  H  I  V  T  L  V  E
        L  Y  N  K  K  Y  N  R  N  Y  K  T  S  T  L  *  H  *  *  S
      F  Y  T  T  K  N  I  I  G  T  I  R  Q  A  H  C  N  I  S  R 7270      7280      7290      7300      7310      7320
     CAAAATGGAATGACACTTTAAGACAGATAGTTAGCAAATTAAAAGAACAATTTAAGAATA
       Q  N  G  M  T  L  *  D  R  *  L  A  N  *  K  N  N  L  R  I
        K  M  E  *  H  F  K  T  D  S  *  Q  I  K  R  T  I  *  E  *
      A  K  W  N  D  T  L  R  Q  I  V  S  K  L  K  E  Q  F  K  N 7330      7340      7350      7360      7370      7380
     AAACAATAGTCTTTAATCAATCCTCAGGAGGGGACCCAGAAATTGTAATGCACAGTTTTA
       K  Q  *  S  L  I  N  P  Q  E  G  T  Q  K  L  *  C  T  V  L
        N  N  S  L  *  S  I  L  R  R  G  P  R  N  C  N  A  Q  F  *
      K  T  I  V  F  N  Q  S  S  G  G  D  P  E  I  V  M  H  S  F 7390      7400      7410      7420      7430      7440
     ATTGTGGAGGGGAATTTTTCTACTGTAATACATCACCACTGTTTAATAGTACTTGGAATG
       I  V  E  G  N  F  S  T  V  I  H  H  H  C  L  I  V  L  G  M
        L  W  R  G  I  F  L  L  *  Y  I  T  T  V  *  *  Y  L  E  W
      N  C  G  G  E  F  F  Y  C  N  T  S  P  L  F  N  S  T  W  N 7450      7460      7470      7480      7490      7500
     GTAATAATACTTGGAATAATACTACAGGGTCAAATAACAATATCACACTTCAATGCAAAA
       V  I  I  L  G  I  I  L  Q  G  Q  I  T  I  S  H  F  N  A  K
        *  *  Y  L  E  *  Y  Y  R  V  K  *  Q  Y  H  T  S  M  Q  N
      G  N  N  T  W  N  N  T  T  G  S  N  N  N  I  T  L  Q  C  K 7510      7520      7530      7540      7550      7560
     TAAAACAAATTATAAACATGTGGCAGGAAGTAGGAAAAGCAATATATGCCCCTCCCATTG
       *  N  K  L  *  T  C  G  R  K  *  E  K  Q  Y  M  P  L  P  L
        K  T  N  Y  K  H  V  A  G  S  R  K  S  N  I  C  P  S  H  *
      I  K  Q  I  I  N  M  W  Q  E  V  G  K  A  I  Y  A  P  P  I
```

Figure 6O

```
        7570      7580      7590      7600      7610      7620
    AAGGACAAATTAGATGTTCATCAAATATTACAGGGCTACTATTAACAAGAGATGGTGGTA
     K  D  K  L  D  V  H  Q  I  L  Q  G  Y  Y  *  Q  E  M  V  V
      R  T  N  *  M  F  I  K  Y  Y  R  A  T  I  N  K  R  W  W  *
    E  G  Q  I  R  C  S  S  N  I  T  G  L  L  L  T  R  D  G  G 7630      7640      7650      7660      7670      7680
    AGGACACGGACACGAACGACACCGAGATCTTCAGACCTGGAGGAGGAGATATGAGGGACA
     R  T  R  T  R  T  T  P  R  S  S  D  L  E  E  E  I  *  G  T
      G  H  G  H  E  R  H  R  D  L  Q  T  W  R  R  R  Y  E  G  Q
    K  D  T  D  T  N  D  T  E  I  F  R  P  G  G  G  D  M  R  D 7690      7700      7710      7720      7730      7740
    ATTGGAGAAGTGAATTATATAAATATAAAGTAGTAACAATTGAACCATTAGGAGTAGCAC
     I  G  E  V  N  Y  I  N  I  K  *  *  Q  L  N  H  *  E  *  H
      L  E  K  *  I  I  *  I  *  S  S  N  N  *  T  I  R  S  S  T
    N  W  R  S  E  L  Y  K  Y  K  V  V  T  I  E  P  L  G  V  A 7750      7760      7770      7780      7790      7800
    CCACCAAGGCAAAGAGAAGAGTGGTGCAGAGAGAAAAAAGAGCAGCGATAGGAGCTCTGT
     P  P  R  Q  R  E  E  W  C  R  E  K  K  E  Q  R  *  E  L  C
      H  Q  G  K  E  K  S  G  A  E  R  K  K  S  S  D  R  S  S  V
    S  T  K  A  K  R  R  V  V  Q  R  E  K  R  A  A  I  G  A  L 7810      7820      7830      7840      7850      7860
    TCCTTGGGTTCTTAGGAGCAGCAGGAAGCACTATGGGCGCAGCGTCAGTGACGCTGACGG
     S  L  G  S  *  E  Q  Q  E  A  L  W  A  Q  R  Q  *  R  *  R
      P  W  V  L  R  S  S  R  K  H  Y  G  R  S  V  S  D  A  D  G
    F  L  G  F  L  G  A  A  G  S  T  M  G  A  A  S  V  T  L  T 7870      7880      7890      7900      7910      7920
    TACAGGCCAGACTATTATTGTCTGGTATAGTGCAACAGCAGAACAATTTGCTGAGGGCCA
     Y  R  P  D  Y  Y  C  L  V  *  C  N  S  R  T  I  C  *  G  P
      T  G  Q  T  I  I  V  W  Y  S  A  T  A  E  Q  F  A  E  G  H
    V  Q  A  R  L  L  L  S  G  I  V  Q  Q  Q  N  N  L  L  R  A 7930      7940      7950      7960      7970      7980
    TTGAGGCGCAACAGCATATGTTGCAACTCACAGTCTGGGGCATCAAGCAGCTCCAGGCAA
     L  R  R  N  S  I  C  C  N  S  Q  S  G  A  S  S  S  S  R  Q
      *  G  A  T  A  Y  V  A  T  H  S  L  G  H  Q  A  A  P  G  K
    I  E  A  Q  Q  H  M  L  Q  L  T  V  W  G  I  K  Q  L  Q  A 7990      8000      8010      8020      8030      8040
    GAATCCTGGCTGTGGAAAGATACCTAAAGGATCAACAGCTCCTGGGGATTTGGGGTTGCT
     E  S  W  L  W  K  D  T  *  R  I  N  S  S  W  G  F  G  V  A
      N  P  G  C  G  K  I  P  K  G  S  T  A  P  G  D  L  G  L  L
    R  I  L  A  V  E  R  Y  L  K  D  Q  Q  L  L  G  I  W  G  C 8050      8060      8070      8080      8090      8100
    CTGGAAAACTCATTTGCACCACTACTGTGCCTTGGAATGCTAGTTGGAGTAATAAATCTC
     L  E  N  S  F  A  P  L  L  C  L  G  M  L  V  G  V  I  N  L
      W  K  T  H  L  H  H  Y  C  A  L  E  C  *  L  E  *  *  I  S
    S  G  K  L  I  C  T  T  T  V  P  W  N  A  S  W  S  N  K  S
```

Figure 6P

```
        8110       8120       8130       8140       8150       8160
TGGATGATATTTGGAATAACATGACCTGGATGCAGTGGGAAAGAGAAATTGACAATTACA
 W  M  I  F  G  I  T  *  P  G  C  S  G  K  E  K  L  T  I  T
  G  *  Y  L  E  *  H  D  L  D  A  V  G  K  R  N  *  Q  L  H
L  D  D  I  W  N  N  M  T  W  M  Q  W  E  R  E  I  D  N  Y 8170       8180       8190       8200       8210       8220
CAAGCTTAATATACTCATTACTAGAAAAATCGCAAACCCAACAAGAAATGAATGAACAAG
 Q  A  *  Y  T  H  Y  *  K  N  R  K  P  N  K  K  *  M  N  K
  K  L  N  I  L  I  T  R  K  I  A  N  P  T  R  N  E  *  T  R
T  S  L  I  Y  S  L  L  E  K  S  Q  T  Q  Q  E  M  N  E  Q 8230       8240       8250       8260       8270       8280
AATTATTGGAATTGGATAAATGGGCAAGTTTGTGGAATTGGTTTGACATAACAAATTGGC
 N  Y  W  N  W  I  N  G  Q  V  C  G  I  G  L  T  *  Q  I  G
  I  I  G  I  G  *  M  G  K  F  V  E  L  V  *  H  N  K  L  A
E  L  L  E  L  D  K  W  A  S  L  W  N  W  F  D  I  T  N  W 8290       8300       8310       8320       8330       8340
TGTGGTATATAAAAATATTCATAATGATAGTAGGAGGCTTGGTAGGTTTAAGAATAGTTT
 C  G  I  *  K  Y  S  *  *  *  *  E  A  W  *  V  *  E  *  F
  V  V  Y  K  N  I  H  N  D  S  R  R  L  G  R  F  K  N  S  F
L  W  Y  I  K  I  F  I  M  I  V  G  G  L  V  G  L  R  I  V 8350       8360       8370       8380       8390       8400
TTGCTGTACTTTCTATAGTGAATAGAGTTAGGCAGGGATACTCACCATTGTCGTTGCAGA
 L  L  Y  F  L  *  *  I  E  L  G  R  D  T  H  H  C  R  C  R
  C  C  T  F  Y  S  E  *  S  *  A  G  I  L  T  I  V  V  A  D
F  A  V  L  S  I  V  N  R  V  R  Q  G  Y  S  P  L  S  L  Q 8410       8420       8430       8440       8450       8460
CCCGCCCCCCAGTTCCGAGGGGACCCGACAGGCCCGAAGGAATCGAAGAAGAAGGTGGAG
 P  A  P  Q  F  R  G  D  P  T  G  P  K  E  S  K  K  K  V  E
  P  P  P  S  S  E  G  T  R  Q  A  R  R  N  R  R  R  R  W  R
T  R  P  P  V  P  R  G  P  D  R  P  E  G  I  E  E  E  G  G 8470       8480       8490       8500       8510       8520
AGAGAGACAGAGACACATCCGGTCGATTAGTGCATGGATTCTTAGCAATTATCTGGGTCG
 R  E  T  E  T  H  P  V  D  *  C  M  D  S  *  Q  L  S  G  S
  E  R  Q  R  H  I  R  S  I  S  A  W  I  L  S  N  Y  L  G  R
E  R  D  R  D  T  S  G  R  L  V  H  G  F  L  A  I  I  W  V 8530       8540       8550       8560       8570       8580
ACCTGCGGAGCCTGTTCCTCTTCAGCTACCACCACTTGAGAGACTTACTCTTGATTGCAG
 T  C  G  A  C  S  S  S  A  T  T  T  *  E  T  Y  S  *  L  Q
  P  A  E  P  V  P  L  Q  L  P  P  L  E  R  L  T  L  D  C  S
D  L  R  S  L  F  L  F  S  Y  H  H  L  R  D  L  L  L  I  A 8590       8600       8610       8620       8630       8640
CGAGGATTGTGGAACTTCTGGGACGCAGGGGGTGGGAAGTCCTCAAATATTGGTGGAATC
 R  G  L  W  N  F  W  D  A  G  G  G  K  S  S  N  I  G  G  I
  E  D  C  G  T  S  G  T  Q  G  V  G  S  P  Q  I  L  V  E  S
A  R  I  V  E  L  L  G  R  R  G  W  E  V  L  K  Y  W  W  N
```

Figure 6Q

```
       8650      8660      8670      8680      8690      8700
TCCTACAGTATTGGAGTCAGGAACTAAAGAGTAGTGCTGTTAGCTTGCTTAATGCCACAG
  S  Y  S  I  G  V  R  N  *  R  V  V  L  L  A  C  L  M  P  Q
 P  T  V  L  E  S  G  T  K  E  *  C  C  *  L  A  *  C  H  R
L  L  Q  Y  W  S  Q  E  L  K  S  S  A  V  S  L  L  N  A  T 8710      8720      8730      8740      8750      8760
ATATAGCAGTAGCTGAGGGGACAGATAGGGTTATAGAAGTACTGCAAAGAGCTGGTAGAG
  I  *  Q  *  L  R  G  Q  I  G  L  *  K  Y  C  K  E  L  V  E
 Y  S  S  S  *  G  D  R  *  G  Y  R  S  T  A  K  S  W  *  S
D  I  A  V  A  E  G  T  D  R  V  I  E  V  L  Q  R  A  G  R 8770      8780      8790      8800      8810      8820
CTATTCTCCACATACCTACAAGAATAAGACAGGGCTTGGAAAGGGCTTTGCTATAAGATG
  L  F  S  T  Y  L  Q  E  *  D  R  A  W  K  G  L  C  Y  K  M
 Y  S  P  H  T  Y  K  N  K  T  G  L  G  K  G  F  A  I  R  W
A  I  L  H  I  P  T  R  I  R  Q  G  L  E  R  A  L  L  *  D 8830      8840      8850      8860      8870      8880
GGTGGCAAATGGTCAAAACGTGTGACTGGATGGCCTACTGTAAGGGAAAAAATGAGACGA
  G  G  K  W  S  K  R  V  T  G  W  P  T  V  R  E  K  M  R  R
 V  A  N  G  Q  N  V  *  L  D  G  L  L  *  G  K  K  *  D  E
G  W  Q  M  V  K  T  C  D  W  M  A  Y  C  K  G  K  N  E  T 8890      8900      8910      8920      8930      8940
GCTGAACCAGCTGAGCCAGCAGCAGATGGGGTGGGAGCAGCATCCCGAGACCTGGAAAAA
  A  E  P  A  E  P  A  A  D  G  V  G  A  A  S  R  D  L  E  K
 L  N  Q  L  S  Q  Q  Q  M  G  W  E  Q  H  P  E  T  W  K  N
S  *  T  S  *  A  S  S  R  W  G  G  S  S  I  P  R  P  G  K 8950      8960      8970      8980      8990      9000
CATGGAGCACTCACAAGTAGCAATACAGCAGCTACCAATGCTGATTGTGCCTGGCTAGAA
  H  G  A  L  T  S  S  N  T  A  A  T  N  A  D  C  A  W  L  E
 M  E  H  S  Q  V  A  I  Q  Q  L  P  M  L  I  V  P  G  *  K
T  W  S  T  H  K  *  Q  Y  S  S  Y  Q  C  *  L  C  L  A  R 9010      9020      9030      9040      9050      9060
GCACAAGAGGAGGAGGAAGTGGGTTTTCCAGTCAGACCTCAGGTACCTTTAAGACCAATG
  A  Q  E  E  E  E  V  G  F  P  V  R  P  Q  V  P  L  R  P  M
 H  K  R  R  R  K  W  V  F  Q  S  D  L  R  Y  L  *  D  Q  *
S  T  R  G  G  G  S  G  F  S  S  Q  T  S  G  T  F  K  T  N 9070      9080      9090      9100      9110      9120
ACTTACAAAGCAGCTTTAGATCTTAGCCACTTTTTAAAAGAAAAGGGGGGACTGGATGGG
  T  Y  K  A  A  L  D  L  S  H  F  L  K  E  K  G  G  L  D  G
 L  T  K  Q  L  *  I  L  A  T  F  *  K  K  R  G  D  W  M  G
D  L  Q  S  S  F  R  S  *  P  L  F  K  R  K  G  G  T  G  W 9130      9140      9150      9160      9170      9180
TTAATTTACTCCCAAAAGAGACAAGACATCCTTGATCTGTGGGTCTACCACACACAAGGC
  L  I  Y  S  Q  K  R  Q  D  I  L  D  L  W  V  Y  H  T  Q  G
 *  F  T  T  P  K  R  D  K  T  S  L  I  C  G  S  T  T  H  K  A
V  N  L  L  P  K  E  T  R  H  P  *  S  V  G  L  P  H  T  R
```

Figure 6R

```
              9190        9200        9210        9220        9230        9240
         TACTTCCCTGATTGGCAGAACTACACACCAGGGCCAGGGATCAGATATCCACTGACCTTT
          Y  F  P  D  W  Q  N  Y  T  P  G  P  G  I  R  Y  P  L  T  F
           T  S  L  I  G  R  T  T  H  Q  G  Q  G  S  D  I  H  *  P  L
         L  L  P  *  L  A  E  L  H  T  R  A  R  D  Q  I  S  T  D  L 9250        9260        9270        9280        9290        9300
         GGATGGTGCTTCAAGCTAGTACCAGTTGAGCCAGAGAAGATAGAAGAGGCCAATAAAGGA
          G  W  C  F  K  L  V  P  V  E  P  E  K  I  E  E  A  N  K  G
           D  G  A  S  S  *  Y  Q  L  S  Q  R  R  *  K  R  P  I  K  E
         W  M  V  L  Q  A  S  T  S  *  A  R  E  D  R  R  G  Q  *  R 9310        9320        9330        9340        9350        9360
         GAGAACAACTGCTTGTTACACCCTATGAGCCAGCATGGGATGGATGACCCGGAGAGAGAA
          E  N  N  C  L  L  H  P  M  S  Q  H  G  M  D  D  P  E  R  E
           R  T  T  A  C  Y  T  L  *  A  S  M  G  W  M  T  R  R  E  K
         R  E  Q  L  L  V  T  P  Y  E  P  A  W  D  G  *  P  G  E  R 9370        9380        9390        9400        9410        9420
         GTGTTAGTGTGGAAGTCTGACAGCCACCTAGCATTTCAGCATTATGCCCGAGAGCTGCAT
          V  L  V  W  K  S  D  S  H  L  A  F  Q  H  Y  A  R  E  L  H
           C  *  C  G  S  L  T  A  T  *  H  F  S  I  M  P  E  S  C  I
         S  V  S  V  E  V  *  Q  P  P  S  I  S  A  L  C  P  R  A  A 9430        9440        9450        9460        9470        9480
         CCGGAGTACTACAAGAACTGCTGACATCGAGCTATCTACAAGGGACTTTCCGCTGGGGAC
          P  E  Y  Y  K  N  C  *  H  R  A  I  Y  K  G  L  S  A  G  D
           R  S  T  T  R  T  A  D  I  E  L  S  T  R  D  F  P  L  G  T
         S  G  V  L  Q  E  L  L  T  S  S  Y  L  Q  G  T  F  R  W  G 9490        9500        9510        9520        9530        9540
         TTTCCAGGGAGGTGTGGCCTGGGCGGGACCGGGGAGTGGCGAGCCCTCAGATGCTGCATA
          F  P  G  R  C  G  L  G  G  T  G  E  W  R  A  L  R  C  C  I
           F  Q  G  G  V  A  W  A  G  P  G  S  G  E  P  S  D  A  A  Y
         L  S  R  E  V  W  P  G  R  D  R  G  V  A  S  P  Q  M  L  H 9550        9560        9570        9580        9590        9600
         TAAGCAGCTGCTTTCTGCCTGTACTGGGTCTCTCTGGTTAGACCAGATCTGAGCCTGGGA
          *  A  A  A  F  C  L  Y  W  V  S  L  V  R  P  D  L  S  L  G
           K  Q  L  L  S  A  C  T  G  S  L  W  L  D  Q  I  *  A  W  E
         I  S  S  C  F  L  P  V  L  G  L  S  G  *  T  R  S  E  P  G 9610        9620        9630        9640        9650        9660
         GCTCTCTGGCTAACTAGGGAACCCACTGCTTAAGCCTCAATAAAGCTTGCCTTGAGTGCT
          A  L  W  L  T  R  E  P  T  A  *  A  S  I  K  L  A  L  S  A
           L  S  G  *  L  G  N  P  L  L  K  P  Q  *  S  L  P  *  V  L
         S  S  L  A  N  *  G  T  H  C  L  S  L  N  K  A  C  L  E  C 9670        9680        9690        9700        9710        9720
         TCAAGTAGTGTGTGCCCGTCTGTTATGTGACTCTGGTAGCTAGAGATCCCTCAGATCCTT
          S  S  S  V  C  P  S  V  M  *  L  W  *  L  E  I  P  Q  I  L
           Q  V  V  C  A  R  L  L  C  D  S  G  S  *  R  S  L  R  S  F
         F  K  *  C  V  P  V  C  Y  V  V  T  L  V  A  R  D  P  S  D  P
```

Figure 6S

```
         9730        9740
TTAGGCAGTGTGGAAAATCTCTAGCA
  L   G   S   V   E   N   L   *
    *   A   V   W   K   I   S   S
  F   R   Q   C   G   K   S   L   A
```

Figure 8A

```
              10         20         30         40         50         60
     GATCAAGGGCCACAGAGGGAGCCACACAATGAATGGACACTAGAGCTTTTAGAGGAGCTT
       D  Q  G  P  Q  R  E  P  H  N  E  W  T  L  E  L  L  E  E  L
        I  K  G  H  R  G  S  H  T  M  N  G  H  *  S  F  *  R  S  L
         S  R  A  T  E  G  A  T  Q  *  M  D  T  R  A  F  R  G  A 70         80         90        100        110        120
     AAGAGTGAAGCTGTTAGACACTTTCCTAGGATATGGCTTCATGGCTTAGGGCAACATATC
       K  S  E  A  V  R  H  F  P  R  I  W  L  H  G  L  G  Q  H  I
        R  V  K  L  L  D  T  F  L  G  Y  G  F  M  A  *  G  N  I  S
         *  E  *  S  C  *  T  L  S  *  D  M  A  S  W  L  R  A  T  Y 130        140        150        160        170        180
     TATGAAACTTATGGGGATACTTGGGCAGGAGTGGAAGCCATAATAAGAATTCTGCAACAA
       Y  E  T  Y  G  D  T  W  A  G  V  E  A  I  I  R  I  L  Q  Q
        M  K  L  M  G  I  L  G  Q  E  W  K  P  *  *  E  F  C  N  N
         L  *  N  L  W  G  Y  L  G  R  S  G  S  H  N  K  N  S  A  T 190        200        210        220        230        240
     CTGCTGTTTATCCATTTCAGGATTGGGTGCCAACATAGCAGAATAGGTATTATTCAACAG
       L  L  F  I  H  F  R  I  G  C  Q  H  S  R  I  G  I  I  Q  Q
        C  C  L  S  I  S  G  L  G  A  N  I  A  E  *  V  L  F  N  R
         T  A  V  Y  P  F  Q  D  W  V  P  T  *  Q  N  R  Y  Y  S  T 250        260        270        280        290        300
     AGGAGAGCAAGAAATGGAGCCAGTAGATCCTAAACTAGAGCCCTGGAAGCATCCAGGAAG
       R  R  A  R  N  G  A  S  R  S  *  T  R  A  L  E  A  S  R  K
        G  E  Q  E  M  E  P  V  D  P  K  L  E  P  W  K  H  P  G  S
         E  E  S  K  K  W  S  Q  *  I  L  N  *  S  P  G  S  I  Q  E 310        320        330        340        350        360
     TCAGCCTAAGACTGCTTGTACCACTTGCTATTGTAAAAAGTGTTGCTTTCATTGCCAAGT
       S  A  *  D  C  L  Y  H  L  L  *  K  V  L  L  S  L  P  S
        Q  P  K  T  A  C  T  T  C  Y  C  K  K  C  C  F  H  C  Q  V
         V  S  L  R  L  L  V  P  L  A  I  V  K  S  V  A  F  I  A  K 370        380        390        400        410        420
     TTGCTTCATAACAAAAGGCTTAGGCATCTCCTATGGCAGGAAGAAGCGGAGACAGCGACG
       L  L  H  N  K  R  L  R  H  L  L  W  Q  E  E  A  E  T  A  T
        C  F  I  T  K  G  L  G  I  S  Y  G  R  K  K  R  R  Q  R  R
         F  A  S  *  Q  K  A  *  A  S  P  M  A  G  R  S  G  D  S  D
                                              (Rev)
             430        440        450        460        470        480
     AAGAGCTCCTCAAGACAGTGAGACTCATCAAGTTTCTCTATCAAAGCAGTAAGTAGTACA
       K  S  S  S  R  Q  *  D  S  S  S  F  S  I  K  A  V  S  S  T
        R  A  P  Q  D  S  E  T  H  Q  V  S  L  S  K  Q  *  V  V  H
         E  E  L  L  K  T  V  R  L  I  K  F  L  Y  Q  S  S  K  *  Y 490        500        510        520        530        540
     TGTAATGCAAGCTTTACAAATATCAGCTATAGTAGGATTAGTAGTAGCAGCAATAATAGC
       C  N  A  S  F  T  N  I  S  Y  S  R  I  S  S  S  S  N  N  S
        V  M  Q  A  L  Q  I  S  A  I  V  G  L  V  V  A  A  I  I  A
         M  *  C  K  L  Y  K  Y  Q  L  *  *  D  *  *  *  Q  Q  *  *
```

Figure 8B

```
           550        560        570        580        590        600
    AATAGTTGTGTGGACCATAGTATTCATAGAATATAGGAAAATATTAAGGCAAAGAAAAAT
      N  S  C  V  D  H  S  I  H  R  I  *  E  N  I  K  A  K  K  N
       I  V  V  W  T  I  V  F  I  E  Y  R  K  I  L  R  Q  R  K  I
        Q  *  L  C  G  P  *  Y  S  *  N  I  G  K  Y  *  G  K  E  K 610        620        630        640        650        660
    AGACAGGTTAATTGATAGAATAACAGAAAGAGCAGAAGACAGTGGCAATGAGAGTGACGG
      R  Q  V  N  *  *  N  N  R  K  S  R  R  Q  W  Q  *  E  *  R
       D  R  L  I  D  R  I  T  E  R  A  E  D  S  G  N  E  S  D  G
        *  T  G  *  L  I  E  *  Q  K  E  Q  K  T  V  A  M  R  V  T
                                                         (Env)
           670        680        690        700        710        720
    AGATCAGGAAGAGTTATCAGCACTGGTGGAGATGGGGCATCATGCTCCTTGGGATATTAA
      R  S  G  R  V  I  S  T  G  G  D  G  A  S  C  S  L  G  Y  *
       D  Q  E  E  L  S  A  L  V  E  M  G  H  H  A  P  W  D  I  N
        E  I  R  K  S  Y  Q  H  W  W  R  W  G  I  M  L  L  G  I  L 730        740        750        760        770        780
    TGATCTGTAATGCTGAAGAAAAATTGTGGGTCACAGTCTATTATGGGGTACCTGTGTGGA
      *  S  V  M  L  K  K  N  C  G  S  Q  S  I  M  G  Y  L  C  G
       D  L  *  C  *  R  K  I  V  G  H  S  L  L  W  G  T  C  V  E
        M  I  C  N  A  E  E  K  L  W  V  T  V  Y  Y  G  V  P  V  W 790        800        810        820        830        840
    AAGAAGCAACCACCACTCTATTTTGTGCATCAGATCGTAAAGCATATGATACAGAGGTAC
      K  K  Q  P  P  L  Y  F  V  H  Q  I  V  K  H  M  I  Q  R  Y
       R  S  N  H  H  S  I  L  C  I  R  S  *  S  I  *  Y  R  G  T
        K  E  A  T  T  T  L  F  C  A  S  D  R  K  A  Y  D  T  E  V 850        860        870        880        890        900
    ATAATGTTTGGGCCACACATGCCTGTGTACCCACAGACCCCAACCCACAAGAAGTAGAAT
      I  M  F  G  P  H  M  P  V  Y  P  Q  T  P  T  H  K  K  *  N
       *  C  L  G  H  T  C  L  C  T  H  R  P  Q  P  T  R  S  R  I
        H  N  V  W  A  T  H  A  C  V  P  T  D  P  N  P  Q  E  V  E 910        920        930        940        950        960
    TGAAAAATGTGACAGAAAATTTTAACATGTGGAAAAATAACATGGTAGAACAAATGCATG
      *  K  M  *  Q  K  I  L  T  C  G  K  I  T  W  *  N  K  C  M
       E  K  C  D  R  K  F  *  H  V  E  K  *  H  G  R  T  N  A  *
        L  K  N  V  T  E  N  F  N  M  W  K  N  N  M  V  E  Q  M  H 970        980        990       1000       1010       1020
    AGGATATAATCAGTTTATGGGATCAAAGCCTAAAGCCATGTGTAAAATTAACCCCACTCT
      R  I  *  S  V  Y  G  I  K  A  *  S  H  V  *  N  *  P  H  S
       G  Y  N  Q  F  M  G  S  K  P  K  A  M  C  K  I  N  P  T  L
        E  D  I  I  S  L  W  D  Q  S  L  K  P  C  V  K  L  T  P  L 1030       1040       1050       1060       1070       1080
    GTGTTACTTTAAATTGCACTGATTTGAGGAATGCTACTAATGGGAATGACACTAATACCA
      V  L  L  *  I  A  L  I  *  G  M  L  L  M  G  M  T  L  I  P
       C  Y  F  K  L  H  *  F  E  E  C  Y  *  W  E  *  H  *  Y  H
        C  V  T  L  N  C  T  D  L  R  N  A  T  N  G  N  D  T  N  T
```

Figure 8C

```
          1090      1100      1110      1120      1130      1140
     CTAGTAGTAGCAGGGGAATGGTGGGGGGAGGAGAAATGAAAAATTGCTCTTTCAATATCA
       L  V  V  A  G  E  W  W  G  E  E  K  *  K  I  A  L  S  I  S
         *  *  *  Q  G  N  G  G  G  R  R  N  E  K  L  L  F  Q  Y  H
     T  S  S  S  R  G  M  V  G  G  G  E  M  K  N  C  S  F  N  I 1150      1160      1170      1180      1190      1200
     CCACAAACATAAGAGGTAAGGTGCAGAAAGAATATGCACTTTTTTATAAACTTGATATAG
       P  Q  T  *  E  V  R  C  R  K  N  M  H  F  F  I  N  L  I  *
         H  K  H  K  R  *  G  A  E  R  I  C  T  F  L  *  T  *  Y  S
     T  T  N  I  R  G  K  V  Q  K  E  Y  A  L  F  Y  K  L  D  I 1210      1220      1230      1240      1250      1260
     CACCAATAGATAATAATAGTAATAATAGATATAGGTTGATAAGTTGTAACACCTCAGTCA
       H  Q  *  I  I  I  V  I  I  D  I  G  *  *  V  V  T  P  Q  S
         T  N  R  *  *  *  *  *  *  I  *  V  D  K  L  *  H  L  S  H
     A  P  I  D  N  N  S  N  N  R  Y  R  L  I  S  C  N  T  S  V 1270      1280      1290      1300      1310      1320
     TTACACAGGCCTGTCCAAAGGTATCCTTTGAGCCAATTCCCATACATTATTGTGCCCCGG
       L  H  R  P  V  Q  R  Y  P  L  S  Q  F  P  Y  I  I  V  P  R
         Y  T  G  L  S  K  G  I  L  *  A  N  S  H  T  L  L  C  P  G
     I  T  Q  A  C  P  K  V  S  F  E  P  I  P  I  H  Y  C  A  P 1330      1340      1350      1360      1370      1380
     CTGGTTTTGCGATTCTAAAGTGTAAAGATAAGAAGTTCAATGGAAAAGGACCATGTACAA
       L  V  L  R  F  *  S  V  K  I  R  S  S  M  E  K  D  H  V  Q
         W  F  C  D  S  K  V  *  R  *  E  V  Q  W  K  R  T  M  Y  K
     A  G  F  A  I  L  K  C  K  D  K  K  F  N  G  K  G  P  C  T 1390      1400      1410      1420      1430      1440
     ATGTCAGCACAGTACAATGTACACATGGAATTAGGCCAGTAGTATCAACTCAACTGCTGT
       M  S  A  Q  Y  N  V  H  M  E  L  G  Q  *  Y  Q  L  N  C  C
         C  Q  H  S  T  M  Y  T  W  N  *  A  S  S  I  N  S  T  A  V
     N  V  S  T  V  Q  C  T  H  G  I  R  P  V  V  S  T  Q  L  L 1450      1460      1470      1480      1490      1500
     TAAATGGCAGTCTAGCAGAAGAAGAGGTAGTAATTAGATCCGCCAATTTCGCGGACAATG
       *  M  A  V  *  Q  K  K  R  *  *  L  D  P  P  I  S  R  T  M
         K  W  Q  S  S  R  R  R  G  S  N  *  I  R  Q  F  R  G  Q  C
     L  N  G  S  L  A  E  E  E  V  V  I  R  S  A  N  F  A  D  N 1510      1520      1530      1540      1550      1560
     CTAAAGTCATAATAGTACAGCTGAATGAATCTGTAGAAATTAATTGTACAAGACCCAACA
       L  K  S  *  *  Y  S  *  M  N  L  *  K  L  I  V  Q  D  P  T
         *  S  H  N  S  T  A  E  *  I  C  R  N  *  L  Y  K  T  Q  Q
     A  K  V  I  I  V  Q  L  N  E  S  V  E  I  N  C  T  R  P  N 1570      1580      1590      1600      1610      1620
     ACAATACAAGAAAAAGTATACATATAGGACCAGGCAGAGCATTTTATACAACAGGAGAAA
       T  I  Q  E  K  V  Y  I  *  D  Q  A  E  H  F  I  Q  Q  E  K
         Q  Y  K  K  K  Y  T  Y  R  T  R  Q  S  I  L  Y  N  R  R  N
     N  N  T  R  K  S  I  H  I  G  P  G  R  A  F  Y  T  T  G  E
```

Figure 8D

```
            1630       1640       1650       1660       1670       1680
       TAATAGGAGATATAAGACAAGCACATTGTAACCTTAGTAGAGCAAAATGGAATGACACTT
        *  *  E  I  *  D  K  H  I  V  T  L  V  E  Q  N  G  M  T  L
          N  R  R  Y  K  T  S  T  L  *  P  *  *  S  K  M  E  *  H  F
         I  I  G  D  I  R  Q  A  H  C  N  L  S  R  A  K  W  N  D  T 1690       1700       1710       1720       1730       1740
       TAAATAAGATAGTTATAAAATTAAGAGAACAATTTGGGAATAAAACAATAGTCTTTAAGC
        *  I  R  *  L  *  N  *  E  N  N  L  G  I  K  Q  *  S  L  S
          K  *  D  S  Y  K  I  K  R  T  I  W  E  *  N  N  S  L  *  A
         L  N  K  I  V  I  K  L  R  E  Q  F  G  N  K  T  I  V  F  K 1750       1760       1770       1780       1790       1800
       ACTCCTCAGGAGGGGACCCAGAAATTGTGACGCACAGTTTTAATTGTGGAGGGGAATTTT
        T  P  Q  E  G  T  Q  K  L  *  R  T  V  L  I  V  E  G  N  F
          L  L  R  R  G  P  R  N  C  D  A  Q  F  *  L  W  R  G  I  F
         H  S  S  G  G  D  P  E  I  V  T  H  S  F  N  C  G  G  E  F 1810       1820       1830       1840       1850       1860
       TCTACTGTAATTCAACACAACTGTTTAATAGTACTTGGAATGTTACTGAAGAGTCAAATA
        S  T  V  I  Q  H  N  C  L  I  V  L  G  M  L  L  K  S  Q  I
          L  L  *  F  N  T  T  V  *  *  Y  L  E  C  Y  *  R  V  K  *
         F  Y  C  N  S  T  Q  L  F  N  S  T  W  N  V  T  E  E  S  N 1870       1880       1890       1900       1910       1920
       ACACTGTAGAAAATAACACAATCACACTCCCATGCAGAATAAAACAAATTATAAACATGT
        T  L  *  K  I  T  Q  S  H  S  H  A  E  *  N  K  L  *  T  C
          H  C  R  K  *  H  N  H  T  P  M  Q  N  K  T  N  Y  K  H  V
         N  T  V  E  N  N  T  I  T  L  P  C  R  I  K  Q  I  I  N  M 1930       1940       1950       1960       1970       1980
       GGCAGGAAGTAGGAAGAGCAATGTATGCCCCTCCCATCAGAGGACAAATTAGATGTTCAT
        G  R  K  *  E  E  Q  C  M  P  L  P  S  E  D  K  L  D  V  H
          A  G  S  R  K  S  N  V  C  P  S  H  Q  R  T  N  *  M  F  I
         W  Q  E  V  G  R  A  M  Y  A  P  P  I  R  G  Q  I  R  C  S 1990       2000       2010       2020       2030       2040
       CAAATATTACAGGGCTGCTATTAACAAGAGATGGTGGTCCTGAGGACAACAAGACCGAGG
        Q  I  L  Q  G  C  Y  *  Q  E  M  V  V  L  R  T  T  R  P  R
          K  Y  Y  R  A  A  I  N  K  R  W  W  S  *  G  Q  Q  D  R  G
         S  N  I  T  G  L  L  L  T  R  D  G  G  P  E  D  N  K  T  E 2050       2060       2070       2080       2090       2100
       TCTTCAGACCTGGAGGAGGAGATATGAGGGATAATTGGAGAAGTGAATTATATAAATATA
        S  S  D  L  E  E  E  I  *  G  I  I  G  E  V  N  Y  I  N  I
          L  Q  T  W  R  R  R  Y  E  G  *  L  E  K  *  I  I  *  I  *
         V  F  R  P  G  G  G  D  M  R  D  N  W  R  S  E  L  Y  K  Y 2110       2120       2130       2140       2150       2160
       AAGTAGTAAAAATTGAACCATTAGGAGTAGCACCCACCAAGGCAAAGAGAAGAGTGGTGC
        K  *  *  K  L  N  H  *  E  *  H  P  P  R  Q  R  E  E  W  C
          S  S  K  N  *  T  I  R  S  S  T  H  Q  G  K  E  K  S  G  A
         K  V  V  K  I  E  P  L  G  V  A  P  T  K  A  K  R  R  V  V
```

Figure 8E

```
           2170      2180      2190      2200      2210      2220
       AGAGAGAAAAAGAGCAGTGGGAATAGGAGCTGTGTTCCTTGGGTTCTTGGGAGCAGCAG
         R  E  K  K  E  Q  W  E  *  E  L  C  S  L  G  S  W  E  Q  Q
          E  R  K  K  S  S  G  N  R  S  C  V  P  W  V  L  G  S  S  R
           Q  R  E  K  R  A  V  G  I  G  A  V  F  L  G  F  L  G  A  A 2230      2240      2250      2260      2270      2280
       GAAGCACTATGGGCGCAGCGGCAATGACGCTGACGGTACAGGCCAGACTATTATTGTCTG
         E  A  L  W  A  Q  R  Q  *  R  *  R  Y  R  P  D  Y  Y  C  L
          K  H  Y  G  R  S  G  N  D  A  D  G  T  G  Q  T  I  I  V
           G  S  T  M  G  A  A  A  M  T  L  T  V  Q  A  R  L  L  L  S 2290      2300      2310      2320      2330      2340
       GTATAGTGCAACAGCAGAACAATCTGCTGAGGGCTATTGAGGCGCAACAGCATCTGTTGC
         V  *  C  N  S  R  T  I  C  *  G  L  L  R  R  N  S  I  C  C
          Y  S  A  T  A  E  Q  S  A  E  G  Y  *  G  A  T  A  S  V  A
           G  I  V  Q  Q  Q  N  N  L  L  R  A  I  E  A  Q  Q  H  L  L 2350      2360      2370      2380      2390      2400
       AACTCACAGTCTGGGGCATCAAGCAGCTCCAGGCAAGAGTCCTGGCTGTGGAAAGATACC
         N  S  Q  S  G  A  S  S  S  S  R  Q  E  S  W  L  W  K  D  T
          T  H  S  L  G  H  Q  A  A  P  G  K  S  P  G  C  G  K  I  P
           Q  L  T  V  W  G  I  K  Q  L  Q  A  R  V  L  A  V  E  R  Y 2410      2420      2430      2440      2450      2460
       TAAGGGATCAACAGCTCCTGGGGATTTGGGGTTGCTCTGGAAAACTCATCTGCACCACTG
         *  G  I  N  S  S  W  G  F  G  V  A  L  E  N  S  S  A  P  L
          K  G  S  T  A  P  G  D  L  G  L  L  W  K  T  H  L  H  H  C
           L  R  D  Q  Q  L  L  G  I  W  G  C  S  G  K  L  I  C  T  T 2470      2480      2490      2500      2510      2520
       CTGTGCCTTGGAATGCTAGTTGGAGTAATAAATCTCTGAATAAGATTTGGGATAACATGA
         L  C  L  G  M  L  V  G  V  I  N  L  *  I  R  F  G  I  T  *
          C  A  L  E  C  *  L  E  *  *  I  S  E  *  D  L  G  *  H  D
           A  V  P  W  N  A  S  W  S  N  K  S  L  N  K  I  W  D  N  M 2530      2540      2550      2560      2570      2580
       CCTGGATAGAGTGGGACAGAGAAATTAACAATTACACAAGCATAATATACAGCTTAATTG
         P  G  *  S  G  T  E  K  L  T  I  T  Q  A  *  Y  T  A  *  L
          L  D  R  V  G  Q  R  N  *  Q  L  H  K  H  N  I  Q  L  N  *
           T  W  I  E  W  D  R  E  I  N  N  Y  T  S  I  I  Y  S  L  I 2590      2600      2610      2620      2630      2640
       AAGAATCGCAGAACCAACAAGAAAAGAATGAACAAGAATTATTAGAATTAGATAAATGGG
         K  N  R  R  T  N  K  K  R  M  N  K  N  Y  *  N  *  I  N  G
          R  I  A  E  P  T  R  K  E  *  T  R  I  I  R  I  R  *  M  G
           E  E  S  Q  N  Q  Q  E  K  N  E  Q  E  L  L  E  L  D  K  W 2650      2660      2670      2680      2690      2700
       CAAGTTTGTGGAATTGGTTTGACATAACAAAATGGCTGTGGTATATAAAAATATTCATAA
         Q  V  C  G  I  G  L  T  *  Q  N  G  C  G  I  *  K  Y  S  *
          K  F  V  E  L  V  *  H  N  K  M  A  V  V  Y  K  N  I  H  N
           A  S  L  W  N  W  F  D  I  T  K  W  L  W  Y  I  K  I  F  I
```

Figure 8F

```
         2710       2720       2730       2740       2750       2760
    TGATAGTAGGAGGCTTGATAGGTTTAAGAATAGTTTTTTCTGTACTTTCTATAGTGAATA
      *  *  *  E  A  *  *  V  *  E  *  F  F  L  Y  F  L  *  *  I
       D  S  R  R  L  D  R  F  K  N  S  F  F  C  T  F  Y  S  E  *
       M  I  V  G  G  L  I  G  L  R  I  V  F  S  V  L  S  I  V  N 2770       2780       2790       2800       2810       2820
    GAGTTAGGCAGGGATACTCACCATTATCGTTTCAGACCCACCTCCCATCCTCGAGGGGAC
       E  L  G  R  D  T  H  H  Y  R  F  R  P  T  S  H  P  R  G  D
        S  *  A  G  I  L  T  I  I  V  S  D  P  P  P  I  L  E  G  T  (Rev)
       R  V  R  Q  G  Y  S  P  L  S  F  Q  T  H  L  P  S  S  R  G  (Env)

2830       2840       2850       2860       2870       2880
    CCGACAGGCCCGGAGGAATCGAAGAAGAAGGTGGAGAGAGAGACAGAGACAGATCCGGTC
       P  T  G  P  E  E  S  K  K  K  V  E  R  E  T  E  T  D  P  V
        R  Q  A  R  R  N  R  R  R  R  W  R  E  R  Q  R  Q  I  R  S
       P  D  R  P  G  G  I  E  E  E  G  G  E  R  D  R  D  R  S  G 2890       2900       2910       2920       2930       2940
    CATTAGTGAACGGATTCTTGGCGCTTATCTGGGTCGATCTGCGGAGCCTGTTCCTCTTCA
       H  *  *  T  D  S  W  R  L  S  G  S  I  C  G  A  C  S  S  S
        I  S  E  R  I  L  G  A  Y  L  G  R  S  A  E  P  V  P  L  Q
       P  L  V  N  G  F  L  A  I  W  V  D  L  R  S  L  F  L  F 2950       2960       2970       2980       2990       3000
    GCTACCACCGCTTGAGAGACTTACTCTTGATTGTGATGAGGATTGTGGAACTTCTGGGAC
       A  T  T  A  *  E  T  Y  S  *  L  *  *  G  L  W  N  F  W  D
        L  P  P  L  E  R  L  T  L  D  C  D  E  D  C  G  T  S  G  T
       S  Y  H  R  L  R  D  L  L  L  I  V  M  R  I  V  E  L  L  G 3010       3020       3030       3040       3050       3060
    TAGCAGGGGGGTGGGAAGTCCTCAAATATTGGTGGAATCTCCTACAGTATTGGAGTCAGG
       *  Q  G  G  G  K  S  S  N  I  G  G  I  S  Y  S  I  G  V  R
        S  R  G  V  G  S  P  Q  I  L  V  E  S  P  T  V  L  E  S  G
       L  A  G  G  W  E  V  L  K  Y  W  W  N  L  L  Q  Y  W  S  Q 3070       3080       3090       3100       3110       3120
    AACTAAAGAATAGTGCTGTTAGCTTGCTCAATGCCACAGCTGTAGCAGTAGCTGAAGGGA
       N  *  R  I  V  L  L  A  C  S  M  P  Q  L  *  Q  *  L  K  G
        T  K  E  *  C  C  *  L  A  Q  C  H  S  C  S  S  *  R  D
       E  L  K  N  S  A  V  S  L  L  N  A  T  A  V  A  V  A  E  G 3130       3140       3150       3160       3170       3180
    CAGATAGGGTTATAGAAGTATTACAGAGAGCTGTTAGAGCTATTCTCCACATACCTAGAA
       Q  I  G  L  *  K  Y  Y  R  E  L  L  E  L  F  S  T  Y  L  E
        R  *  G  Y  R  S  I  T  E  S  C  *  S  Y  S  P  H  T  *  K
       T  D  R  V  I  E  V  L  Q  R  A  V  R  A  I  L  H  I  P  R 3190       3200       3210       3220       3230       3240
    GAATAAGACAGGGCTTGGAAAGGGCTTTGCTATAAGATGGGTGGCAAGTGGTCAAAAAGT
       E  *  D  R  A  W  K  G  L  C  Y  K  M  G  G  K  W  S  K  S
        N  K  T  G  L  G  K  G  F  A  I  R  W  V  A  S  G  Q  K  V
       R  I  R  Q  G  L  E  R  A  L  L  *  D  G  W  Q  V  V  K  K
```

Figure 8G

```
        3250       3260       3270       3280       3290       3300
AGTATAGTCGTATGGCCTGCTGTAAGGAAAAGAATGAGAAGAACTGAGCCAGCAGCAGAT
  S  I  V  V  W  P  A  V  R  K  R  M  R  R  T  E  P  A  A  D
   V  *  S  Y  G  L  L  *  G  K  E  *  E  E  L  S  Q  Q  Q  M
 *  Y  S  R  M  A  C  C  K  E  K  N  E  K  N  *  A  S  S  R 3310       3320       3330       3340       3350       3360
GGAGTAGGAGCAGTATCTAGAGACCTGGAAAAACATGGAGCAATCACAAGTAGCAATACA
  G  V  G  A  V  S  R  D  L  E  K  H  G  A  I  T  S  S  N  T
   E  *  E  Q  Y  L  E  T  W  K  N  M  E  Q  S  Q  V  A  I  Q
 W  S  R  S  S  I  *  R  P  G  K  T  W  S  N  H  K  *  Q  Y 3370       3380       3390       3400       3410       3420
GCAGCTAACAATGCTGATTGTGCCTGGCTAGAAGCACAAGAGGATGAAGAAGTGGGTTTT
  A  A  N  N  A  D  C  A  W  L  E  A  Q  E  D  E  E  V  G  F
   Q  L  T  M  L  I  V  P  G  *  K  H  K  R  M  K  K  W  V  F
 S  S  *  Q  C  *  L  C  L  A  R  S  T  R  G  *  R  S  G  F 3430       3440       3450       3460       3470       3480
CCAGTCAGACCTCAGGTACCTTTAAGACCAATGACTCGCAGTGCAGCTATAGATCTTAGC
  P  V  R  P  Q  V  P  L  R  P  M  T  R  S  A  A  I  D  L  S
   Q  S  D  L  R  Y  L  *  D  Q  *  L  A  V  Q  L  *  I  L  A
 S  S  Q  T  S  G  T  F  K  T  N  D  S  Q  C  S  Y  R  S  *

3490       3500       3510       3520       3530       3540
CACTTTTTTAAGAAAAAGGGGGGACTGGAAGGGCTAATTCACTCCCAAAAAAGACAAGAT
  H  F  F  K  K  K  G  G  L  E  G  L  I  H  S  Q  K  R  Q  D
   T  F  L  R  K  R  G  D  W  K  G  *  F  T  P  K  K  D  K  I
 P  L  F  *  E  K  G  G  T  G  R  A  N  S  L  P  K  K  T  R 3550       3560       3570       3580       3590       3600
ATCCTTGATTTGTGGGTCTACCACACACAAGGCTACTTCCCTGATTGGCAGAACTACACA
  I  L  D  L  W  V  Y  H  T  Q  G  Y  F  P  D  W  Q  N  Y  T
   S  L  I  C  G  S  T  T  H  K  A  T  S  L  I  G  R  T  T  H
 Y  P  *  F  V  G  L  P  H  T  R  L  L  P  *  L  A  E  L  H 3610       3620       3630       3640       3650       3660
CCAGGGCCAGGGACCAGATTTCCACTGACCTTTGGATGGTGCTTCAAGCTAGTACCAGTT
  P  G  P  G  T  R  F  P  L  T  F  G  W  C  F  K  L  V  P  V
   Q  G  Q  G  P  D  F  H  *  P  L  D  G  A  S  S  *  Y  Q  L
 T  R  A  R  D  Q  I  S  T  D  L  W  M  V  L  Q  A  S  T  S 3670       3680       3690       3700       3710       3720
GAGCCAGAGAAGGTAGAAGAGGCCAATGAAGGAGAGAACAACTGCTTGTCACACCCTATG
  E  P  E  K  V  E  E  A  N  E  G  E  N  N  C  L  S  H  P  M
   S  Q  R  R  *  K  R  P  M  K  E  R  T  T  A  C  H  T  L  *
 *  A  R  E  G  R  R  G  Q  *  R  R  E  Q  L  L  V  T  P  Y 3730       3740       3750       3760       3770       3780
AGCCTGCATGGGATGGATGACCCGGAGAAAGAAGTGTTAGCATGGAAGTTTGACAGCAGC
  S  L  H  G  M  D  D  P  E  K  E  V  L  A  W  K  F  D  S  S
   A  C  M  G  W  M  T  R  R  K  K  C  *  H  G  S  L  T  A  A
 E  P  A  W  D  G  *  P  G  E  R  S  V  S  M  E  V  *  Q  Q
```

Figure 8H

```
      3790        3800
CTAGCATTCCATCACGTGGCCCGAGAA
  L  A  F  H  H  V  A  R  E
   *  H  S  I  T  W  P  E
 P  S  I  P  S  R  G  P  R
```

MOLECULAR CLONES OF HIV-1 VIRAL STRAINS MN-ST1 AND BA-L AND USES THEREOF

This is a continuation of application Ser. No. 07/599,491, filed on Oct. 17, 1990, which was abandoned upon the filing hereof.

BACKGROUND OF THE INVENTION

HIV-1 has been identified as the etiologic agent of the acquired immunodeficiency syndrome (AIDS) (Barre-Sinoussi et al., Science 220, 868–871, 1983; Popvic et al, Science 224, 497–500, 1984; Gallo et al., Science 224, 500–503, 1984). Infected individuals generally develop antibodies to the virus within several months of exposure (Sarngadharan et al., Science 224, 506–508, 1984), which has made possible the development of immunologically based tests which can identify most of blood samples from infected individuals. This is a great advantage in diagnosis, and is vital to maintaining the maximum possible safety of samples from blood banks.

An important aspect of HIV-1 is its genetic variability (Hahn et al., Proc. Natl. Acad. Sci. U.S.A. 82, 4813–4817, 1985). This is particularly evident in the gene for the outer envelope glycoprotein (Starcich et al., Cell 45, 637–648, 1986; Alizon et al., Cell 46, 63–74, 1986; Gurgo et al., Virology 164, 531–536, 1988). Since the outer envelope glycoprotein is on the surface of the virus particle and the infected cell, it is potentially one of the primary targets of the immune system, including the target of neutralizing antibodies and cytotoxic T cells. This variability may also lead to differences in the ability of antigens from different strains of HIV-1 to be recognized by antibodies from a given individual, as well as to differences in the ability of proteins from different strains of virus to elicit an immune response which would be protective against the mixture of virus strains that exists in the at risk populations.

Several biologically active complete molecular clones of various strains of HIV-1 have been obtained and sequenced. These clones, however, seem to represent viral genotypes which are relatively atypical of United States HIV-1 isolates. In addition, several of the translational reading frames for non-structural viral proteins are not complete. Further, viruses derived from these clones do not grow in macrophages, in contrast to many HIV-1 field isolates and, perhaps, because of this lack of ability to infect macrophage efficiently, these clones do not replicate well in chimpanzees. This latter ability is important for testing candidate vaccines in animal systems. In addition, the ability to infect macrophages is critical in evaluating the possible protective efficacy of elicited immune response since neutralization of infectivity on macrophage may differ from the better studied neutralization on T cells.

Neutralizing antibodies (Robert-Guroff et al., Nature 316, 72–74, 1985; Weiss et al., Nature 316, 69–72, 1985) have been demonstrated in infected individuals, as have cytotoxic T cells responses (Walker et al, Nature 328, 345–348, 1988). Although these do not appear to be protective, it is likely that if they were present prior to infection, they would prevent infection, especially by related strains of virus. This is supported by the finding that macaques can be protected by immunization with inactivated simian immunodeficiency virus (SIV) from infection with the homologous live virus (Murphy-Corb et al., Science 246, 1293–1297, 1989). Chimps also have been passively protected against challenge by live virus by prior administration of neutralizing antibodies to the same virus (Emini et al., J. Virol. 64, 3674–3678, 1989). One problem, however, is that at least some of the neutralizing antibodies studied depend on recognition of a variable region on the envelope (Matsushita et al., J. Virol. 62, 2107–2114, 1988; Rusche et al., Proc. Natl. Acad. Sci. U.S.A. 85, 3198–3202, 1988; Skinner et al., AIDS Res. Hum. Retroviruses 4, 187–197, 1988) called the V3 region (Starcich et al., Cell 45, 637–648, 1986).

An at least partial solution to the problem of viral heterogeneity is to identify prototypical HIV-1 strains, that is, those that are most similar by DNA sequence data or serologic reactivity to strains present in the population at risk. The inclusion of a limited number of such prototype strains in a polyvalent vaccine cocktail might then result in elicitation of an immune response protective against most naturally occurring viruses within a given population. Such a mixture should also provide the maximum possible sensitivity in diagnostic tests for antibodies in infected individuals.

Components of highly representative isolates of a geographical area provide the maximum possible sensitivity in diagnostic tests and vaccines. Production of viral proteins from molecular clones by recombinant DNA techniques is the preferred and safest means to provide such proteins. Molecular clones of prototype HIV-1 strains can serve as the material from which such recombinant proteins can be made. The use of recombinant DNA avoids any possibility of the presence of live virus and affords the opportunity of genetically modifying viral gene products. The use of biological active clones ensures that the gene products are functional and hence, maximizes their potential relevance.

Infectious clones, that is, those which after transfection into recipient cells produce complete virus, are desirable for several reasons. One reason is that the gene products are by definition functional; this maximizes their potential relevance to what is occurring in vivo. A second reason is that genetically altered complete virus is easy to obtain. Consequently, the biological consequences of variability can be easily assessed. For example, the effect of changes in the envelope gene on the ability of the virus to be neutralized by antibody can be easily addressed. Using this technique, a single point mutation in the envelope gene has been shown to confer resistance to neutralizing antibody (Reitz et al., Cell 54, 57–63, 1988). A third reason is that a clonal virus population provides the greatest possible definition for challenge virus in animals receiving candidate vaccines, especially those including components of the same molecularly cloned virus.

SUMMARY OF THE INVENTION

It is an object of the present invention to provide vaccine components for an anti HIV-1 vaccine which would represent a typical United States isolate HIV-1.

It is another object of the present invention to provide diagnostic tests for the detection of HIV-1.

Various other objects and advantages of the present invention will become apparent from the drawings and the following description of the invention.

BRIEF DESCRIPTION OF THE DRAWINGS

FIGS. 2A–2H shows the DNA sequence representing the MN-PH1 genome (SEQ ID NO:1).

FIGS. 3A–3C shows the predicted amino acid sequence of the MN-PH1 envelope (env) protein (SEQ ID NO:2).

FIGS. 6A–6S shows the DNA sequence representing the MN-ST1 genome (SEQ ID NO:3) and the predicted amino acid sequence of the MN-ST1 genome and env protein (SEQ ID NO:4).

FIGS. 8A–8H shows the DNA sequence of the env gene of BA-L (SEQ ID NO:5).

FIGS. 9A–9C shows the predicted amino acid sequence of the BA-L env protein (SEQ ID NO:6).

DETAILED DISCLOSURE OF THE INVENTION

Figure 1:
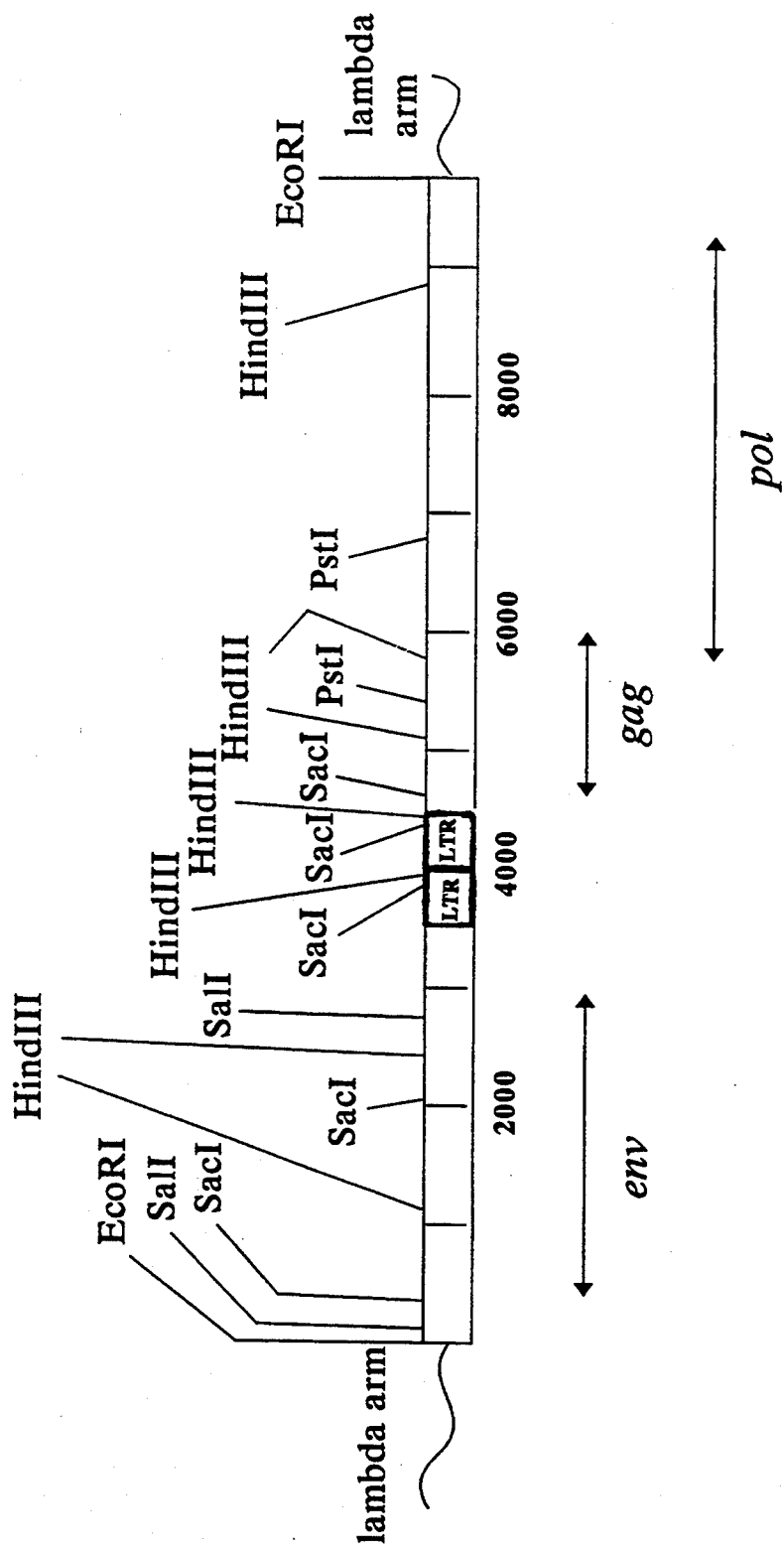
FIG. 1 shows the structure and restriction map of the lambda MN-PH1 clone.

The present invention relates to the HIV-1 virus strains, MN-ST1 and BA-L, which are more typical of the HIV-1 isolates found in the United States than previously known HIV-1 strains. Local isolates provide better material for vaccine and for the detection of the virus in biological samples, such as blood bank samples.

The present invention relates to DNA segments encoding the env protein of MN-ST1 or BA-L (the DNA sequence given in FIGS. 6A–6S and FIGS. 8A–8H being two such examples) and to nucleotide sequences complementary to the segments referenced above as well as to other genes and nucleotide sequences contained in these clones. The present invention also relates to DNA segments encoding a unique portion of the MN-ST1 env protein or the BA-L env protein. (A "unique portion" consists of at least five (or six) amino acids or corresponding at least 15 (or 18) nucleotides.)

The invention further relates to the HIV-1 virus strains MN-ST1 and BA-L themselves. The HIV-1 virus strains of the present invention are biologically active and can easily be isolated by one skilled in the art using known methodologies.

The above-described DNA segments of the present invention can be placed in DNA constructs which are then used in the transformation of host cells for generation of recombinantly produced viral proteins. DNA constructs of the present invention comprise a DNA segment encoding the env protein and the flanking region of MN-ST1 (or BA-L) or a portion thereof and a vector. The constructs can further comprise a second DNA segment encoding both a rev protein and a rev-responsive region of the env gene operably linked to the first DNA segment encoding the env protein. The rev protein facilitates efficient expression of the env protein in eucaryotic cells. Suitable vectors for use in the present invention include, but are not limited to, pSP72, lambda EMBL3 and SP65gpt.

Host cells to which the present invention relates are stably transformed with the above-described DNA constructs. The cells are transformed under conditions such that the viral protein encoded in the transforming construct is expressed. The host cell can be procaryotic (such as bacterial), lower eucaryotic (such as fungal, including yeast) or higher eucaryotic (such as mammalian). The host cells can be used to generate recombinantly produced MN-ST1 (or BA-L) env protein by culturing the cells in a manner allowing expression of the viral protein encoded in the construct. The recombinantly produced protein is easily isolated from the host cells using standard protein isolation protocols.

Since HIV-1 strains MN-ST1 and BA-L represent relatively typical United States genotypes, non-infectious MN-ST1 or BA-L proteins (for example, the env protein), peptides or unique portions of MN-ST1 or BA-L proteins (for example, a unique portion of the env protein), and even whole inactivated MN-ST1 or BA-L can be used as an immunogen in mammals, such as primates, to generate antibodies capable of neutralization and T cells capable of killing infected cells. The protein can be isolated from the virus or made recombinantly from a cloned envelope gene. Accordingly, the virus and viral proteins of the present invention are of value as either a vaccine or a component thereof, or an agent in immunotherapeutic treatment of individuals already infected with HIV-1.

As is customary for vaccines, a non-infectious antigenic portion of MN-ST1 or BA-L, for example, the env protein, can be delivered to a mammal in a pharmacologically acceptable carrier. The present invention relates to vaccines comprising non-infectious antigenic portions of either MN-ST1 or BA-L and vaccines comprising non-infectious antigenic portions of both MN-ST1 and BA-L. Vaccines of the present invention can include effective amounts of immunological adjuvants known to enhance an immune response. The viral protein or polypeptide is present in the vaccine in an amount sufficient to induce an immune response against the antigenic protein and thus to protect against HIV-1 infection. Protective antibodies are usually best elicited by a series of 2–3 doses given about 2 to 3 weeks apart. The series can be repeated when circulating antibodies concentration in the patient drops.

Virus derived from the infectious HIV-1(MN) clones, MN-ST1, may also be used for reproducible challenge experiments in chimpanzees treated with candidate HIV-1 vaccines or in vitro with human antiserum from individuals treated with candidate vaccines. A candidate vaccine can be administered to a test mammal, such as a chimpanzee prior to or simultaneously with the infectious MN-ST1 virus of the present invention. Effectiveness of the vaccine can be determined by detecting the presence or absence of HIV-1 infection in the test mammals. Side-by-side comparative tests can be run by further administering to a second set of test mammals the virus alone and comparing the number of infections which develop in the two sets of test mammals. Alternatively, candidate vaccines can be evaluated in humans by administering the vaccine to a patient and then testing the ability of the MN-ST1 virus to infect blood cells from the patient.

The present invention also relates to the detection of HIV-1 virus in a biological sample. For detection of an HIV-1 infection the presence of the virus, proteins encoded in the viral genome, or antibodies to HIV-1 is determined. Many types of tests, as one skilled in the art will recognize, can be used for detection. Such tests include, but are not limited to, ELISA and RIA.

In one bioassay of the present invention all, or a unique portion, of the env protein is coated on a surface and contacted with the biological sample. The presence of a resulting complex formed between the protein and antibodies specific therefor in the serum can be detected by any of the known methods commonly used in the art, such as, for example, fluorescent antibody spectroscopy or colorimetry.

EXAMPLES

MN-PH1 Clone

Figure 3A:
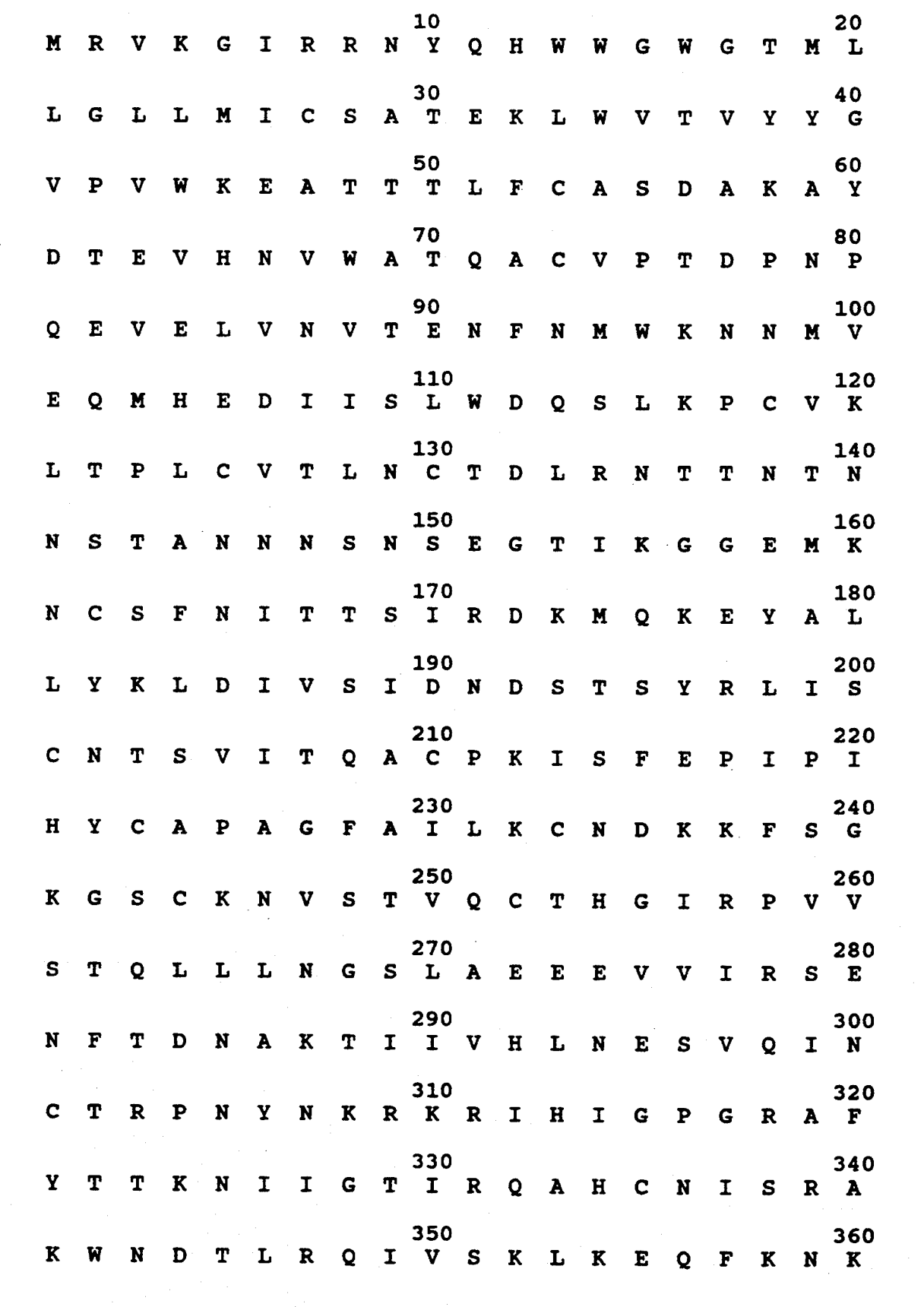
Figure 3B:
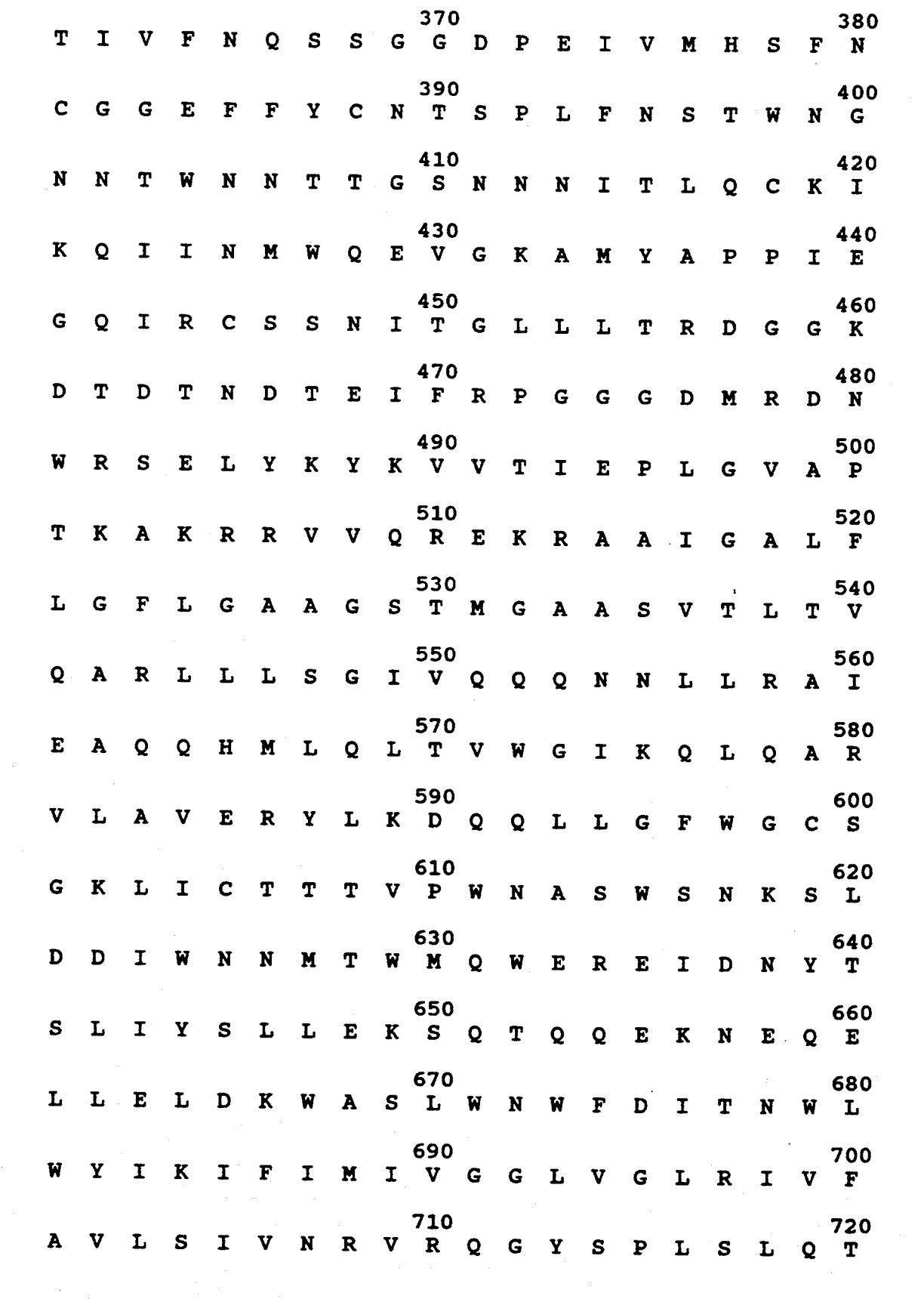
Figure 3C:
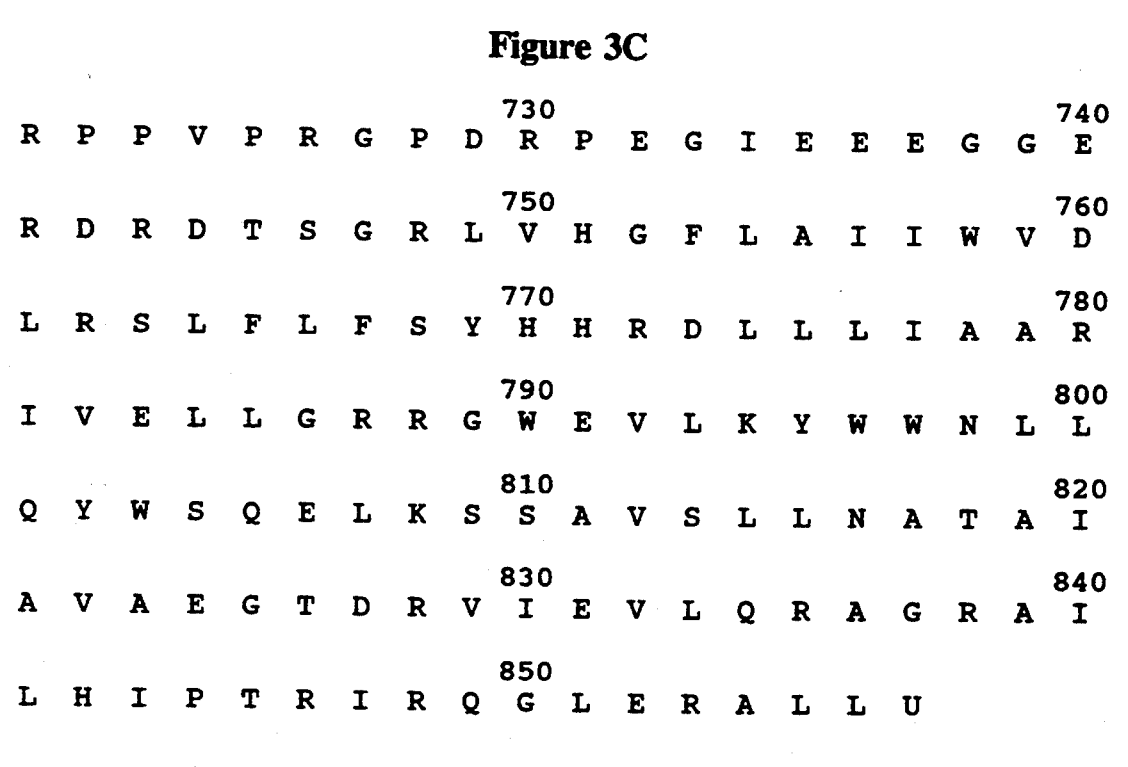
Figure 4:
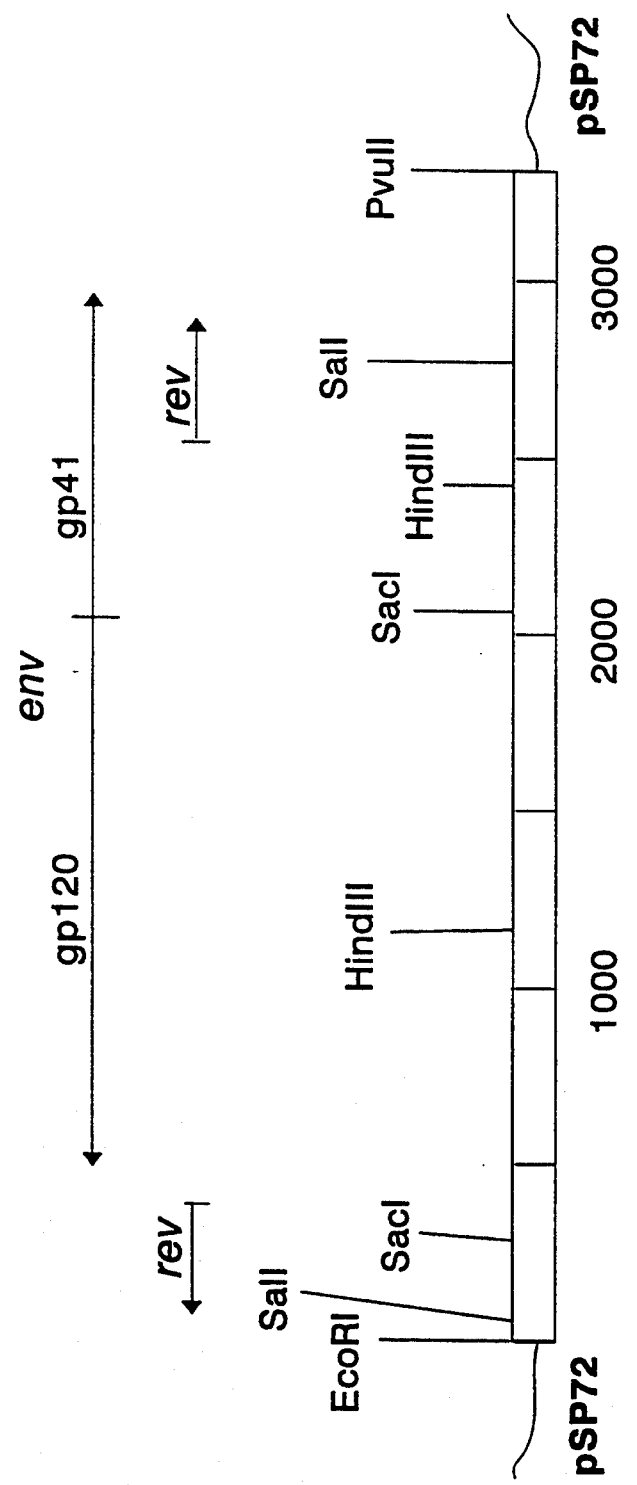
FIG. 4 shows the restriction map of the MN-PH1 envelope plasmid clone.

The permuted circular unintegrated viral DNA representing the complete HIV-1(MN) genome was cloned by standard techniques (Sambrook et al., 1989, Molecular Cloning. Cold Spring Harbor, N.Y.: Cold Spring Harbor Laboratory Press) into the Eco RI site of lambda gtWES.lambda B DNA from total DNA of H9 cells producing HIV-1(MN). This clone is designated lambda MN-PH1, and its structure and restriction map are shown in FIG. 1. The clone was subcloned into M13mp18 and M13mp19, and the DNA sequence of the entire clone, given in FIGS. 2A-2H, was obtained by the dideoxy chain termination method (Sanger et al., Proc. Natl. Acad. Sci. U.S.A. 74, 5463-5467, 1977). The amino acid sequence of the envelope protein (see FIGS. 3A-3C) was inferred from the DNA sequence. A restriction map of the cloned unintegrated viral DNA (see FIG. 1) was also obtained from the DNA sequence of lambda PH1 and used in conjunction with the inferred amino acid sequence of the viral proteins to subclone the envelope (env) gene into the commercially available plasmid pSP72 (Promega Biological Research Products, Madison, Wis.), as shown in FIG. 4. This plasmid (pMN-PH1env) contains, in addition to the coding regions for the envelope proteins, the coding region for the rev protein (Feinberg et al., Cell 46, 807-817, 1986) and the portion of the env gene which contains the rev-responsive region (Dayton et al., J. Acquir. Immune. Defic. Syndr. 1, 441-452, 1988), since both are necessary for efficient expression of the envelope protein in eucaryotic cells. This plasmid thus contains all the elements required for production of envelope protein following placement into appropriate expression vectors and introduction into recipient cells, all by standard techniques known to molecular biologists.

MN-ST1 Clone

Figure 5:
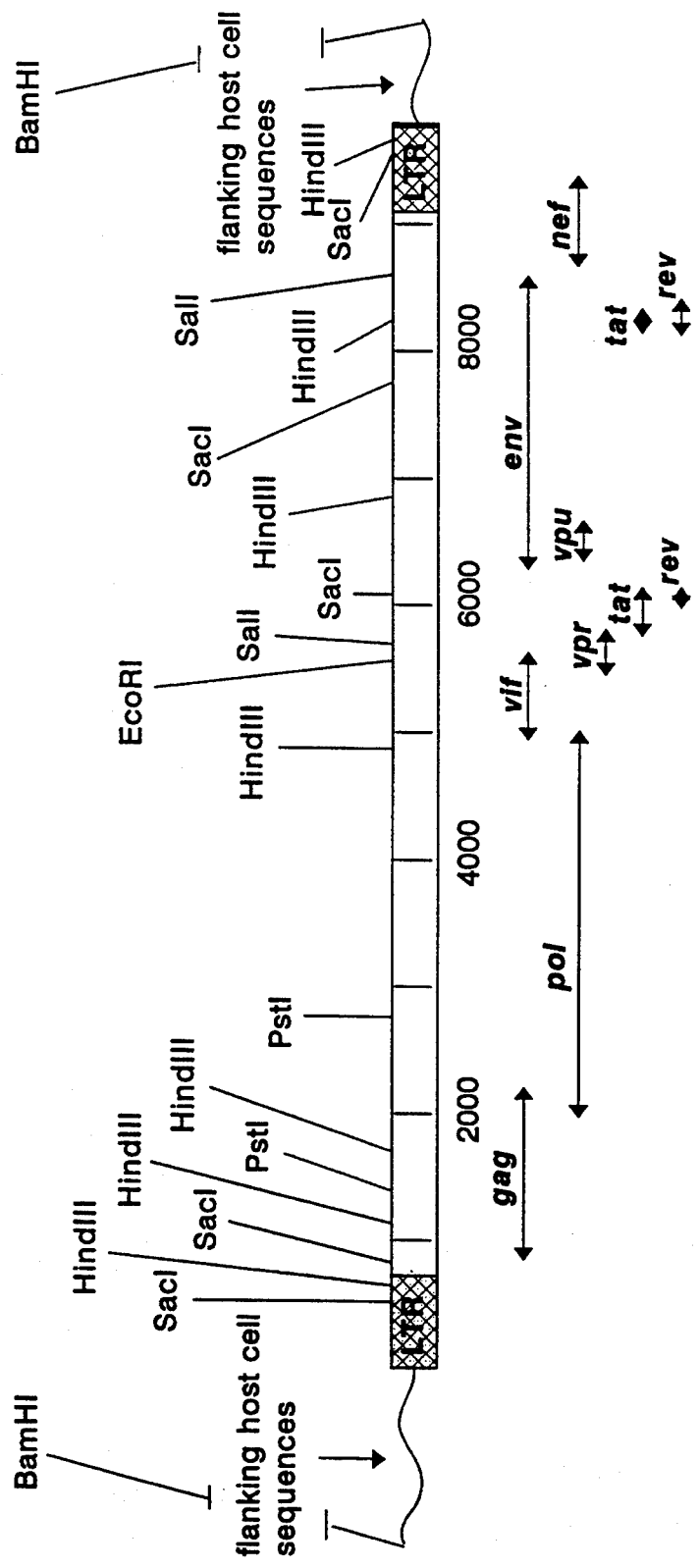
FIG. 5 shows the restriction map and structure of the lambda MN-ST1 clone.

The infectious molecular clone, lambda MN-ST1, was obtained by cloning integrated provirus from DNA purified from peripheral blood lymphocytes infected with HIV-1(MN) and maintained in culture for a short time (one month). The integrated proviral DNA was partially digested with the restriction enzyme Sau3A under conditions which gave a maximum yield of DNA fragments of from 15-20 kilobases (kb). This was cloned into the compatible BamHI site of lambda EMBL3, as shown in FIG. 5. FIG. 5 also shows the restriction map of clone lambda MN-ST1. The DNA sequence of the entire clone, given in FIGS. 6A-6S, was obtained by the dideoxy chain termination method (Sanger et al., Proc. Natl. Acad. Sci. U.S.A. 74, 5463-5467, 1977). The amino acid sequence was predicted from the DNA sequence (see FIGS. 6A-6S). This clone can be transfected into recipient cells by standard techniques. After transfection, the cloned proviral DNA is expressed into biologically active virus particles, which can be used as a source for virus stocks. The proviral DNA whose restriction map is shown in FIG. 4, was removed from the lambda phage vector by digestion with BamHI and inserted into a plasmid, SP65gpt (Feinberg et al., Cell 46, 807-817, 1986). This plasmid, pMN-ST1, contains an SV40 origin of replication. Consequently, transfection into COS-1 cells (Gluzman, Y. Cell 23, 175-182, 1981), which produce a SV40 gene product which interacts with the cognate origin of replication, results in a transient high plasmid copy number with a concomitant production of large amount of replication competent, infectious virus (Feinberg et al., Cell 46, 807-817, 1986). This provides a convenient source of genetically homogeneous virus, as well as a way to introduce desired mutations using standard methods.

The envelope gene was excised from the lambda phage clone and cloned into plasmid as described above for lambda MN-PH1. This clone (pMN-ST1env), is similar to pMN-PH1env, described above, except that it derives from a biologically active cloned provirus. Like pMN-PH1env, it can be placed in a suitable vector and host to produce the envelope protein of HIV-1(MN) by well known techniques.

BA-L Clone

Figure 7:
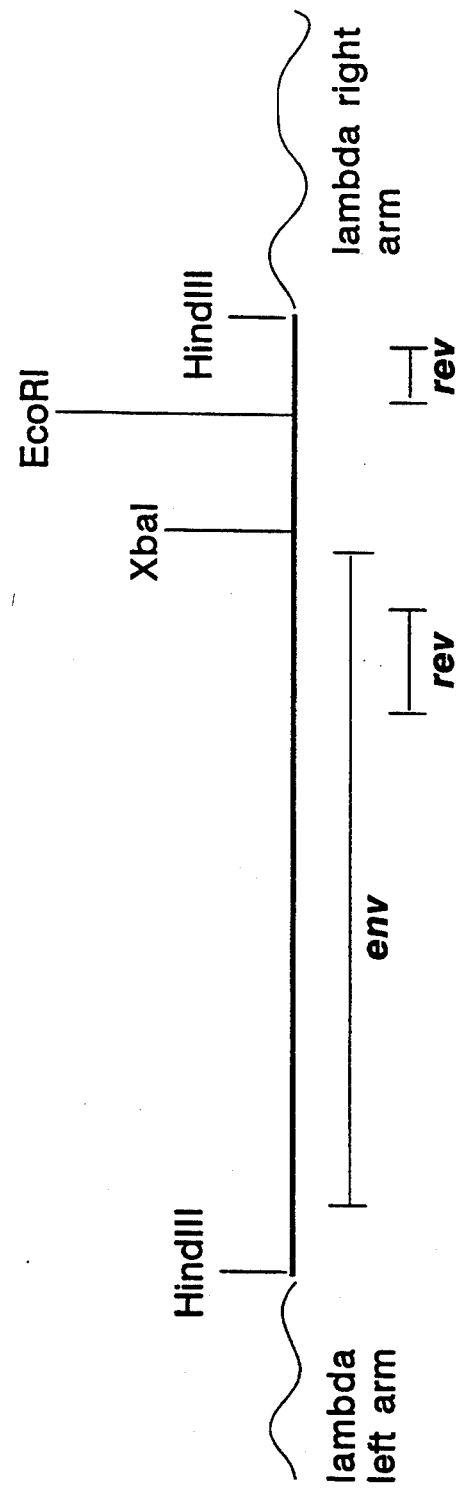
FIG. 7 shows the structure of the lambda BA-L clone.
Figure 10A:
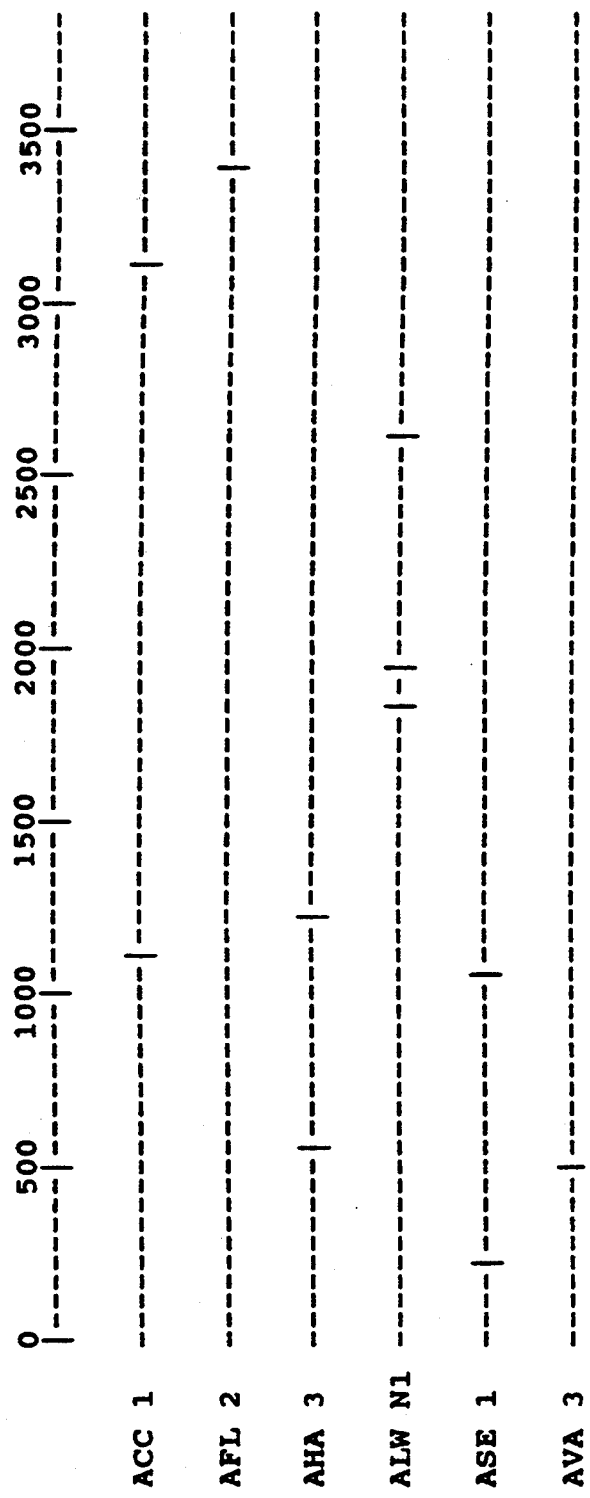
FIGS. 10A–10I shows the restriction map of the clone BA-L1.
Figure 10B:
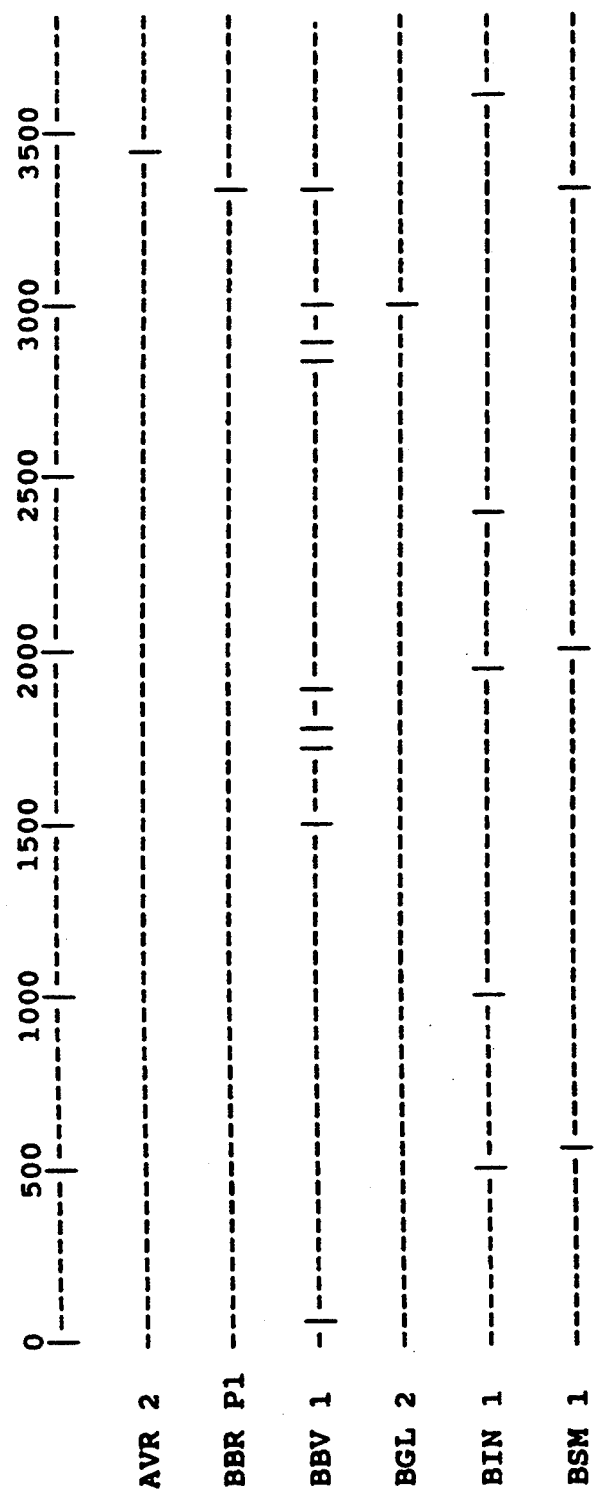
Figure 10C:
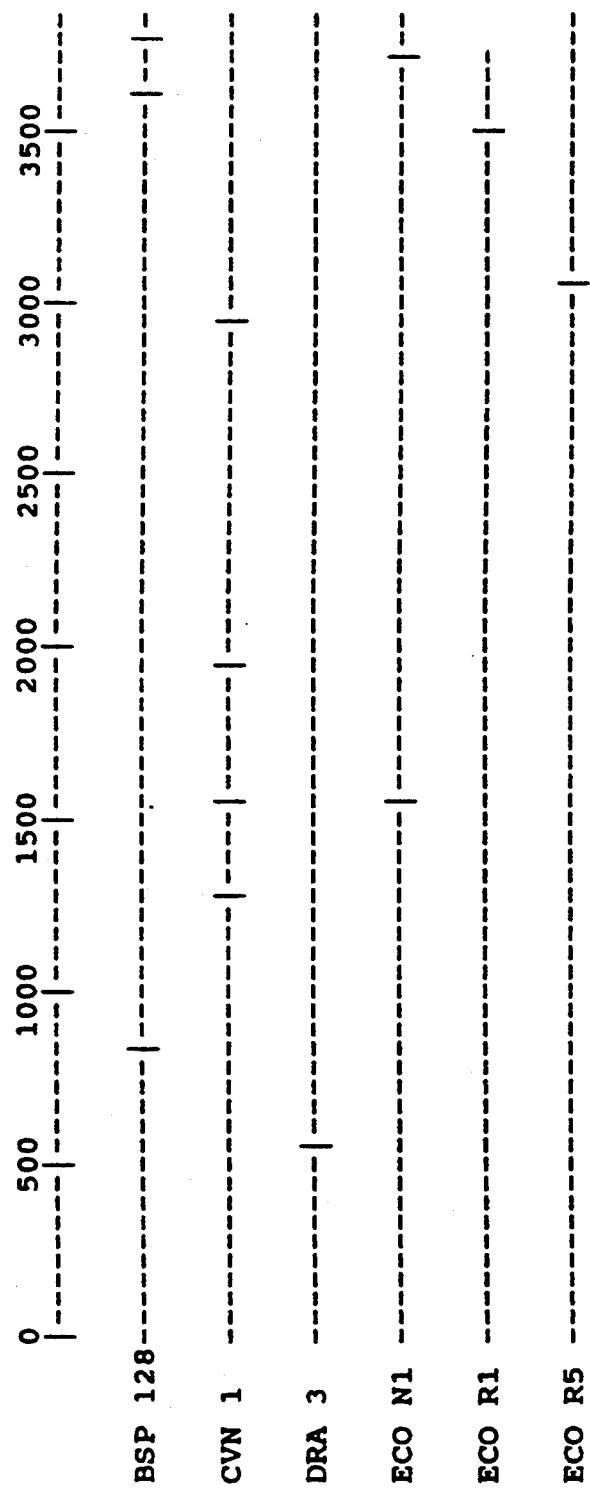
Figure 10D:
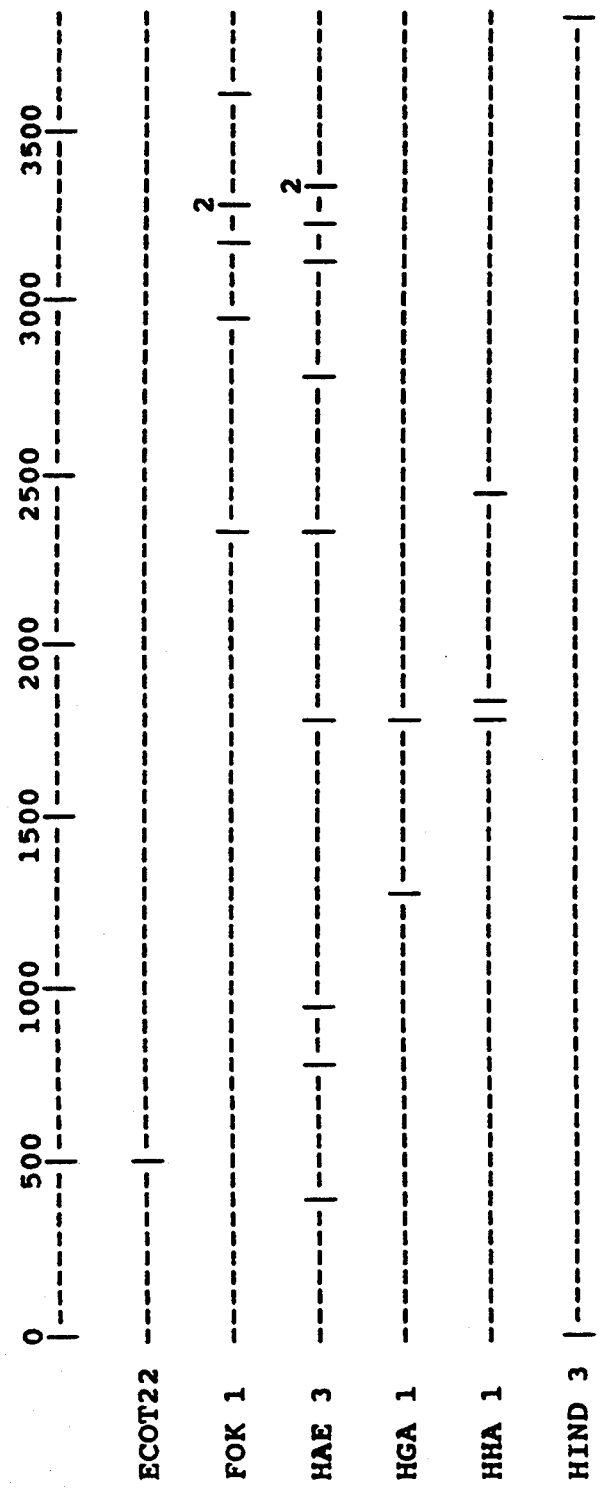
Figure 10E:
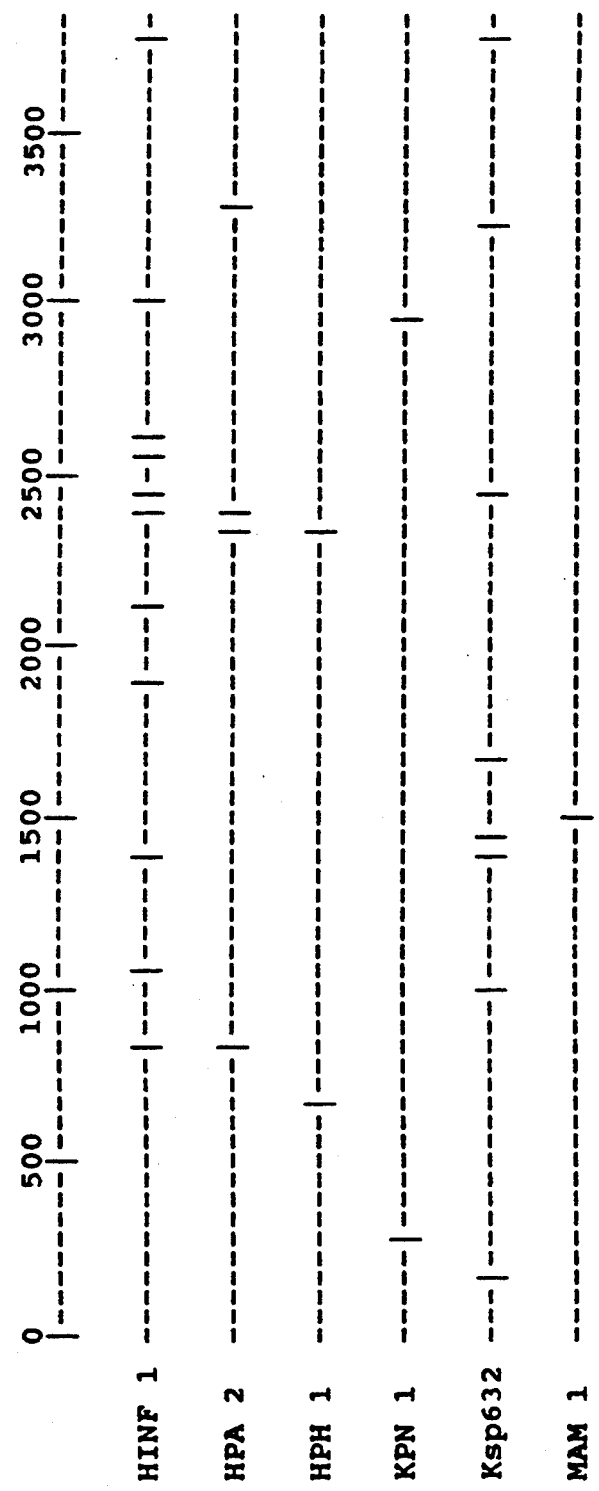
Figure 10F:
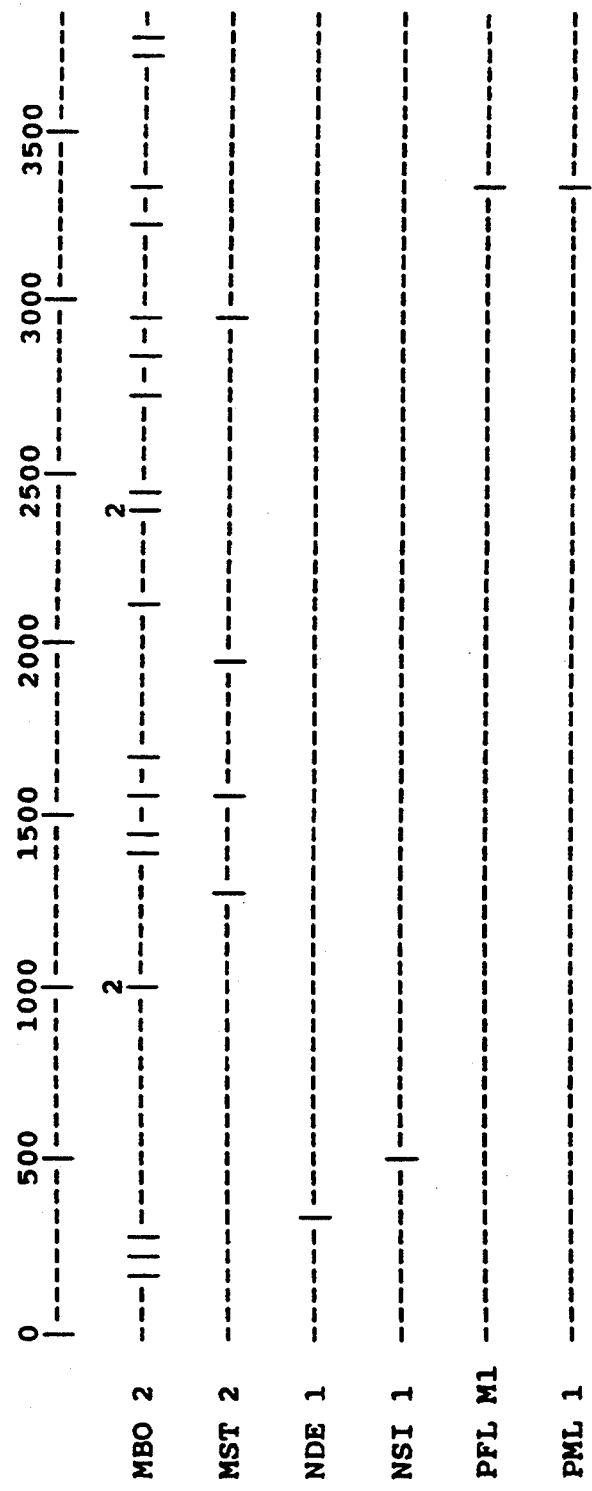
Figure 10G:
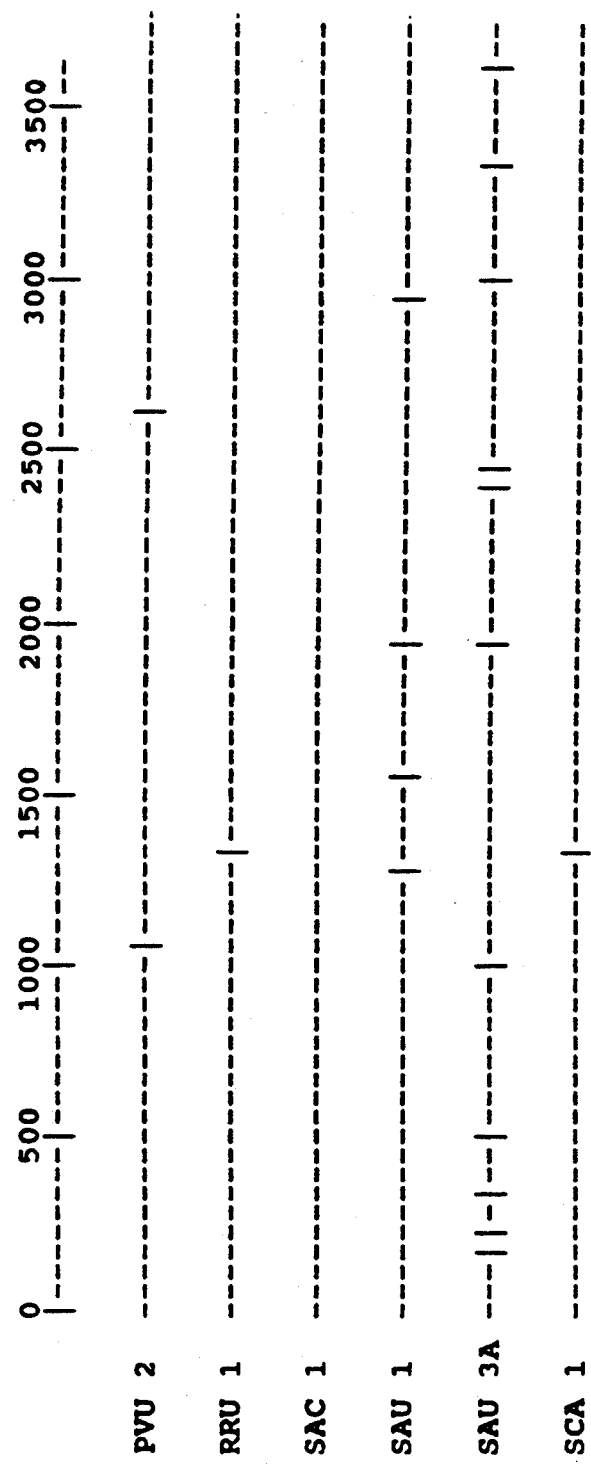
Figure 10H:
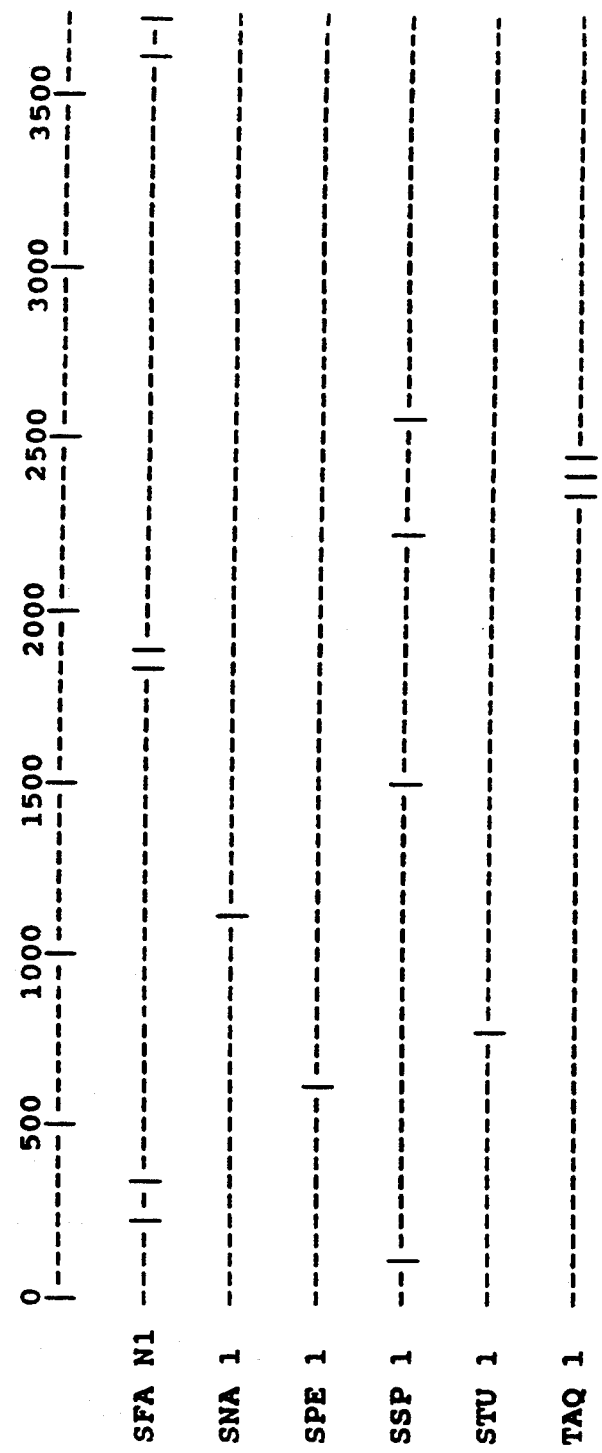
Figure 10I:
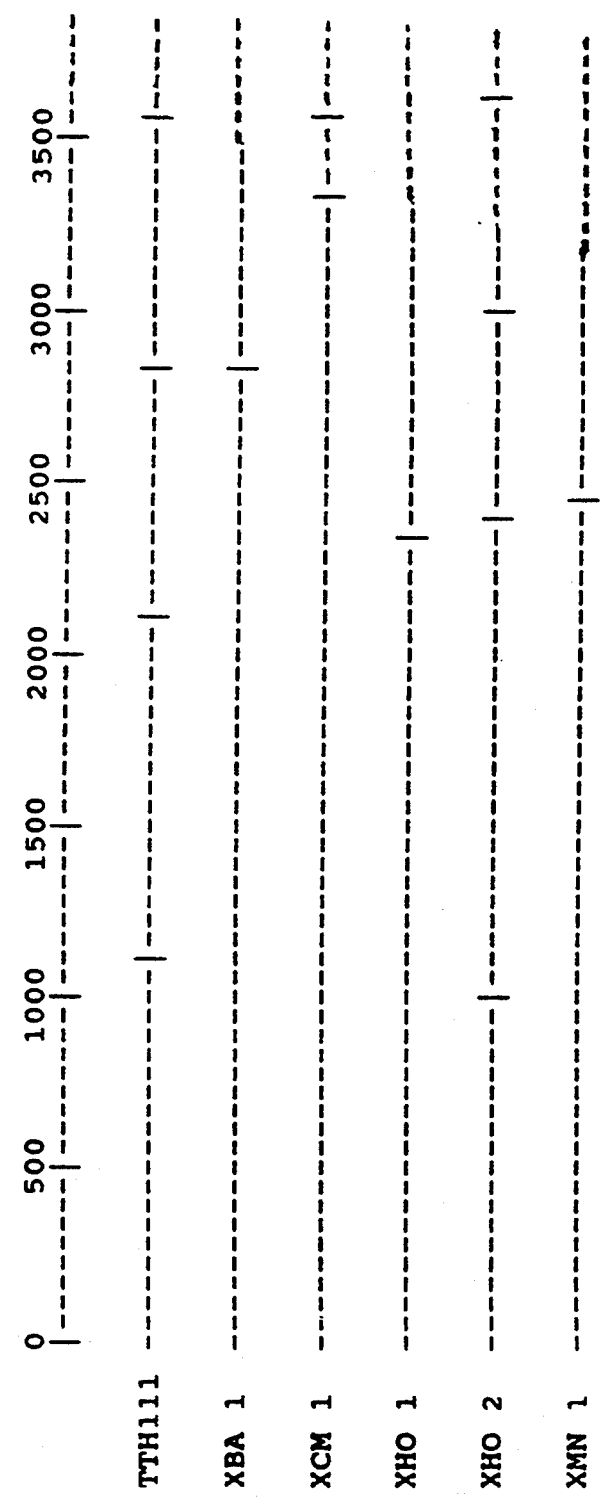

A Hind III fragment of unintegrated viral DNA representing the HIV-1(BA-L) genome was cloned by standard techniques into lambda phage Charon 28 DNA from total DNA of peripheral blood macrophages infected with and producing HIV-1(BA-L). A positive clone was selected by hybridization using a radiolabelled probe for the HIV-1 envelope. This clone, designated lambda BA-L1, was found to contain the entire gene for the envelope protein. Its structure is given in FIG. 7. The insert was transferred into a plasmid (pBluescript, Stratagene, LaJolle, Calif.) and the DNA sequence of the env gene was determined (see FIGS. 8A-8H). This clone is designated pBA-L1.

Figure 9A:
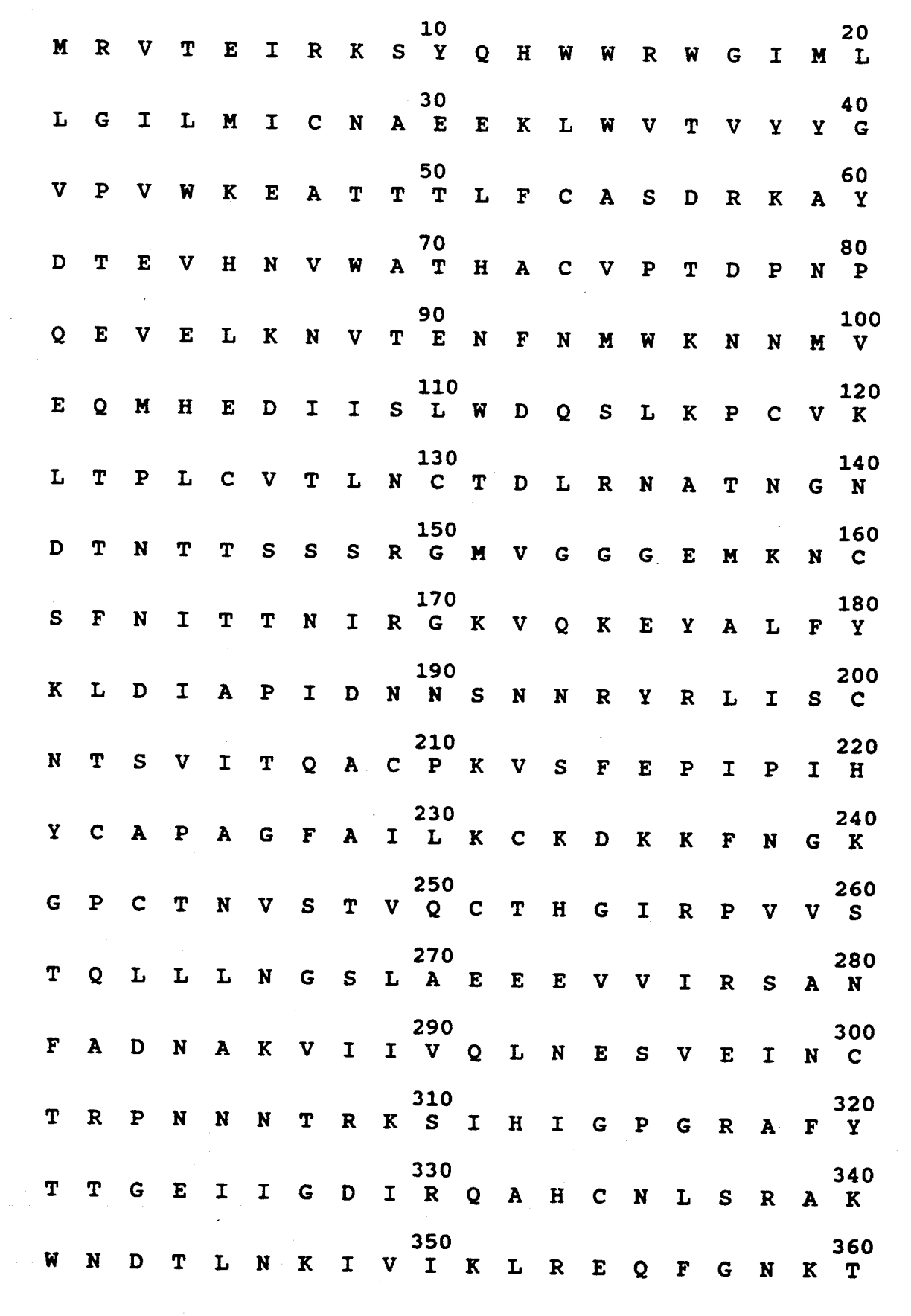
Figure 9B:
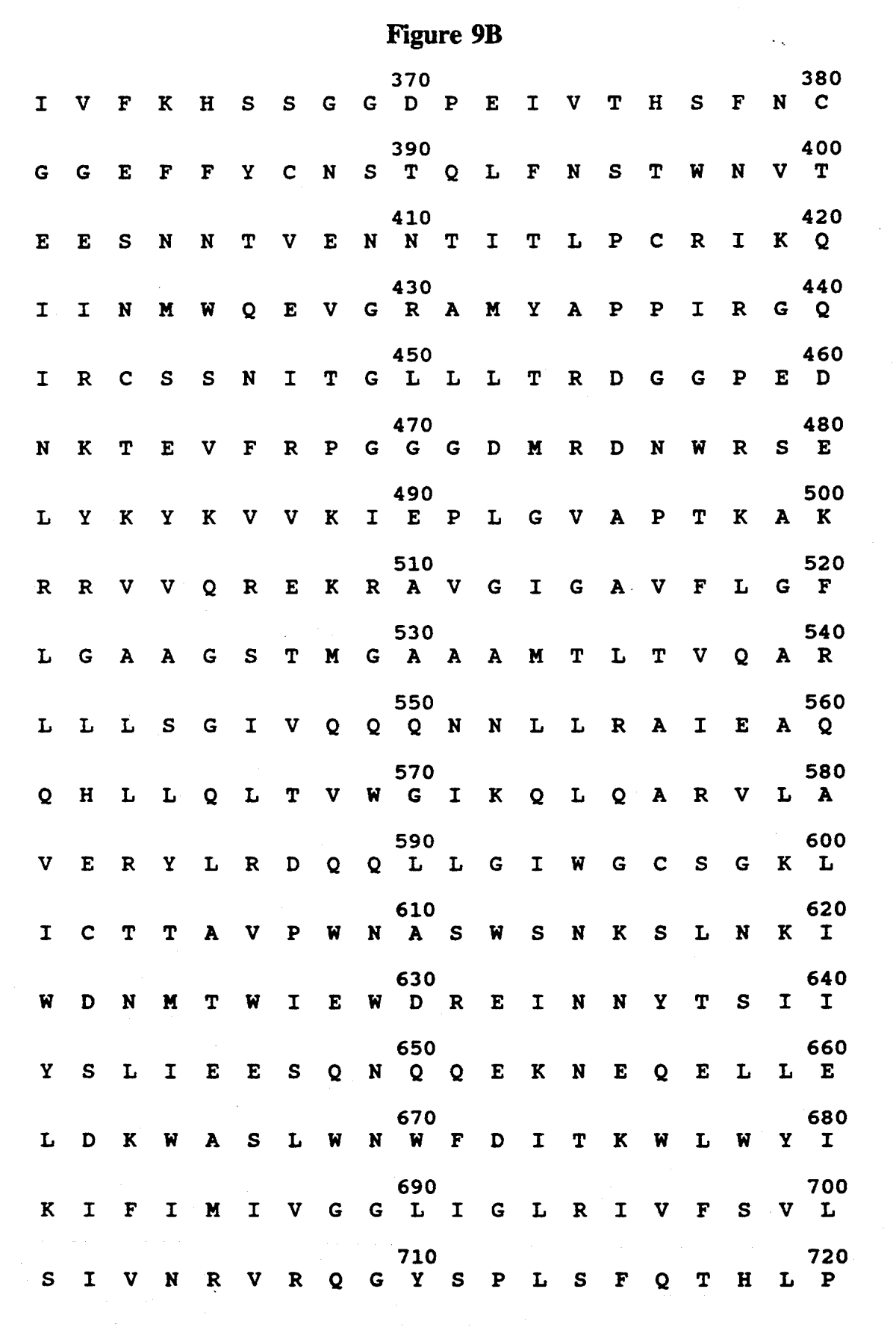
Figure 9C:
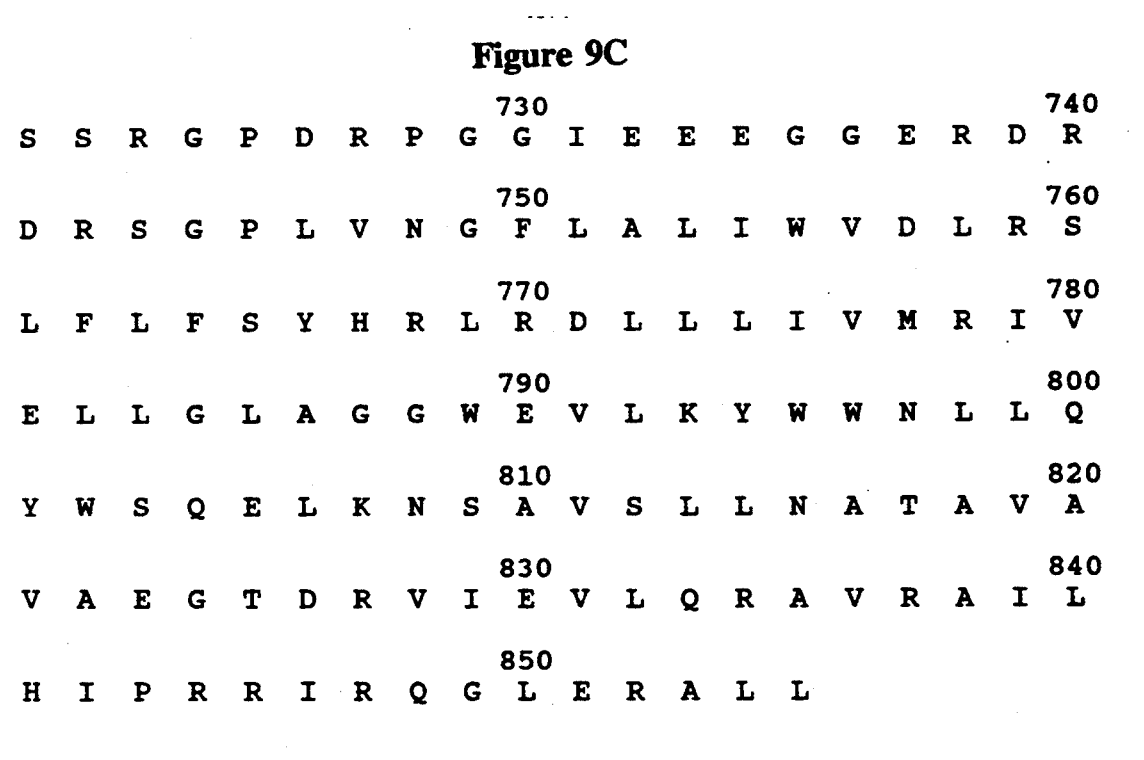

The amino acid sequence of the envelope protein, shown in FIGS. 9A-9C, was inferred from the DNA sequence. A restriction map was also obtained from the DNA sequence of BA-L1 (shown in FIGS. 10A-10I) in order to determine the appropriate restriction enzyme sites for cloning the env gene into suitable expression vectors. An Eco RI-HindIII fragment of 0.4 Kb and a 2.8 Kb HindIII-XbaI fragment when cloned together constitute the entire env gene. This plasmid contains, in addition to the coding regions for the envelope proteins, the coding region for the rev protein and the portion of the env protein which contains the rev-responsive region. Both are necessary for efficient expression of the envelope protein in eucaryotic cells (Feinberg et al., Cell 46, 807-817, 1986; Dayton et al., J. Acquir. Immune. Defic. Syndr. 1, 441-452). This plasmid thus contains all the HIV-1 genetic elements required for production of envelope protein following placement into appropriate expression vectors and introduction into recipient cells, all by standard techniques well known in the art.

Statement of Deposit

The lambda MN-ST1 clone and the BA-L plasmid clone were deposited at the American Type Culture Collection (Rockville, Md.) under the terms of the Budapest Treaty. The lambda MN-ST1 clone has been assigned the ATCC accession number ATCC 40889 and the BA-L plasmid clone has been assigned the ATCC accession number ATCC 40890.

All publications mentioned hereinabove are hereby incorporated by reference.

While the foregoing invention has been described in some detail for purposes of clarity and understanding, it will be appreciated by one skilled in the art from a reading of this disclosure that various changes in form

What is claimed is:

1. A purified and isolated DNA encoding HIV-1 virus strain MN-ST1 having the DNA sequence of SEQ ID NO:3.

2. Lamda MN-ST1 clone deposited under ATCC Accession Number 40889.

3. A purified and isolated DNA encoding the env protein of HIV-1 virus strain MN-ST1 having the amino acid sequence of SEQ ID NO:4.

4. A vector comprising DNA encoding HIV-1 virus strain MN-ST1 having the DNA sequence of SEQ ID NO:3.

5. A vector comprising DNA encoding the env protein of HIV-1 virus strain MN-ST1 having the amino acid sequence of SEQ ID NO:4.

6. A host cell transformed or transfected with DNA encoding HIV-1 virus strain MN-ST1 having the DNA sequence of SEQ ID NO:3.

7. A host cell transformed or transfected with DNA encoding the env protein of HIV-1 virus strain MN-ST1 having the amino acid sequence of SEQ ID NO:4.

8. A virus particle produced by the host cell of claim 6.

9. Env protein produced by the host cell of claim 8.

10. Isolated env protein of HIV-1 virus strain MN-ST1 having the amino acid sequence of SEQ ID NO: 4.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 9739 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 6240..8810

( x i ) SEQUENCE DESCRIPTION: SEQ ID NO:1:

```
TGGAAGGGCT AATTCACTCC CAACGAAGAC AAGATATCCT TGATCTGTGG ATCTACCACA    60
CACAAGGCTA CTTCCCTGAT TAGCAGAACT ACACACCAGG GCCAGGGATC AGATATCCAC   120
TGACCTTTGG ATGGTGCTAC AAGCTAGTAC CAGTTGAGCC AGAGAAGTTA GAAGAAGCCA   180
ACAAAGGAGA GAACACCAGC TTGTTACACC CTGTGAGCCT GCATGGAATG GATGACCCGG   240
AGAGAGAAGT GTTAGAGTGG AGGTTTGACA GCCGCCTAGC ATTTCATCAC ATGGCCCGAG   300
AGCTGCATCC GGAGTACTTC AAGAACTGCT GACATCGAGC TTGCTACAAG GGACTTTCCG   360
CTGGGGACTT TCCAGGGAGG CGTGGCCTGG GCGGGACTGG GAGTGGCGA GCCCTCAGAT    420
CCTGCATATA AGCAGCTGCT TTTTGCCTGT ACTGGGTCTC TCTGGTTAGA CCAGATCTGA   480
GCCTGGGAGC TCTCTGGCTA ACTAGGGAAC CCACTGCTTA AGCCTCAATA AAGCTTGCCT   540
TGAGTGCTTC AAGTAGTGTG TGCCCGTCTG TTATGTGACT CTGGTAGCTA GAGATCCCTC   600
AGATCCTTTT AGGCAGTGTG GAAAATCTCT AGCAGTGGCG CCCGAACAGG GACTTGAAAG   660
CGAAAGAAAA ACCAGAGCTC TCTCGACGCA GGACTCGGCT TGCTGAAGCG CGCACGGCAA   720
GAGGCGAGGG GCGGCGACTG GTGAGTACGC CAAAAATTCT TGACTAGCGG AGGCTAGAAG   780
GAGAGAGATG GGTGCGAGAG CGTCGGTATT AAGCGGGGGA GAATTAGATC GATGGGAAAA   840
CATTCGGTTA AGGCCAGGGG GAAAGAAAAA ATATAAATTA AAACATGTAG TATGGGCAAG   900
CAGGGAGCTA GAACGATTCG CAGTCAATCC TGGCCTGTTA GAAACATCAG AAGGCTGTAG   960
ACAAATACTG GGACAGCTAC AACCATCCCT TCAGACAGGA TCAGAAGAAC TTAAATCATT  1020
ATATAATACA GTAGCAACCC TCTATTGTGT GCATCAAAAG ATAGAGATAA AAGACACCAA  1080
GGAAGCTTTA GAGAAAATAG AGGAAGAGCA AAACAAAAGT AAGAAAAAAG CACAGCAAGC  1140
AGCAGCTGAC ACAGGAAACA GAGGAAACAG CAGCCAAGTC AGCCAAAATT ACCCCATAGT  1200
GCAGAACATC GAGGGGCAAA TGGTACATCA GGCCATATCA CCTAGAACTT TAAATGCATG  1260
GGTAAAAGTA GTAGAAGAGA AGGCTTTCAG CCCAGAAGTA ATACCCATGT TTTCAGCATT  1320
ATCAGAAGGA GCCACCCCAC AAGATTTAAA CACCATGCTA AACACAGTGG GGGGACATCA  1380
AGCAGCCATG CAAATGTTAA AAGAGACCAT CAATGAGGAA GCTGCAGAAT GGGATAGATT  1440
GCATCCAGTG CATGCAGGGC CTATTACACC AGGCCAGATG AGAGAACCAA GGGGAAGTGA  1500
CATAGCAGGA ACTACTAGTA CCCTTCAGGA ACAAATAGGA TGGATGACAA ATAATCCACC  1560
TATCCCAGTA GGAGAAATCT ATAAAAGATG GATAATCCTG GGATTAAATA AAATAGTAAG  1620
GATGTATAGC CCTTCCAGCA TTCTGGACAT AAGACAAGGA CCAAAGGAAC CCTTTAGAGA  1680
CTATGTAGAC CGGTTCTATA AAACTCTAAG AGCCGAGCAA GCTTCACAGG AGGTAAAAAA  1740
```

```
CCGGACGACA  GAAACCTTGT  TGGTCCAAAA  TGCGAACCCA  GATTGTAAGA  CTATTTTAAA  1800
AGCATTGGGA  CCAGCAGCTA  CACTAGAAGA  AATGATGACA  GCATGTCAGG  GAGTGGGAGG  1860
ACCTGGTCAT  AAAGCAAGAG  TTTTGGCGGA  AGCGATGAGC  CAAGTAACAA  ATTCAGCTAC  1920
CATAATGATG  CAGAGAGGCA  ATTTTAGGAA  TCAAGAAAG   ATTATCAAGT  GCTTCAATTG  1980
TGGCAAAGAA  GGGCACATAG  CCAAAAATTG  CAGGGCCCCT  AGGAAAGGG   GCTGTTGGAA  2040
ATGTGGAAAG  GAAGGACACC  AAATGAAAGA  TTGTACTGAG  AGACAGGCTA  ATTTTTAGG   2100
GAAGATCTGG  CCTTCCTGCA  AGGGAAGGCG  GAATTTTCCT  CAGAGCAGAA  CAGAGCCAAC  2160
AGCCCCACCA  GAAGAGAGCT  TCAGGTTTGG  GGAAGAGACA  CAACTCCCT   ATCAGAAGCA  2220
GGAGAAGAAG  CAGGAGACGA  TAGACAAGGA  CCTGTATCCT  TTAGCTTCCC  TCAAATCACT  2280
CTTTGGCAAC  GACCCATTGT  CACAATAAAG  ATAGGGGGGC  AACTAAAGGA  AGCTCTATTA  2340
GATACAGGAG  CAGATGATAC  AGTATTAGGA  GAAATGAATT  TGCCAAGAAG  ATGGAAACCA  2400
AAAATGATAG  GGGGAATTGG  AGGTTTTATC  AAAGTAAGAC  AGTATGATCA  GATAACCATA  2460
GGAATCTGTG  GACATAAAGC  TATAGGTACA  GTATTAGTAG  GACCTACACC  TGTCAACATA  2520
ATTGGAAGAA  ATCTGTTGAC  TCAGCTTGGG  TGCACTTTAA  ATTTTCCCAT  TAGTCCTATT  2580
GAAACTGTAC  CAGTAAAATT  AAAGCCAGGA  ATGGATGGCC  CAAAAGTTAA  ACAATGGCCA  2640
TTGACAGAAG  AAAAAATAAA  AGCATTAATA  GAAATTTGTA  CAGAAATGGA  AAAGGAAGGG  2700
AAAATTTCAA  AAATTGGGCC  TGAAAATCCA  TACAATACTC  CAGTATTTGC  CATAAAGAAA  2760
AAAGACAGTA  CTAAATGGAG  AAAATTAGTA  GATTTCAGAG  AACTTAATAA  GAAAACTCAA  2820
GACTTCTGGG  AAGTTCAATT  AGGAATACCA  CATCCTGCAG  GGTTAAAAAA  GAAAAAATCA  2880
GTAACAGTAC  TGGATGTGGG  TGATGCATAT  TTTTCAGTTC  CCTTAGATAA  AGACTTCAGG  2940
AAGTATACTG  CATTTACCAT  ACCTAGTATA  AACAATGAAA  CACCAGGGAT  TAGATATCAG  3000
TACAATGTGC  TTCCACAGGG  ATGGAAAGGA  TCACCAGCAA  TATTCCAAAG  TAGCATGACA  3060
AAAATCTTAG  AGCCTTTTAG  AAAACAAAAT  CCAGACATAG  TTATCTATCA  ATACATGGAT  3120
GATTTGTATG  TAGGATCTGA  CTTAGAAATA  GGGCAGCATA  GAGCAAAAAT  AGAGGAACTG  3180
AGACGACATC  TGTTGAGGTG  GGGATTTACC  ACACCAGACA  AAAAACATCA  GAAAGAACCT  3240
CCATTCCTTT  GGATGGGTTA  TGAACTCCAT  CCTGATAAAT  GGACAGTACA  GCCTATAGTG  3300
CTACCAGAAA  AAGACAGCTG  GACTGTCAAT  GACATACAGA  AGTTAGTGGG  AAAATTGAAT  3360
TGGGCAAGTC  AGATTTACGC  AGGGATTAAA  GTAAAGCAAT  TATGTAAACT  CCTTAGAGGA  3420
ACCAAAGCAC  TAACAGAAGT  AATACCACTA  ACAGAAGAAG  CAGAGCTAGA  ACTGGCAGAA  3480
AACAGGGAAA  TTCTAAAAGA  ACCAGTACAT  GGAGTGTATT  ATGACCCATC  AAAAGACTTA  3540
ATAGCAGAAG  TACAGAAGCA  GGGGCAAGGC  CAATGGACAT  ATCAAATTTA  TCAAGAGCCA  3600
TTTAAAAATC  TGAAAACAGG  CAAATATGCA  AGAATGAGGG  GTGCCCACAC  TAATGATGTA  3660
AAACAATTAA  CAGAGGCAGT  GCAAAAAATA  GCCACAGAAA  GCATAGTAAT  ATGGGGAAAG  3720
ACTCCTAAAT  TTAGACTACC  CATACAAAAA  GAAACATGGG  AAACATGGTG  GACAGAGTAT  3780
ACGTAAGCCA  CCTGGATTCC  TGAGTGGGAG  GTTGTCAATA  CCCCTCCCTT  AGTGAAATTA  3840
TGGTACCAGT  TAGAGAAAGA  ACCCATAGTA  GGTGCAGAAA  CTTTCTATGT  AGATGGGGCA  3900
GCTAACAGGG  AGACTAAAAA  AGGAAAAGCA  GGATATGTTA  CTAACAGAGG  AAGACAAAAG  3960
GTTGTCTCCC  TAACTGACAC  AACAAATCAG  AAGACTGAGT  TACAAGCAAT  TCATCTAGCT  4020
TTGCAAGATT  CAGGGTTAGA  AGTAAACATA  GTAACAGACT  CACAATATGC  ATTAGGAATC  4080
ATTCAAGCAC  AACCAGATAA  AAGTGAATCA  GAGTTAGTCA  GTCAAATAAT  AGAGCAGTTA  4140
ATAAAAAAGG  AAAAGGTCTA  TCTGGCATGG  GTACCAGCAC  ACAAAGGAAT  TGGAGGAAAT  4200
```

| | | | | | |
|---|---|---|---|---|---|
| GAACAAGTAG | ATAAATTAGT | CAGTGCTGGA | ATCAGGAAAG | TACTATTTTT | AGATGGAATA 4260 |
| GATAAGGCCC | AAGAAGACCA | TGAGAAATAT | CACAGTAATT | GGAGAGCAAT | GGCTAGTGAC 4320 |
| TTTAACCTAC | CACCTATAGT | AGCAAAAGAA | ATAGTAGCCA | GCTGTGATAA | ATGTCAGCTA 4380 |
| AAAGGAGAAG | CCATGCATGG | ACAAGTAGAC | TGTAGTCCAG | GAATATGGCA | ACTAGATTGT 4440 |
| ACACATTTAG | AAGGAAAAGT | TATCCTGGTA | GCAGTTCATG | TAGCCAGTGG | ATACATAGAA 4500 |
| GCAGAAGTTA | TTCCAGCAGA | GACAGGGCAG | GAGACAGCAT | ACTTTCTCTT | AAAATTAGCA 4560 |
| GGAAGATGGC | CAGTAAAAAC | AATACATACA | GACAATGGCC | CCAATTTCAC | CAGTACTACG 4620 |
| GTTAAGGCCG | CCTGTTGGTG | GACGGGAATC | AAGCAGGAAT | TTGGCATTCC | CTACAATCCC 4680 |
| CAAAGTCAAG | GAGTAATAGA | ATCTATGAAT | AAAGAATTAA | AGAAAATTAT | AGGACAGGTA 4740 |
| AGAGATCAGG | CTGAACATCT | TAAGAGAGCA | GTACAAATGG | CAGTATTCAT | CCACAATTTT 4800 |
| AAAAGAAAAG | GGGGGATTGG | GGGGTACAGT | GCAGGGGAAA | GAATAGTAGG | CATAATAGCA 4860 |
| ACAGACATAC | AAACTAAAGA | ACTACAAAAA | CAAATTACAA | AAATTCAAAA | TTTTCGGGTT 4920 |
| TATTACAGGG | ACAGCAGAGA | TCCACTTTGG | AAAGGACCAG | CAAAGCTTCT | CTGGAAAGGT 4980 |
| GAAGGGGCAG | TAGTAATACA | AGATAATAAT | GACATAAAAG | TAGTGCCAAG | AAGAAAAGCA 5040 |
| AAGGTCATTA | GGGATTATGG | AAAACAGACG | GCAGGTGATG | ATTGTGTGGC | AAGCAGACAG 5100 |
| GATGAGGATT | AGAACATGGA | AAAGTTTAGT | AAAACACCAT | ATGTATATTT | CAAAGAAAGC 5160 |
| TAAAGGACGG | TTTTATAGAC | ATCACTATGA | AAGCACTCAT | CCAAGAATAA | GTTCAGAAGT 5220 |
| ACACATCCCA | CTAGGGGATG | CTAGATTGGT | AATAACAACA | TATTGGGGTC | TGCATACAGG 5280 |
| AGAAAGAGAC | TGGCATTTAG | GTCAGGGAGT | CTCCATAGAA | TGGAGGAAAA | AGAGATATAG 5340 |
| CACACAAGTA | GACCCTGACC | TAGCAGACCA | CCTAATTCAT | CTGCATTACT | TTGATTGTTT 5400 |
| TTCAGACTCT | GCCATAAGAA | AGGCCATATT | AGGACATAGA | GTTAGTCCTA | TTTGTGAATT 5460 |
| TCAAGCAGGA | CATAACAAGG | TAGGACCTCT | ACAGTACTTG | GCACTAACAG | CATTAATAAC 5520 |
| ACCAAAAAAG | ATAAAGCCAC | CTTTGCCTAG | TGTTAAGAAA | CTGACAGAGG | ATAGATGGAA 5580 |
| CAAGCCCCAG | AAGACCAAGG | GCCACAGAGG | GAGCCATACA | ATCAATGGGC | ACTAGAGCTT 5640 |
| TTAGAGGAGC | TTAAGAATGA | AGCTGTTAGA | CATTTTCCTA | GGATATGGCT | CCATGGCTTA 5700 |
| GGGCAACATA | TCTATGAAAC | TTATGGGGAT | ACTTGGGCAG | GAGTGGAAGC | CATAATAAGA 5760 |
| ATTCTACAAC | AACTGCTGTT | TATTCATTTC | AGAATTGGGT | GTCGACATAG | CAGAATAGGC 5820 |
| ATTATTCGAC | AGAGGAGAGC | AAGAAATGGA | GCCAGTAGAT | CCTAGACTAG | AGCCCTGGAA 5880 |
| GCATCCAGGA | AGTCAGCCTA | AGACTGCTTG | TACCACTTGC | TATTGTAAAA | AGTGTTGCTT 5940 |
| TCATTGCCAA | GTTTGTTTCA | CAAAAAAGC | CTTAGGCATC | TCCTATGGCA | GGAAGAAGCG 6000 |
| GAGACAGCGA | CGAAGAGCTC | CTGAAGACAG | TCAGACTCAT | CAAGTTTCTC | TACCAAAGCA 6060 |
| GTAAGTAGTA | CATGTAATGC | AACCTTTAGT | AATAGCAGCA | ATAGTAGCAT | TAGTAGTAGC 6120 |
| AGGAATAATA | GCAATAGTTG | TGTGATCCAT | AGTATTCATA | GAATATAGGA | AAATAAGAAG 6180 |
| ACAAAGAAAA | ATAGACAGGT | TAATTGATAG | AATAAGCGAA | AGAGCAGAAG | ACAGTGGCA 6239 |

| | | | | | | | | | | | | | | | | |
|---|---|---|---|---|---|---|---|---|---|---|---|---|---|---|---|---|
| ATG | AGA | GTG | AAG | GGG | ATC | AGG | AGG | AAT | TAT | CAG | CAC | TGG | TGG | GGA | TGG | 6287 |
| Met | Arg | Val | Lys | Gly | Ile | Arg | Arg | Asn | Tyr | Gln | His | Trp | Trp | Gly | Trp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GGC | ACG | ATG | CTC | CTT | GGG | TTA | TTA | ATG | ATC | TGT | AGT | GCT | ACA | GAA | AAA | 6335 |
| Gly | Thr | Met | Leu | Leu | Gly | Leu | Leu | Met | Ile | Cys | Ser | Ala | Thr | Glu | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| TTG | TGG | GTC | ACA | GTC | TAT | TAT | GGG | GTA | CCT | GTG | TGG | AAA | GAA | GCA | ACC | 6383 |
| Leu | Trp | Val | Thr | Val | Tyr | Tyr | Gly | Val | Pro | Val | Trp | Lys | Glu | Ala | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| ACC | ACT | CTA | TTT | TGT | GCA | TCA | GAT | GCT | AAA | GCA | TAT | GAT | ACA | GAG | GTA | 6431 |
| Thr | Thr | Leu | Phe | Cys | Ala | Ser | Asp | Ala | Lys | Ala | Tyr | Asp | Thr | Glu | Val | |

-continued

|   |   |   |   |   | 50 |   |   |   |   | 55 |   |   |   |   | 60 |   |   |
|---|---|---|---|---|---|---|---|---|---|---|---|---|---|---|---|---|---|

```
CAT AAT GTT TGG GCC ACA CAA GCC TGT GTA CCC ACA GAC CCC AAC CCA    6479
His Asn Val Trp Ala Thr Gln Ala Cys Val Pro Thr Asp Pro Asn Pro
 65              70                  75                  80

CAA GAA GTA GAA TTG GTA AAT GTG ACA GAA AAT TTT AAC ATG TGG AAA    6527
Gln Glu Val Glu Leu Val Asn Val Thr Glu Asn Phe Asn Met Trp Lys
                     85                  90                  95

AAT AAC ATG GTA GAA CAG ATG CAT GAG GAT ATA ATC AGT TTA TGG GAT    6575
Asn Asn Met Val Glu Gln Met His Glu Asp Ile Ile Ser Leu Trp Asp
            100                 105                 110

CAA AGC CTA AAG CCA TGT GTA AAA TTA ACC CCA CTC TGT GTT ACT TTA    6623
Gln Ser Leu Lys Pro Cys Val Lys Leu Thr Pro Leu Cys Val Thr Leu
        115                 120                 125

AAT TGC ACT GAT TTG AGG AAT ACT ACT AAT ACC AAT AAT AGT ACT GCT    6671
Asn Cys Thr Asp Leu Arg Asn Thr Thr Asn Thr Asn Asn Ser Thr Ala
    130                 135                 140

AAT AAC AAT AGT AAT AGC GAG GGA ACA ATA AAG GGA GGA GAA ATG AAA    6719
Asn Asn Asn Ser Asn Ser Glu Gly Thr Ile Lys Gly Gly Glu Met Lys
145                 150                 155                 160

AAC TGC TCT TTC AAT ATC ACC ACA AGC ATA AGA GAT AAG ATG CAG AAA    6767
Asn Cys Ser Phe Asn Ile Thr Thr Ser Ile Arg Asp Lys Met Gln Lys
                165                 170                 175

GAA TAT GCA CTT CTT TAT AAA CTT GAT ATA GTA TCA ATA GAT AAT GAT    6815
Glu Tyr Ala Leu Leu Tyr Lys Leu Asp Ile Val Ser Ile Asp Asn Asp
            180                 185                 190

AGT ACC AGC TAT AGG TTG ATA AGT TGT AAT ACC TCA GTC ATT ACA CAA    6863
Ser Thr Ser Tyr Arg Leu Ile Ser Cys Asn Thr Ser Val Ile Thr Gln
        195                 200                 205

GCT TGT CCA AAG ATA TCC TTT GAG CCA ATT CCC ATA CAC TAT TGT GCC    6911
Ala Cys Pro Lys Ile Ser Phe Glu Pro Ile Pro Ile His Tyr Cys Ala
    210                 215                 220

CCG GCT GGT TTT GCG ATT CTA AAA TGT AAC GAT AAA AAG TTC AGT GGA    6959
Pro Ala Gly Phe Ala Ile Leu Lys Cys Asn Asp Lys Lys Phe Ser Gly
225                 230                 235                 240

AAA GGA TCA TGT AAA AAT GTC AGC ACA GTA CAA TGT ACA CAT GGA ATT    7007
Lys Gly Ser Cys Lys Asn Val Ser Thr Val Gln Cys Thr His Gly Ile
                245                 250                 255

AGG CCA GTA GTA TCA ACT CAA CTG CTG TTA AAT GGC AGT CTA GCA GAA    7055
Arg Pro Val Val Ser Thr Gln Leu Leu Leu Asn Gly Ser Leu Ala Glu
            260                 265                 270

GAA GAG GTA GTA ATT AGA TCT GAG AAT TTC ACT GAT AAT GCT AAA ACC    7103
Glu Glu Val Val Ile Arg Ser Glu Asn Phe Thr Asp Asn Ala Lys Thr
        275                 280                 285

ATC ATA GTA CAT CTG AAT GAA TCT GTA CAA ATT AAT TGT ACA AGA CCC    7151
Ile Ile Val His Leu Asn Glu Ser Val Gln Ile Asn Cys Thr Arg Pro
    290                 295                 300

AAC TAC AAT AAA AGA AAA AGG ATA CAT ATA GGA CCA GGG AGA GCA TTT    7199
Asn Tyr Asn Lys Arg Lys Arg Ile His Ile Gly Pro Gly Arg Ala Phe
305                 310                 315                 320

TAT ACA ACA AAA AAT ATA ATA GGA ACT ATA AGA CAA GCA CAT TGT AAC    7247
Tyr Thr Thr Lys Asn Ile Ile Gly Thr Ile Arg Gln Ala His Cys Asn
                325                 330                 335

ATT AGT AGA GCA AAA TGG AAT GAC ACT TTA AGA CAG ATA GTT AGC AAA    7295
Ile Ser Arg Ala Lys Trp Asn Asp Thr Leu Arg Gln Ile Val Ser Lys
            340                 345                 350

TTA AAA GAA CAA TTT AAG AAT AAA ACA ATA GTC TTT AAT CAA TCC TCA    7343
Leu Lys Glu Gln Phe Lys Asn Lys Thr Ile Val Phe Asn Gln Ser Ser
        355                 360                 365

GGA GGG GAC CCA GAA ATT GTA ATG CAC AGT TTT AAT TGT GGA GGG GAA    7391
Gly Gly Asp Pro Glu Ile Val Met His Ser Phe Asn Cys Gly Gly Glu
    370                 375                 380
```

| | | | | | | | | | | | | | | | | |
|---|---|---|---|---|---|---|---|---|---|---|---|---|---|---|---|---|
| TTT | TTC | TAC | TGT | AAT | ACA | TCA | CCA | CTG | TTT | AAT | AGT | ACT | TGG | AAT | GGT | 7439 |
| Phe | Phe | Tyr | Cys | Asn | Thr | Ser | Pro | Leu | Phe | Asn | Ser | Thr | Trp | Asn | Gly | |
| 385 | | | | 390 | | | | | 395 | | | | | | 400 | |
| AAT | AAT | ACT | TGG | AAT | AAT | ACT | ACA | GGG | TCA | AAT | AAC | AAT | ATC | ACA | CTT | 7487 |
| Asn | Asn | Thr | Trp | Asn | Asn | Thr | Thr | Gly | Ser | Asn | Asn | Asn | Ile | Thr | Leu | |
| | | | | 405 | | | | 410 | | | | | 415 | | | |
| CAA | TGC | AAA | ATA | AAA | CAA | ATT | ATA | AAC | ATG | TGG | CAG | GAA | GTA | GGA | AAA | 7535 |
| Gln | Cys | Lys | Ile | Lys | Gln | Ile | Ile | Asn | Met | Trp | Gln | Glu | Val | Gly | Lys | |
| | | | 420 | | | | | 425 | | | | | 430 | | | |
| GCA | ATG | TAT | GCC | CCT | CCC | ATT | GAA | GGA | CAA | ATT | AGA | TGT | TCA | TCA | AAT | 7583 |
| Ala | Met | Tyr | Ala | Pro | Pro | Ile | Glu | Gly | Gln | Ile | Arg | Cys | Ser | Ser | Asn | |
| | | 435 | | | | 440 | | | | | | 445 | | | | |
| ATT | ACA | GGG | CTA | CTA | TTA | ACA | AGA | GAT | GGT | GGT | AAG | GAC | ACG | GAC | ACG | 7631 |
| Ile | Thr | Gly | Leu | Leu | Leu | Thr | Arg | Asp | Gly | Gly | Lys | Asp | Thr | Asp | Thr | |
| | | 450 | | | | 455 | | | | | 460 | | | | | |
| AAC | GAC | ACC | GAG | ATC | TTC | AGA | CCT | GGA | GGA | GGA | GAT | ATG | AGG | GAC | AAT | 7679 |
| Asn | Asp | Thr | Glu | Ile | Phe | Arg | Pro | Gly | Gly | Gly | Asp | Met | Arg | Asp | Asn | |
| 465 | | | | | 470 | | | | | 475 | | | | | 480 | |
| TGG | AGA | AGT | GAA | TTA | TAT | AAA | TAT | AAA | GTA | GTA | ACA | ATT | GAA | CCA | TTA | 7727 |
| Trp | Arg | Ser | Glu | Leu | Tyr | Lys | Tyr | Lys | Val | Val | Thr | Ile | Glu | Pro | Leu | |
| | | | | 485 | | | | | 490 | | | | | 495 | | |
| GGA | GTA | GCA | CCC | ACC | AAG | GCA | AAG | AGA | AGA | GTG | GTG | CAG | AGA | GAA | AAA | 7775 |
| Gly | Val | Ala | Pro | Thr | Lys | Ala | Lys | Arg | Arg | Val | Val | Gln | Arg | Glu | Lys | |
| | | | 500 | | | | | 505 | | | | | 510 | | | |
| AGA | GCA | GCG | ATA | GGA | GCT | CTG | TTC | CTT | GGG | TTC | TTA | GGA | GCA | GCA | GGA | 7823 |
| Arg | Ala | Ala | Ile | Gly | Ala | Leu | Phe | Leu | Gly | Phe | Leu | Gly | Ala | Ala | Gly | |
| | | 515 | | | | 520 | | | | | 525 | | | | | |
| AGC | ACT | ATG | GGC | GCA | GCG | TCA | GTG | ACG | CTG | ACG | GTA | CAG | GCC | AGA | CTA | 7871 |
| Ser | Thr | Met | Gly | Ala | Ala | Ser | Val | Thr | Leu | Thr | Val | Gln | Ala | Arg | Leu | |
| | | 530 | | | | 535 | | | | | 540 | | | | | |
| TTA | TTG | TCT | GGT | ATA | GTG | CAA | CAG | CAG | AAC | AAT | TTG | CTG | AGG | GCC | ATT | 7919 |
| Leu | Leu | Ser | Gly | Ile | Val | Gln | Gln | Gln | Asn | Asn | Leu | Leu | Arg | Ala | Ile | |
| 545 | | | | | 550 | | | | | 555 | | | | | 560 | |
| GAG | GCG | CAA | CAG | CAT | ATG | TTG | CAA | CTC | ACA | GTC | TGG | GGC | ATC | AAG | CAG | 7967 |
| Glu | Ala | Gln | Gln | His | Met | Leu | Gln | Leu | Thr | Val | Trp | Gly | Ile | Lys | Gln | |
| | | | | 565 | | | | | 570 | | | | | 575 | | |
| CTC | CAG | GCA | AGA | GTC | CTG | GCT | GTG | GAA | AGA | TAC | CTA | AAG | GAT | CAA | CAG | 8015 |
| Leu | Gln | Ala | Arg | Val | Leu | Ala | Val | Glu | Arg | Tyr | Leu | Lys | Asp | Gln | Gln | |
| | | | 580 | | | | | 585 | | | | | 590 | | | |
| CTC | CTG | GGG | TTT | TGG | GGT | TGC | TCT | GGA | AAA | CTC | ATT | TGC | ACC | ACT | ACT | 8063 |
| Leu | Leu | Gly | Phe | Trp | Gly | Cys | Ser | Gly | Lys | Leu | Ile | Cys | Thr | Thr | Thr | |
| | | 595 | | | | 600 | | | | | 605 | | | | | |
| GTG | CCT | TGG | AAT | GCT | AGT | TGG | AGT | AAT | AAA | TCT | CTG | GAT | GAT | ATT | TGG | 8111 |
| Val | Pro | Trp | Asn | Ala | Ser | Trp | Ser | Asn | Lys | Ser | Leu | Asp | Asp | Ile | Trp | |
| | 610 | | | | 615 | | | | | 620 | | | | | | |
| AAT | AAC | ATG | ACC | TGG | ATG | CAG | TGG | GAA | AGA | GAA | ATT | GAC | AAT | TAC | ACA | 8159 |
| Asn | Asn | Met | Thr | Trp | Met | Gln | Trp | Glu | Arg | Glu | Ile | Asp | Asn | Tyr | Thr | |
| 625 | | | | 630 | | | | 635 | | | | | | | 640 | |
| AGC | TTA | ATA | TAC | TCA | TTA | CTA | GAA | AAA | TCG | CAA | ACC | CAA | CAA | GAA | AAG | 8207 |
| Ser | Leu | Ile | Tyr | Ser | Leu | Leu | Glu | Lys | Ser | Gln | Thr | Gln | Gln | Glu | Lys | |
| | | | | 645 | | | | | 650 | | | | | 655 | | |
| AAT | GAA | CAA | GAA | TTA | TTG | GAA | TTG | GAT | AAA | TGG | GCA | AGT | TTG | TGG | AAT | 8255 |
| Asn | Glu | Gln | Glu | Leu | Leu | Glu | Leu | Asp | Lys | Trp | Ala | Ser | Leu | Trp | Asn | |
| | | | | 660 | | | | | 665 | | | | | 670 | | |
| TGG | TTT | GAC | ATA | ACA | AAT | TGG | CTG | TGG | TAT | ATA | AAA | ATA | TTC | ATA | ATG | 8303 |
| Trp | Phe | Asp | Ile | Thr | Asn | Trp | Leu | Trp | Tyr | Ile | Lys | Ile | Phe | Ile | Met | |
| | | | 675 | | | | | 680 | | | | | 685 | | | |
| ATA | GTA | GGA | GGC | TTG | GTA | GGT | TTA | AGA | ATA | GTT | TTT | GCT | GTA | CTT | TCT | 8351 |
| Ile | Val | Gly | Gly | Leu | Val | Gly | Leu | Arg | Ile | Val | Phe | Ala | Val | Leu | Ser | |
| | | 690 | | | | 695 | | | | | 700 | | | | | |
| ATA | GTG | AAT | AGA | GTT | AGG | CAG | GGA | TAC | TCA | CCA | TTG | TCG | TTG | CAG | ACC | 8399 |
| Ile | Val | Asn | Arg | Val | Arg | Gln | Gly | Tyr | Ser | Pro | Leu | Ser | Leu | Gln | Thr | |

|     |     |     |     |     |     |     |     |     |     |     |     |     |     |     |     |
|-----|-----|-----|-----|-----|-----|-----|-----|-----|-----|-----|-----|-----|-----|-----|-----|
| 705 |     |     |     |     | 710 |     |     |     |     | 715 |     |     |     | 720 |     |
| CGC | CCC | CCA | GTT | CCG | AGG | GGA | CCC | GAC | AGG | CCC | GAA | GGA | ATC | GAA | GAA | 8447 |
| Arg | Pro | Pro | Val | Pro | Arg | Gly | Pro | Asp | Arg | Pro | Glu | Gly | Ile | Glu | Glu |
|     |     |     |     | 725 |     |     |     |     | 730 |     |     |     |     | 735 |     |
| GAA | GGT | GGA | GAG | AGA | GAC | AGA | GAC | ACA | TCC | GGT | CGA | TTA | GTG | CAT | GGA | 8495 |
| Glu | Gly | Gly | Glu | Arg | Asp | Arg | Asp | Thr | Ser | Gly | Arg | Leu | Val | His | Gly |
|     |     |     | 740 |     |     |     |     | 745 |     |     |     |     | 750 |     |     |
| TTC | TTA | GCA | ATT | ATC | TGG | GTC | GAC | CTG | CGG | AGC | CTG | TTC | CTC | TTC | AGC | 8543 |
| Phe | Leu | Ala | Ile | Ile | Trp | Val | Asp | Leu | Arg | Ser | Leu | Phe | Leu | Phe | Ser |
|     |     |     | 755 |     |     |     |     | 760 |     |     |     |     | 765 |     |     |
| TAC | CAC | CAC | AGA | GAC | TTA | CTC | TTG | ATT | GCA | GCG | AGG | ATT | GTG | GAA | CTT | 8591 |
| Tyr | His | His | Arg | Asp | Leu | Leu | Leu | Ile | Ala | Ala | Arg | Ile | Val | Glu | Leu |
|     |     | 770 |     |     |     |     | 775 |     |     |     |     | 780 |     |     |     |
| CTG | GGA | CGC | AGG | GGG | TGG | GAA | GTC | CTC | AAA | TAT | TGG | TGG | AAT | CTC | CTA | 8639 |
| Leu | Gly | Arg | Arg | Gly | Trp | Glu | Val | Leu | Lys | Tyr | Trp | Trp | Asn | Leu | Leu |
| 785 |     |     |     |     | 790 |     |     |     |     | 795 |     |     |     |     | 800 |
| CAG | TAT | TGG | AGT | CAG | GAA | CTA | AAG | AGT | AGT | GCT | GTT | AGC | TTG | CTT | AAT | 8687 |
| Gln | Tyr | Trp | Ser | Gln | Glu | Leu | Lys | Ser | Ser | Ala | Val | Ser | Leu | Leu | Asn |
|     |     |     |     | 805 |     |     |     |     | 810 |     |     |     |     | 815 |     |
| GCC | ACA | GCT | ATA | GCA | GTA | GCT | GAG | GGG | ACA | GAT | AGG | GTT | ATA | GAA | GTA | 8735 |
| Ala | Thr | Ala | Ile | Ala | Val | Ala | Glu | Gly | Thr | Asp | Arg | Val | Ile | Glu | Val |
|     |     |     | 820 |     |     |     |     | 825 |     |     |     |     | 830 |     |     |
| CTG | CAA | AGA | GCT | GGT | AGA | GCT | ATT | CTC | CAC | ATA | CCT | ACA | AGA | ATA | AGA | 8783 |
| Leu | Gln | Arg | Ala | Gly | Arg | Ala | Ile | Leu | His | Ile | Pro | Thr | Arg | Ile | Arg |
|     |     | 835 |     |     |     |     | 840 |     |     |     |     | 845 |     |     |     |
| CAG | GGC | TTG | GAA | AGG | GCT | TTG | CTA | TAAGATGGGT | GGCAAATGGT | CAAAACGTGT | 8837 |
| Gln | Gly | Leu | Glu | Arg | Ala | Leu | Leu |
|     | 850 |     |     |     |     | 855 |     |

| | |
|---|---|
| GACTGGATGG CCTACTGTAA GGGAAAGAAT GAGACGAGCT GAACCAGCTG AGCTAGCAGC | 8897 |
| AGATGGGGTG GGAGCAGCAT CCCGAGACCT GGAAAAACAT GGAGCACTCA CAAGTAGCAA | 8957 |
| TACAGCAGCT ACCAATGCTG ATTGTGCCTG GCTAGAAGCA CAAGAGGAGG AGGAAGTGGG | 9017 |
| TTTTCCAGTC AAACCTCAGG TACCTTTAAG ACCAATGACT TACAAAGCAG CTTTAGATCT | 9077 |
| TAGCCACTTT TTAAAAGAAA AGGGGGGACT GGATGGGTTA ATTTACTCCC AAAAGAGACA | 9137 |
| AGACATCCTT GATCTGTGGG TCTACCACAC ACAAGGCTAC TTCCCTGATT GGCAGAACTA | 9197 |
| CACACCAGGG CCAGGGATCA GATATCCACT GACCTTTGGA TGGTGCTTCA AGCTAGTACC | 9257 |
| AGTTGAGCCA GAGAAGATAG AAGAGGCCAA TAAAGGAGAG AACAACTGCT TGTTACACCC | 9317 |
| TATGAGCCAG CATGGATGGA TGACCCGGAG AGAGAAGTGT TAGTGTGGAA GTCTGACAGC | 9377 |
| CACCTAGCAT TCAGCATTA TGCCCGAGAG CTGCATCGG AGTACTACAA GAACTGCTGA | 9437 |
| CATCGAGCTA TCTACAAGGG ACTTTCCGCT GGGGACTTTC CAGGGAGGTG TGGCCTGGGC | 9497 |
| GGGACCGGGG AGTGGCGAGC CCTCAGATCG TGCATATAAG CAGCTGCTTT CTGCCTGTAC | 9557 |
| TGGGTCTCTC TGGTTAGACC AGATCTGAGC CTGGGAGCTC TCTGGCTAAC TAGGGAACCC | 9617 |
| ACTGCTTAAG CCTCAATAAA GCTTGCCTTG AGTGCTTCAA GTAGTGTGTG CCCGTCTGTT | 9677 |
| ATGTGACTCT GGTAGCTAGA GATCCCTCAG ATCCTTTTAG GCAGTGTGGA AAATCTCTAG | 9737 |
| CA | 9739 |

( 2 ) INFORMATION FOR SEQ ID NO:2:

( i ) SEQUENCE CHARACTERISTICS:
        ( A ) LENGTH: 856 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

-continued

| | | | | | | | | | | | | | | |
|---|---|---|---|---|---|---|---|---|---|---|---|---|---|---|
| Met | Arg | Val | Lys | Gly | Ile | Arg | Arg | Asn | Tyr | Gln | His | Trp | Trp | Gly | Trp |
| 1 | | | | 5 | | | | | 10 | | | | | 15 | |
| Gly | Thr | Met | Leu | Leu | Gly | Leu | Leu | Met | Ile | Cys | Ser | Ala | Thr | Glu | Lys |
| | | | 20 | | | | | 25 | | | | | 30 | | |
| Leu | Trp | Val | Thr | Val | Tyr | Tyr | Gly | Val | Pro | Val | Trp | Lys | Glu | Ala | Thr |
| | | 35 | | | | | 40 | | | | | 45 | | | |
| Thr | Thr | Leu | Phe | Cys | Ala | Ser | Asp | Ala | Lys | Ala | Tyr | Asp | Thr | Glu | Val |
| | 50 | | | | | 55 | | | | | 60 | | | | |
| His | Asn | Val | Trp | Ala | Thr | Gln | Ala | Cys | Val | Pro | Thr | Asp | Pro | Asn | Pro |
| 65 | | | | | 70 | | | | | 75 | | | | | 80 |
| Gln | Glu | Val | Glu | Leu | Val | Asn | Val | Thr | Glu | Asn | Phe | Asn | Met | Trp | Lys |
| | | | | 85 | | | | | 90 | | | | | 95 | |
| Asn | Asn | Met | Val | Glu | Gln | Met | His | Glu | Asp | Ile | Ile | Ser | Leu | Trp | Asp |
| | | | 100 | | | | | 105 | | | | | 110 | | |
| Gln | Ser | Leu | Lys | Pro | Cys | Val | Lys | Leu | Thr | Pro | Leu | Cys | Val | Thr | Leu |
| | | 115 | | | | | 120 | | | | | 125 | | | |
| Asn | Cys | Thr | Asp | Leu | Arg | Asn | Thr | Thr | Asn | Thr | Asn | Asn | Ser | Thr | Ala |
| | 130 | | | | | 135 | | | | | 140 | | | | |
| Asn | Asn | Asn | Ser | Asn | Ser | Glu | Gly | Thr | Ile | Lys | Gly | Gly | Glu | Met | Lys |
| 145 | | | | | 150 | | | | | 155 | | | | | 160 |
| Asn | Cys | Ser | Phe | Asn | Ile | Thr | Thr | Ser | Ile | Arg | Asp | Lys | Met | Gln | Lys |
| | | | | 165 | | | | | 170 | | | | | 175 | |
| Glu | Tyr | Ala | Leu | Leu | Tyr | Lys | Leu | Asp | Ile | Val | Ser | Ile | Asp | Asn | Asp |
| | | | 180 | | | | | 185 | | | | | 190 | | |
| Ser | Thr | Ser | Tyr | Arg | Leu | Ile | Ser | Cys | Asn | Thr | Ser | Val | Ile | Thr | Gln |
| | | 195 | | | | | 200 | | | | | 205 | | | |
| Ala | Cys | Pro | Lys | Ile | Ser | Phe | Glu | Pro | Ile | Pro | Ile | His | Tyr | Cys | Ala |
| | 210 | | | | | 215 | | | | | 220 | | | | |
| Pro | Ala | Gly | Phe | Ala | Ile | Leu | Lys | Cys | Asn | Asp | Lys | Lys | Phe | Ser | Gly |
| 225 | | | | | 230 | | | | | 235 | | | | | 240 |
| Lys | Gly | Ser | Cys | Lys | Asn | Val | Ser | Thr | Val | Gln | Cys | Thr | His | Gly | Ile |
| | | | | 245 | | | | | 250 | | | | | 255 | |
| Arg | Pro | Val | Val | Ser | Thr | Gln | Leu | Leu | Leu | Asn | Gly | Ser | Leu | Ala | Glu |
| | | | 260 | | | | | 265 | | | | | 270 | | |
| Glu | Glu | Val | Val | Ile | Arg | Ser | Glu | Asn | Phe | Thr | Asp | Asn | Ala | Lys | Thr |
| | | 275 | | | | | 280 | | | | | 285 | | | |
| Ile | Ile | Val | His | Leu | Asn | Glu | Ser | Val | Gln | Ile | Asn | Cys | Thr | Arg | Pro |
| | 290 | | | | | 295 | | | | | 300 | | | | |
| Asn | Tyr | Asn | Lys | Arg | Lys | Arg | Ile | His | Ile | Gly | Pro | Gly | Arg | Ala | Phe |
| 305 | | | | | 310 | | | | | 315 | | | | | 320 |
| Tyr | Thr | Thr | Lys | Asn | Ile | Ile | Gly | Thr | Ile | Arg | Gln | Ala | His | Cys | Asn |
| | | | | 325 | | | | | 330 | | | | | 335 | |
| Ile | Ser | Arg | Ala | Lys | Trp | Asn | Asp | Thr | Leu | Arg | Gln | Ile | Val | Ser | Lys |
| | | | 340 | | | | | 345 | | | | | 350 | | |
| Leu | Lys | Glu | Gln | Phe | Lys | Asn | Lys | Thr | Ile | Val | Phe | Asn | Gln | Ser | Ser |
| | | 355 | | | | | 360 | | | | | 365 | | | |
| Gly | Gly | Asp | Pro | Glu | Ile | Val | Met | His | Ser | Phe | Asn | Cys | Gly | Gly | Glu |
| | 370 | | | | | 375 | | | | | 380 | | | | |
| Phe | Phe | Tyr | Cys | Asn | Thr | Ser | Pro | Leu | Phe | Asn | Ser | Thr | Trp | Asn | Gly |
| 385 | | | | | 390 | | | | | 395 | | | | | 400 |
| Asn | Asn | Thr | Trp | Asn | Thr | Thr | Gly | Ser | Asn | Asn | Asn | Ile | Thr | Leu |
| | | | | 405 | | | | | 410 | | | | | 415 | |
| Gln | Cys | Lys | Ile | Lys | Gln | Ile | Ile | Asn | Met | Trp | Gln | Glu | Val | Gly | Lys |
| | | | 420 | | | | | 425 | | | | | 430 | | |
| Ala | Met | Tyr | Ala | Pro | Pro | Ile | Glu | Gly | Gln | Ile | Arg | Cys | Ser | Ser | Asn |

|     |     |     |     |     |     |     |     |     |     |     |     |     |     |     |
| --- | --- | --- | --- | --- | --- | --- | --- | --- | --- | --- | --- | --- | --- | --- |
|     |     |     | 435 |     |     |     | 440 |     |     |     | 445 |     |     |     |
| Ile | Thr 450 | Gly | Leu | Leu | Leu | Thr 455 | Arg | Asp | Gly | Gly | Lys 460 | Asp | Thr | Asp | Thr |
| Asn 465 | Asp | Thr | Glu | Ile | Phe 470 | Arg | Pro | Gly | Gly | Gly 475 | Asp | Met | Arg | Asp | Asn 480 |
| Trp | Arg | Ser | Glu | Leu 485 | Tyr | Lys | Tyr | Lys | Val 490 | Val | Thr | Ile | Glu | Pro 495 | Leu |
| Gly | Val | Ala | Pro 500 | Thr | Lys | Ala | Lys | Arg 505 | Arg | Val | Val | Gln | Arg 510 | Glu | Lys |
| Arg | Ala | Ala 515 | Ile | Gly | Ala | Leu | Phe 520 | Leu | Gly | Phe | Leu | Gly 525 | Ala | Ala | Gly |
| Ser | Thr 530 | Met | Gly | Ala | Ala | Ser 535 | Val | Thr | Leu | Thr | Val 540 | Gln | Ala | Arg | Leu |
| Leu 545 | Leu | Ser | Gly | Ile | Val 550 | Gln | Gln | Asn | Asn 555 | Leu | Leu | Arg | Ala | Ile 560 |
| Glu | Ala | Gln | Gln | His 565 | Met | Leu | Gln | Leu | Thr 570 | Val | Trp | Gly | Ile | Lys 575 | Gln |
| Leu | Gln | Ala | Arg 580 | Val | Leu | Ala | Val | Glu 585 | Arg | Tyr | Leu | Lys | Asp 590 | Gln | Gln |
| Leu | Leu | Gly 595 | Phe | Trp | Gly | Cys | Ser 600 | Gly | Lys | Leu | Ile | Cys 605 | Thr | Thr | Thr |
| Val | Pro 610 | Trp | Asn | Ala | Ser | Trp 615 | Ser | Asn | Lys | Ser | Leu 620 | Asp | Asp | Ile | Trp |
| Asn 625 | Asn | Met | Thr | Trp | Met 630 | Gln | Trp | Glu | Arg | Glu 635 | Ile | Asp | Asn | Tyr | Thr 640 |
| Ser | Leu | Ile | Tyr | Ser 645 | Leu | Leu | Glu | Lys | Ser 650 | Gln | Thr | Gln | Gln | Glu 655 | Lys |
| Asn | Glu | Gln | Glu 660 | Leu | Leu | Glu | Leu | Asp 665 | Lys | Trp | Ala | Ser | Leu 670 | Trp | Asn |
| Trp | Phe | Asp 675 | Ile | Thr | Asn | Trp | Leu 680 | Trp | Tyr | Ile | Lys | Ile 685 | Phe | Ile | Met |
| Ile | Val 690 | Gly | Gly | Leu | Val | Gly 695 | Leu | Arg | Ile | Val | Phe 700 | Ala | Val | Leu | Ser |
| Ile 705 | Val | Asn | Arg | Val | Arg 710 | Gln | Gly | Tyr | Ser | Pro 715 | Leu | Ser | Leu | Gln | Thr 720 |
| Arg | Pro | Pro | Val | Pro 725 | Arg | Gly | Pro | Asp | Arg 730 | Pro | Glu | Gly | Ile | Glu 735 | Glu |
| Glu | Gly | Gly | Glu 740 | Arg | Asp | Arg | Asp | Thr 745 | Ser | Gly | Arg | Leu | Val 750 | His | Gly |
| Phe | Leu | Ala 755 | Ile | Ile | Trp | Val | Asp 760 | Leu | Arg | Ser | Leu | Phe 765 | Leu | Phe | Ser |
| Tyr | His 770 | His | Arg | Asp | Leu | Leu 775 | Leu | Ile | Ala | Ala | Arg 780 | Ile | Val | Glu | Leu |
| Leu 785 | Gly | Arg | Arg | Gly | Trp 790 | Glu | Val | Leu | Lys | Tyr 795 | Trp | Trp | Asn | Leu | Leu 800 |
| Gln | Tyr | Trp | Ser | Gln 805 | Glu | Leu | Lys | Ser | Ser 810 | Ala | Val | Ser | Leu | Leu 815 | Asn |
| Ala | Thr | Ala | Ile 820 | Ala | Val | Ala | Glu | Gly 825 | Thr | Asp | Arg | Val | Ile 830 | Glu | Val |
| Leu | Gln | Arg 835 | Ala | Gly | Arg | Ala | Ile 840 | Leu | His | Ile | Pro | Thr 845 | Arg | Ile | Arg |
| Gln | Gly 850 | Leu | Glu | Arg | Ala | Leu 855 | Leu |     |     |     |     |     |     |     |     |

( 2 ) INFORMATION FOR SEQ ID NO:3:

-continued ( i ) SEQUENCE CHARACTERISTICS:
    ( A ) LENGTH: 9746 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 6243..8816

( x i ) SEQUENCE DESCRIPTION: SEQ ID NO:3:

```
TGGATGGGTT AATTTACTCC CAAAGAGACA AGACATCCTT GATCTGTGGG TCTACCACAC    60
ACAAGGCTAC TTCCCTGATT GGCAGAACTA CACACCAGGG CCAGGGATCA GATATCCACT   120
GACCTTTGGA TGGTGCTTCA AGCTAGTACC AGTTGAGCCA GAGAAGATAG AAGAGGCCAA   180
TAAAGGAGAG AACAACTGCT TGTTACACCC TATGAGCCAG CATGGGATGG ATGACCCGGA   240
GAGAGAAGTG TTAGTGTGGA AGTCTGACAG CCACCTAGCA TTTCAGCATT ATGCCCGAGA   300
GCTGCATCCG GAGTACTACA AGAACTGCTG ACATCGAGCT ATCTACAAGG ACTTTCCGC    360
TGGGGACTTT CCAGGGAGGT GTGGCCTGGG CGGGACCGGG GAGTGGCGAG CCCTCAGATG   420
CTGCATATAA GCAGCTGCTT TCTGCCTGTA CTGGGTCTCT CTGGTTAGAC CAGATCTGAG   480
CCTGGGAGCT CTCTGGCTAA CTAGGGAACC CACTGCTTAA GCCTCAATAA AGCTTGCCTT   540
GAGTGCTTCA AGTAGTGTGT GCCCGTCTGT TATGTGACTC TGGTAGCTAG AGATCCCTCA   600
GATCCTTTTA GGCAGTGTGG AAAATCTCTA GCAGTGGCGC CCGAACAGGG ACTTGAAAGC   660
GAAAGAGAAA CCAGAGGAGC TCTCTCGACG CAGGACTCGG CTTGCTGAAG CGCGCACGGC   720
AAGAGGCGAG GGGCGGCGAC TGGTGAGTAC GCCAAAATTC TTGACTAGCG GAGGCTAGAA   780
GGAGAGAGAT GGGTGCGAGA GCGTCGGTAT TAAGCGGGGG AGAATTAGAT CGATGGGAAA   840
AAATTCGGTT AAGGCCAGGG GGAAAGAAAA AATATAAATT AAAACATGTA GTATGGGCAA   900
GCAGGGAGCT AGAACGATTC GCAGTCAATC CTGGCCTGTT AGAAACATCA GAAGGCTGTA   960
GACAAATACT GGGACAGCTA CAACCATCCC TTCAGACAGG ATCAGAAGAA CTTAAATCAT  1020
TATATAATAC AGTAGCAACC CTCTATTGTG TGCATCAAAA GATAGAGATA AAGACACCA   1080
AGGAAGCTTT AGAGAAAATA GAGGAAGAGC AAAACAAAAG TAAGAAAAAA GCACAGCAAG  1140
CAGTAGCTGA CACAGGAAAC AGAGGAAACA GCAGCCAAGT CAGCCAAAAT TACCCCATAG  1200
TGCAGAACAT CCAGGGGCAA ATGGTACATC AGGCCATATC ACCTAGAACT TTAAATGCAT  1260
GGGTAAAAGT AGTAGAAGAG AAGGCTTTCA GCCCAGAAGT AATACCCATG TTTTCAGCAT  1320
TATCAGAAGG AGCCACCCCA CAAGATTTAA ACACCATGCT AAACACAGTG GGGGGACATC  1380
AAGCAGCCAT GCAAATGTTA AAAGAGACCA TCAATGAGGA AGCTGCAGAA TGGGATAGAT  1440
TGCATCCAGT GCATGCAGGG CCTATTGCAC CAGGCCAGAT GAGAGAACCA AGGGGAAGTG  1500
ACATAGCAGG AACTACTAGT ACCCTTCAGG AACAAATAGG ATGGATGACA AATAATCCAC  1560
CTATCCCAGT AGGAGAAATC TATAAAAGAT GGATAATCCT GGGATTAAAT AAAATAGTAA  1620
GGATGTATAG CCCTTCCAGC ATTCTGGACA TAAGACAAGG ACCAAGGAA CCCTTTAGAG   1680
ACTATGTAGA CCGGTTCTAT AAAACTCTAA GAGCCGAGCA AGCTTCACAG GAGGTAAAAA  1740
ATTGGATGAC AGAAACCTTG TTGGTCCAAA ATGCGAACCC AGATTGTAAG ACTATTTAA   1800
AAGCATTGGG ACCAGCAGCT ACACTAGAAG AAATGATGAC AGCATGTCAG GGAGTGGGAG  1860
GACCTGGTCA TAAAGCAAGA GTTTTGGCGG AAGCGATGAG CCAAGTAACA AATTCAGCTA  1920
CCATAATGAT GCAGAGAGGC AATTTTAGGA ATCAAAGAAA GATTATCAAG TGCTTCAATT  1980
GTGGCAAAGA AGGGCACATA GCCAAAAATT GCAGGGCCCC TAGGAAAAGG GGCTGTTGGA  2040
AATGTGGAAA GGAAGGACAC CAAATGAAAG ATTGTACTGA GAGACAGGCT AATTTTTTAG  2100
```

```
GGAAGATCTG GCCTTCCTGC AAGGGAAGGC AGGGAATTTT CCTCAGAGCA GAACAGAGCC    2160
AACAGCCCCA CCAGAAGAGA GCTTCAGGTT TGGGGAAGAG ACAACAACTC CCTATCAGAA    2220
GCAGGAGAAG AAGCAGGAGA CGATAGACAA GGACCTGTAT CCTTTAGCTT CCCTCAAATC    2280
ACTCTTTGGC AACGACCCAT TGTCACAATA AGATAGGGG GGCAACTAAA GGAAGCTCTA    2340
TTAGATACAG GAGCAGATGA TACAGTATTA GAAGAAATGA ATTTGCCAGG AAGATGGAAA    2400
CCAAAAATGA TAGGGGGAAT TGGAGGTTTT ATCAAAGTAA GACAGTATGA TCAGATAACC    2460
ATAGAAATCT GTGGACATAA AGCTATAGGT ACAGTATTAG TAGGACCTAC ACCTGTCAAC    2520
ATAATTGGAA GAAATCTGTT GACTCAGCTT GGGTGCACTT TAAATTTTCC CATTAGTCCT    2580
ATTGAAACTG TACCAGTAAA ATTAAAGCCA GGAATGGATG GCCCAAAAGT TAAACAATGG    2640
CCATTGACAG AAGAAAAAAT AAAAGCATTA ATAGAAATTT GTACAGAAAT GGAAAAGGAA    2700
GGGAAAATTT CAAAAATTGG GCCTGAAAAT CCATACAATA CTCCAGTATT TGCCATAAAG    2760
AAAAAAGACA GTACTAAATG GAGAAAATTA GTAGATTTCA GAGAACTTAA TAAGAAAACT    2820
CAAGACTTCT GGGAAGTTCA ATTAGGAATA CCACATCCTG CAGGGTTAAA AAGAAAAAA    2880
TCAGTAACAG TACTGGATGT GGGTGATGCA TATTTTTCAG TTCCCTTAGA TAAAGACTTC    2940
AGGAAGTATA CTGCATTTAC CATACCTAGT ATAAACAATG AAACACCAGG GATTAGATAT    3000
CAGTACAATG TGCTTCCACA GGGATGGAAA GGATCACCAG CAATATTCCA AGTAGCATG    3060
ACAAAAATCT TAGAGCCTTT TAGAAAACAA AATCCAGACA TAGTTATCTA TCAATACATG    3120
GATGATTTGT ATGTAGGATC TGACTTAGAA ATAGGGCAGC ATAGAGCAAA AATAGAGGAA    3180
CTGAGACGAC ATCTGTTGAG GTGGGGATTT ACCACACCAG ACAAAAAACA TCAGAAAGAA    3240
CCTCCATTCC TTTGGATGGG TTATGAACTC CATCCTGATA AATGGACAGT ACAGCCTATA    3300
GTGCTGCCAG AAAAAGACAG CTGGACTGTC AATGACATAC AGAAGTTAGT GGGAAAATTG    3360
AATTGGGCAA GTCAAATTTA CGCAGGGATT AAAGTAAAGC AATTATGTAA ACTCCTTAGA    3420
GGAACCAAAG CACTAACAGA AGTAATACCA CTAACAGAAG AAGCAGAGCT AGAACTGGCA    3480
GAAAACAGGG AAATTCTAAA AGAACCAGTA CATGGAGTGT ATTATGACCC ATCAAAAGAC    3540
TTAATAGCAG AAGTACAGAA GCAGGGGCAA GGCCAATGGA CATATCAAAT TTATCAAGAG    3600
CCATTTAAAA ATCTGAAAAC AGGCAAATAT GCAAGAATGA GGGGTGCCCA CACTAATGAT    3660
GTAAAACAAT TAACAGAGGC AGTGCAAAAA ATAGCCACAG AAAGCATAGT AATATGGGGA    3720
AAGACTCCTA AATTTAGACT ACCCATACAA AAAGAAACAT GGGAAACATG GTGGACAGAG    3780
TATTGGCAAG CCACCTGGAT TCCTGAGTGG GAGTTTGTCA ATACCCCTCC CTTAGTGAAA    3840
TTATGGTACC AGTTAGAGAA AGAACCCATA GTAGGAGCAG AAACTTTCTA TGTAGATGGG    3900
GCAGCTAACA GGGAGACTAA AAAAGGAAAA GCAGGATATG TTACTAACAG AGGAAGACAA    3960
AAGGTTGTCT CCCTAACTGA CACAACAAAT CAGAAGACTG AGTTACAAGC AATTCATCTA    4020
GCTTTGCAAG ATTCAGGGTT AGAAGTAAAC ATAGTAACAG ACTCACAATA TGCATTAGGA    4080
ATCATTCAAG CACAACCAGA TAAAAGTGAA TCAGAGTTAG TCAGTCAAAT AATAGAGCAG    4140
TTAATAAAAA AGGAAAAGGT CTATCTGGCA TGGGTACCAG CACACAAAGG AATTGGAGGA    4200
AATGAACAAG TAGATAAATT AGTCAGTGCT GGAATCAGGA AAGTACTATT TTTAGATGGA    4260
ATAGATAAGG CCCAAGAAGA CCATGAGAAA TATCACAGTA ATTGGAGAGC AATGGCTAGT    4320
GACTTTAACC TACCACCTAT AGTAGCAAAA GAAATAGTAG CCAGCTGTGA TAAATGTCAG    4380
CTAAAAGGAG AAGCCATGCA TGGACAAGTA GACTGTAGTC CAGGAATATG GCAACTAGAT    4440
TGTACACATT TAGAAGGAAA AGTTATCCTG GTAGCAGTTC ATGTAGCCAG TGGATACATA    4500
GAAGCAGAAG TTATTCCAGC AGAGACAGGG CAGGAGACAG CATACTTTCT CTTAAAATTA    4560
```

```
GCAGGAAGAT GGCCAGTAAA AACAATACAT ACAGACAATG GCCCCAATTT CACCAGTACT   4620
ACGGTTAAGG CCGCCTGTTG GTGGGCGGGG ATCAAGCAGG AATTTGGCAT TCCCTACAAT   4680
CCCCAAAGTC AAGGAGTAAT AGAATCTATG AATAAAGAAT TAAAGAAAAT TATAGGACAG   4740
GTAAGAGATC AGGCTGAACA TCTTAAGACA GCAGTACAAA TGGCAGTATT CATCCACAAT   4800
TTTAAAAGAA AAGGGGGGAT TGGGGGGTAC AGTGCAGGGG AAAGAATAGT AGACATAATA   4860
GCAACAGACA TACAAACTAA AGAACTACAA AAACAAATTA CAAAAATTCA AAATTTTCGG   4920
GTTTATTACA GGGACAGCAG AGATCCACTT TGGAAAGGAC CAGCAAAGCT TCTCTGGAAA   4980
GGTGAAGGGG CAGTAGTAAT ACAAGATAAT AGTGACATAA AGTAGTGCC AAGAAGAAAA   5040
GCAAAGATCA TTAGGGATTA TGGAAAACAG ATGGCAGGTG ATGATTGTGT GGCAAGTAGA   5100
CAGGATGAGG ATTAGAACAT GGAAAAGTTT AGTAAAACAC CATATGTATA TTTCAAAGAA   5160
AGCTAAAGGA TGGTTTTATA GACATCACTA TGAAAGCACT CATCCAAGAA TAAGTTCAGA   5220
AGTACACATC CCACTAGGGG ATGCTAGATT GGTAATAACA ACATATTGGG GTCTGCATAC   5280
AGGAGAAAGA GACTGGCATT TAGGTCAGGG AGTCTCCATA GAATGGAGGA AAAGAGATA   5340
TAGCACACAA GTAGACCCTG ACCTAGCAGA CCACCTAATT CATCTGCATT ACTTTGATTG   5400
TTTTTCAGAC TCTGCCATAA GAAAGGCCAT ATTAGGACAT AGAGTTAGTC CTATTTGTGA   5460
ATTTCAAGCA GGACATAACA AGGTAGGATC TCTACAGTAC TTGGCACTAA CAGCATTAAT   5520
AACACCAAAA AAGATAAAGC CACCTTTGCC TAGTGTTAAG AAACTGACAG AGGATAGATG   5580
GAACAAGCCC CAGAAGACCA AGGGCCACAG AGGGAGCCAT ACAATCAATG GCATTAGAG   5640
CTTTTAGAGG AGCTTAAGAA TGAAGCTGTT AGACATTTTC CTAGGATATG GCTCCATGGC   5700
TTAGGGCAAC ATATCTATGA AACTTATGGG GATACTTGGG CAGGAGTGGA AGCCATAATA   5760
AGAATTCTAC AACAACTGCT GTTTATTCAT TTCAGAATTG GGTGTCGACA TAGCAGAATA   5820
GGCATTATTC GACAGAGGAG AGCAAGAAAT GGAGCCAGTA GATCCTAGAC TAGAGCCCTG   5880
GAAGCATCCA GGAAGTCAGC CTAAGACTGC TTGTACCACT TGCTATTGTA AAAAGTGTTG   5940
CTTTCATTGC CAAGTTTGTT TCACAAAAAA AGCCTTAGGC ATCTCCTATG GCAGGAAGAA   6000
GCGGAGACAG CGACGAAGAG CTCCTGAAGA CAGTCAGACT CATCAAGTTT CTCTACCAAA   6060
GCAGTAAGTA GTACATGTAA TGCAACCTTT AGTAATAGCA GCAATAGTAG CATTAGTAGT   6120
AGCAGGAATA ATAGCAATAG TTGTGTGATC CATAGTATTC ATAGAATATA GGAAAATAAG   6180
AAGACAAAGA AAAATAGACA GGGTAATTGA CAGAATAAGC GAAAGAGCAG AAGACAGTGG   6240
CA ATG AGA GTG AAG GGG ATC AGG AGG AAT TAT CAG CAC TGG TGG GGA       6287
   Met Arg Val Lys Gly Ile Arg Arg Asn Tyr Gln His Trp Trp Gly
   1           5                   10                  15

TGG GGC ACG ATG CTC CTT GGG TTA TTA ATG ATC TGT AGT GCT ACA GAA      6335
Trp Gly Thr Met Leu Leu Gly Leu Leu Met Ile Cys Ser Ala Thr Glu
            20                  25                  30

AAA TTG TGG GTC ACA GTC TAT TAT GGG GTA CCT GTG TGG AAA GAA GCA      6383
Lys Leu Trp Val Thr Val Tyr Tyr Gly Val Pro Val Trp Lys Glu Ala
        35                  40                  45

ACC ACC ACT CTA TTT TGT GCA TCA GAT GCT AAA GCA TAT GAT ACA GAG      6431
Thr Thr Thr Leu Phe Cys Ala Ser Asp Ala Lys Ala Tyr Asp Thr Glu
    50                  55                  60

GTA CAT AAT GTT TGG GCC ACA CAT GCC TGT GTA CCC ACA GAC CCC AAC      6479
Val His Asn Val Trp Ala Thr His Ala Cys Val Pro Thr Asp Pro Asn
65                  70                  75

CCA CAA GAA GTA GAA TTG GTA AAT GTG ACA GAA AAT TTT AAC ATG TGG      6527
Pro Gln Glu Val Glu Leu Val Asn Val Thr Glu Asn Phe Asn Met Trp
80                  85                  90                  95
```

| | | | | | | | | | | | | | | | | |
|---|---|---|---|---|---|---|---|---|---|---|---|---|---|---|---|---|
| AAA | AAT | AAC | ATG | GTA | GAA | CAG | ATG | CAT | GAG | GAT | ATA | ATC | AGT | TTA | TGG | 6575 |
| Lys | Asn | Asn | Met | Val | Glu | Gln | Met | His | Glu | Asp | Ile | Ile | Ser | Leu | Trp | |
| | | | 100 | | | | | 105 | | | | | | 110 | | |
| GAT | CAA | AGC | CTA | AAG | CCA | TGT | GTA | AAA | TTA | ACC | CCA | CTC | TGT | GTT | ACT | 6623 |
| Asp | Gln | Ser | Leu | Lys | Pro | Cys | Val | Lys | Leu | Thr | Pro | Leu | Cys | Val | Thr | |
| | | | 115 | | | | 120 | | | | | | 125 | | | |
| TTA | AAT | TGC | ACT | GAT | TTG | AGG | AAT | ACT | ACT | AAT | ACC | AAT | AAT | AGT | ACT | 6671 |
| Leu | Asn | Cys | Thr | Asp | Leu | Arg | Asn | Thr | Thr | Asn | Thr | Asn | Asn | Ser | Thr | |
| | | 130 | | | | | 135 | | | | | 140 | | | | |
| GCT | AAT | AAC | AAT | AGT | AAT | AGC | GAG | GGA | ACA | ATA | AAG | GGA | GGA | GAA | ATG | 6719 |
| Ala | Asn | Asn | Asn | Ser | Asn | Ser | Glu | Gly | Thr | Ile | Lys | Gly | Gly | Glu | Met | |
| | 145 | | | | | 150 | | | | | 155 | | | | | |
| AAA | AAC | TGC | TCT | TTC | AAT | ATC | ACC | ACA | AGC | ATA | AGA | GAT | AAG | ATG | CAG | 6767 |
| Lys | Asn | Cys | Ser | Phe | Asn | Ile | Thr | Thr | Ser | Ile | Arg | Asp | Lys | Met | Gln | |
| 160 | | | | | 165 | | | | | 170 | | | | | 175 | |
| AAA | GAA | TAT | GCA | CTT | CTT | TAT | AAA | CTT | GAT | ATA | GTA | TCA | ATA | AAT | AAT | 6815 |
| Lys | Glu | Tyr | Ala | Leu | Leu | Tyr | Lys | Leu | Asp | Ile | Val | Ser | Ile | Asn | Asn | |
| | | | | 180 | | | | | 185 | | | | | 190 | | |
| GAT | AGT | ACC | AGC | TAT | AGG | TTG | ATA | AGT | TGT | AAT | ACC | TCA | GTC | ATT | ACA | 6863 |
| Asp | Ser | Thr | Ser | Tyr | Arg | Leu | Ile | Ser | Cys | Asn | Thr | Ser | Val | Ile | Thr | |
| | | | 195 | | | | 200 | | | | | | 205 | | | |
| CAA | GCT | TGT | CCA | AAG | ATA | TCC | TTT | GAG | CCA | ATT | CCC | ATA | CAC | TAT | TGT | 6911 |
| Gln | Ala | Cys | Pro | Lys | Ile | Ser | Phe | Glu | Pro | Ile | Pro | Ile | His | Tyr | Cys | |
| | | 210 | | | | | 215 | | | | | 220 | | | | |
| GCC | CCG | GCT | GGT | TTT | GCG | ATT | CTA | AAG | TGT | AAC | GAT | AAA | AAG | TTC | AGT | 6959 |
| Ala | Pro | Ala | Gly | Phe | Ala | Ile | Leu | Lys | Cys | Asn | Asp | Lys | Lys | Phe | Ser | |
| | 225 | | | | | 230 | | | | | 235 | | | | | |
| GGA | AAA | GGA | TCA | TGT | AAA | AAT | GTC | AGC | ACA | GTA | CAA | TGT | ACA | CAT | GGA | 7007 |
| Gly | Lys | Gly | Ser | Cys | Lys | Asn | Val | Ser | Thr | Val | Gln | Cys | Thr | His | Gly | |
| 240 | | | | | 245 | | | | | 250 | | | | | 255 | |
| ATT | AGG | CCA | GTA | GTA | TCA | ACT | CAA | CTG | CTG | TTA | AAT | GGC | AGT | CTA | GCA | 7055 |
| Ile | Arg | Pro | Val | Val | Ser | Thr | Gln | Leu | Leu | Leu | Asn | Gly | Ser | Leu | Ala | |
| | | | | 260 | | | | | 265 | | | | | 270 | | |
| GAA | GAA | GAG | GTA | GTA | ATT | AGA | TCT | GAG | AAT | TTC | AAT | GAT | AAT | GCT | AAA | 7103 |
| Glu | Glu | Glu | Val | Val | Ile | Arg | Ser | Glu | Asn | Phe | Asn | Asp | Asn | Ala | Lys | |
| | | | 275 | | | | | 280 | | | | | 285 | | | |
| ACC | ATC | ATA | GTA | CAT | CTG | AAT | GAA | TCT | GTA | CAA | ATT | AAT | TGT | ACA | AGA | 7151 |
| Thr | Ile | Ile | Val | His | Leu | Asn | Glu | Ser | Val | Gln | Ile | Asn | Cys | Thr | Arg | |
| | | 290 | | | | | 295 | | | | | 300 | | | | |
| CCC | AAC | TAC | AAT | AAA | AGA | AAA | AGG | ATA | CAT | ATA | GGA | CCA | GGG | AGA | GCA | 7199 |
| Pro | Asn | Tyr | Asn | Lys | Arg | Lys | Arg | Ile | His | Ile | Gly | Pro | Gly | Arg | Ala | |
| | 305 | | | | | 310 | | | | | 315 | | | | | |
| TTT | TAT | ACA | ACA | AAA | AAT | ATA | ATA | GGA | ACT | ATA | AGA | CAA | GCA | CAT | TGT | 7247 |
| Phe | Tyr | Thr | Thr | Lys | Asn | Ile | Ile | Gly | Thr | Ile | Arg | Gln | Ala | His | Cys | |
| 320 | | | | | 325 | | | | | 330 | | | | | 335 | |
| AAC | ATT | AGT | AGA | GCA | AAA | TGG | AAT | GAC | ACT | TTA | AGA | CAG | ATA | GTT | AGC | 7295 |
| Asn | Ile | Ser | Arg | Ala | Lys | Trp | Asn | Asp | Thr | Leu | Arg | Gln | Ile | Val | Ser | |
| | | | | 340 | | | | | 345 | | | | | 350 | | |
| AAA | TTA | AAA | GAA | CAA | TTT | AAG | AAT | AAA | ACA | ATA | GTC | TTT | AAT | CAA | TCC | 7343 |
| Lys | Leu | Lys | Glu | Gln | Phe | Lys | Asn | Lys | Thr | Ile | Val | Phe | Asn | Gln | Ser | |
| | | | | 355 | | | | 360 | | | | | 365 | | | |
| TCA | GGA | GGG | GAC | CCA | GAA | ATT | GTA | ATG | CAC | AGT | TTT | AAT | TGT | GGA | GGG | 7391 |
| Ser | Gly | Gly | Asp | Pro | Glu | Ile | Val | Met | His | Ser | Phe | Asn | Cys | Gly | Gly | |
| | | | 370 | | | | | 375 | | | | | 380 | | | |
| GAA | TTT | TTC | TAC | TGT | AAT | ACA | TCA | CCA | CTG | TTT | AAT | AGT | ACT | TGG | AAT | 7439 |
| Glu | Phe | Phe | Tyr | Cys | Asn | Thr | Ser | Pro | Leu | Phe | Asn | Ser | Thr | Trp | Asn | |
| | 385 | | | | | 390 | | | | | 395 | | | | | |
| GGT | AAT | AAT | ACT | TGG | AAT | AAT | ACT | ACA | GGG | TCA | AAT | AAC | AAT | ATC | ACA | 7487 |
| Gly | Asn | Asn | Thr | Trp | Asn | Asn | Thr | Thr | Gly | Ser | Asn | Asn | Asn | Ile | Thr | |
| 400 | | | | | 405 | | | | | 410 | | | | | 415 | |
| CTT | CAA | TGC | AAA | ATA | AAA | CAA | ATT | ATA | AAC | ATG | TGG | CAG | GAA | GTA | GGA | 7535 |
| Leu | Gln | Cys | Lys | Ile | Lys | Gln | Ile | Ile | Asn | Met | Trp | Gln | Glu | Val | Gly | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 420 |     |     |     |     | 425 |     |     |     |     | 430 |     |     |      |
| AAA | GCA | ATA | TAT | GCC | CCT | CCC | ATT | GAA | GGA | CAA | ATT | AGA | TGT | TCA | TCA | 7583 |
| Lys | Ala | Ile | Tyr | Ala | Pro | Pro | Ile | Glu | Gly | Gln | Ile | Arg | Cys | Ser | Ser |      |
|     |     |     | 435 |     |     |     |     | 440 |     |     |     |     | 445 |     |     |      |
| AAT | ATT | ACA | GGG | CTA | CTA | TTA | ACA | AGA | GAT | GGT | GGT | AAG | GAC | ACG | GAC | 7631 |
| Asn | Ile | Thr | Gly | Leu | Leu | Leu | Thr | Arg | Asp | Gly | Gly | Lys | Asp | Thr | Asp |      |
|     |     |     | 450 |     |     |     |     | 455 |     |     |     |     | 460 |     |     |      |
| ACG | AAC | GAC | ACC | GAG | ATC | TTC | AGA | CCT | GGA | GGA | GGA | GAT | ATG | AGG | GAC | 7679 |
| Thr | Asn | Asp | Thr | Glu | Ile | Phe | Arg | Pro | Gly | Gly | Gly | Asp | Met | Arg | Asp |      |
|     |     | 465 |     |     |     |     | 470 |     |     |     |     | 475 |     |     |     |      |
| AAT | TGG | AGA | AGT | GAA | TTA | TAT | AAA | TAT | AAA | GTA | GTA | ACA | ATT | GAA | CCA | 7727 |
| Asn | Trp | Arg | Ser | Glu | Leu | Tyr | Lys | Tyr | Lys | Val | Val | Thr | Ile | Glu | Pro |      |
| 480 |     |     |     |     | 485 |     |     |     |     | 490 |     |     |     |     | 495 |      |
| TTA | GGA | GTA | GCA | CCC | ACC | AAG | GCA | AAG | AGA | AGA | GTG | GTG | CAG | AGA | GAA | 7775 |
| Leu | Gly | Val | Ala | Pro | Thr | Lys | Ala | Lys | Arg | Arg | Val | Val | Gln | Arg | Glu |      |
|     |     |     |     | 500 |     |     |     |     | 505 |     |     |     |     | 510 |     |      |
| AAA | AGA | GCA | GCG | ATA | GGA | GCT | CTG | TTC | CTT | GGG | TTC | TTA | GGA | GCA | GCA | 7823 |
| Lys | Arg | Ala | Ala | Ile | Gly | Ala | Leu | Phe | Leu | Gly | Phe | Leu | Gly | Ala | Ala |      |
|     |     |     |     | 515 |     |     |     |     | 520 |     |     |     |     | 525 |     |      |
| GGA | AGC | ACT | ATG | GGC | GCA | GCG | TCA | GTG | ACG | CTG | ACG | GTA | CAG | GCC | AGA | 7871 |
| Gly | Ser | Thr | Met | Gly | Ala | Ala | Ser | Val | Thr | Leu | Thr | Val | Gln | Ala | Arg |      |
|     |     | 530 |     |     |     |     | 535 |     |     |     |     | 540 |     |     |     |      |
| CTA | TTA | TTG | TCT | GGT | ATA | GTG | CAA | CAG | CAG | AAC | AAT | TTG | CTG | AGG | GCC | 7919 |
| Leu | Leu | Leu | Ser | Gly | Ile | Val | Gln | Gln | Gln | Asn | Asn | Leu | Leu | Arg | Ala |      |
|     | 545 |     |     |     |     | 550 |     |     |     |     | 555 |     |     |     |     |      |
| ATT | GAG | GCG | CAA | CAG | CAT | ATG | TTG | CAA | CTC | ACA | GTC | TGG | GGC | ATC | AAG | 7967 |
| Ile | Glu | Ala | Gln | Gln | His | Met | Leu | Gln | Leu | Thr | Val | Trp | Gly | Ile | Lys |      |
| 560 |     |     |     |     | 565 |     |     |     |     | 570 |     |     |     |     | 575 |      |
| CAG | CTC | CAG | GCA | AGA | ATC | CTG | GCT | GTG | GAA | AGA | TAC | CTA | AAG | GAT | CAA | 8015 |
| Gln | Leu | Gln | Ala | Arg | Ile | Leu | Ala | Val | Glu | Arg | Tyr | Leu | Lys | Asp | Gln |      |
|     |     |     |     | 580 |     |     |     |     | 585 |     |     |     |     | 590 |     |      |
| CAG | CTC | CTG | GGG | ATT | TGG | GGT | TGC | TCT | GGA | AAA | CTC | ATT | TGC | ACC | ACT | 8063 |
| Gln | Leu | Leu | Gly | Ile | Trp | Gly | Cys | Ser | Gly | Lys | Leu | Ile | Cys | Thr | Thr |      |
|     |     |     | 595 |     |     |     |     | 600 |     |     |     |     | 605 |     |     |      |
| ACT | GTG | CCT | TGG | AAT | GCT | AGT | TGG | AGT | AAT | AAA | TCT | CTG | GAT | GAT | ATT | 8111 |
| Thr | Val | Pro | Trp | Asn | Ala | Ser | Trp | Ser | Asn | Lys | Ser | Leu | Asp | Asp | Ile |      |
|     |     | 610 |     |     |     |     | 615 |     |     |     |     | 620 |     |     |     |      |
| TGG | AAT | AAC | ATG | ACC | TGG | ATG | CAG | TGG | GAA | AGA | GAA | ATT | GAC | AAT | TAC | 8159 |
| Trp | Asn | Asn | Met | Thr | Trp | Met | Gln | Trp | Glu | Arg | Glu | Ile | Asp | Asn | Tyr |      |
| 625 |     |     |     |     | 630 |     |     |     |     | 635 |     |     |     |     |     |      |
| ACA | AGC | TTA | ATA | TAC | TCA | TTA | CTA | GAA | AAA | TCG | CAA | ACC | CAA | CAA | GAA | 8207 |
| Thr | Ser | Leu | Ile | Tyr | Ser | Leu | Leu | Glu | Lys | Ser | Gln | Thr | Gln | Gln | Glu |      |
| 640 |     |     |     |     | 645 |     |     |     |     | 650 |     |     |     |     | 655 |      |
| ATG | AAT | GAA | CAA | GAA | TTA | TTG | GAA | TTG | GAT | AAA | TGG | GCA | AGT | TTG | TGG | 8255 |
| Met | Asn | Glu | Gln | Glu | Leu | Leu | Glu | Leu | Asp | Lys | Trp | Ala | Ser | Leu | Trp |      |
|     |     |     |     | 660 |     |     |     |     | 665 |     |     |     |     | 670 |     |      |
| AAT | TGG | TTT | GAC | ATA | ACA | AAT | TGG | CTG | TGG | TAT | ATA | AAA | ATA | TTC | ATA | 8303 |
| Asn | Trp | Phe | Asp | Ile | Thr | Asn | Trp | Leu | Trp | Tyr | Ile | Lys | Ile | Phe | Ile |      |
|     |     |     | 675 |     |     |     |     | 680 |     |     |     |     | 685 |     |     |      |
| ATG | ATA | GTA | GGA | GGC | TTG | GTA | GGT | TTA | AGA | ATA | GTT | TTT | GCT | GTA | CTT | 8351 |
| Met | Ile | Val | Gly | Gly | Leu | Val | Gly | Leu | Arg | Ile | Val | Phe | Ala | Val | Leu |      |
|     |     |     | 690 |     |     |     |     | 695 |     |     |     |     | 700 |     |     |      |
| TCT | ATA | GTG | AAT | AGA | GTT | AGG | CAG | GGA | TAC | TCA | CCA | TTG | TCG | TTG | CAG | 8399 |
| Ser | Ile | Val | Asn | Arg | Val | Arg | Gln | Gly | Tyr | Ser | Pro | Leu | Ser | Leu | Gln |      |
|     |     | 705 |     |     |     |     | 710 |     |     |     |     | 715 |     |     |     |      |
| ACC | CGC | CCC | CCA | GTT | CCG | AGG | GGA | CCC | GAC | AGG | CCC | GAA | GGA | ATC | GAA | 8447 |
| Thr | Arg | Pro | Pro | Val | Pro | Arg | Gly | Pro | Asp | Arg | Pro | Glu | Gly | Ile | Glu |      |
| 720 |     |     |     |     | 725 |     |     |     |     | 730 |     |     |     |     | 735 |      |
| GAA | GAA | GGT | GGA | GAG | AGA | GAC | AGA | GAC | ACA | TCC | GGT | CGA | TTA | GTG | CAT | 8495 |
| Glu | Glu | Gly | Gly | Glu | Arg | Asp | Arg | Asp | Thr | Ser | Gly | Arg | Leu | Val | His |      |
|     |     |     |     | 740 |     |     |     |     | 745 |     |     |     |     | 750 |     |      |

| | | | | | | | | | | | | | | | | |
|---|---|---|---|---|---|---|---|---|---|---|---|---|---|---|---|---|
| GGA | TTC | TTA | GCA | ATT | ATC | TGG | GTC | GAC | CTG | CGG | AGC | CTG | TTC | CTC | TTC | 8543 |
| Gly | Phe | Leu | Ala | Ile | Ile | Trp | Val | Asp | Leu | Arg | Ser | Leu | Phe | Leu | Phe | |
| | | 755 | | | | | 760 | | | | | 765 | | | | |
| AGC | TAC | CAC | CAC | TTG | AGA | GAC | TTA | CTC | TTG | ATT | GCA | GCG | AGG | ATT | GTG | 8591 |
| Ser | Tyr | His | His | Leu | Arg | Asp | Leu | Leu | Leu | Ile | Ala | Ala | Arg | Ile | Val | |
| | | 770 | | | | | 775 | | | | | 780 | | | | |
| GAA | CTT | CTG | GGA | CGC | AGG | GGG | TGG | GAA | GTC | CTC | AAA | TAT | TGG | TGG | AAT | 8639 |
| Glu | Leu | Leu | Gly | Arg | Arg | Gly | Trp | Glu | Val | Leu | Lys | Tyr | Trp | Trp | Asn | |
| | 785 | | | | | 790 | | | | | 795 | | | | | |
| CTC | CTA | CAG | TAT | TGG | AGT | CAG | GAA | CTA | AAG | AGT | AGT | GCT | GTT | AGC | TTG | 8687 |
| Leu | Leu | Gln | Tyr | Trp | Ser | Gln | Glu | Leu | Lys | Ser | Ser | Ala | Val | Ser | Leu | |
| 800 | | | | | 805 | | | | | 810 | | | | | 815 | |
| CTT | AAT | GCC | ACA | GAT | ATA | GCA | GTA | GCT | GAG | GGG | ACA | GAT | AGG | GTT | ATA | 8735 |
| Leu | Asn | Ala | Thr | Asp | Ile | Ala | Val | Ala | Glu | Gly | Thr | Asp | Arg | Val | Ile | |
| | | | 820 | | | | | 825 | | | | | 830 | | | |
| GAA | GTA | CTG | CAA | AGA | GCT | GGT | AGA | GCT | ATT | CTC | CAC | ATA | CCT | ACA | AGA | 8783 |
| Glu | Val | Leu | Gln | Arg | Ala | Gly | Arg | Ala | Ile | Leu | His | Ile | Pro | Thr | Arg | |
| | | | 835 | | | | | 840 | | | | | 845 | | | |
| ATA | AGA | CAG | GGC | TTG | GAA | AGG | GCT | TTG | CTA | TAAGATGGGT | GGCAAATGGT | | | | | 8833 |
| Ile | Arg | Gln | Gly | Leu | Glu | Arg | Ala | Leu | Leu | | | | | | | |
| | | 850 | | | | | 855 | | | | | | | | | |

CAAAACGTGT GACTGGATGG CCTACTGTAA GGGAAAAAAT GAGACGAGCT GAACCAGCTG 8893
AGCCAGCAGC AGATGGGGTG GGAGCAGCAT CCCGAGACCT GGAAAAACAT GGAGCACTCA 8953
CAAGTAGCAA TACAGCAGCT ACCAATGCTG ATTGTGCCTG GCTAGAAGCA CAAGAGGAGG 9013
AGGAAGTGGG TTTTCCAGTC AGACCTCAGG TACCTTTAAG ACCAATGACT TACAAAGCAG 9073
CTTTAGATCT TAGCCACTTT TTAAAAGAAA AGGGGGGACT GGATGGGTTA ATTTACTCCC 9133
AAAAGAGACA AGACATCCTT GATCTGTGGG TCTACCACAC ACAAGGCTAC TTCCCTGATT 9193
GGCAGAACTA CACACCAGGG CCAGGGATCA GATATCCACT GACCTTTGGA TGGTGCTTCA 9253
AGCTAGTACC AGTTGAGCCA GAGAAGATAG AAGAGGCCAA TAAAGGAGAG AACAACTGCT 9313
TGTTACACCC TATGAGCCAG CATGGGATGG ATGACCCGGA GAGAGAAGTG TTAGTGTGGA 9373
AGTCTGACAG CCACCTAGCA TTTCAGCATT ATGCCCGAGA GCTGCATCCG GAGTACTACA 9433
AGAACTGCTG ACATCGAGCT ATCTACAAGG GACTTTCCGC TGGGGACTTT CCAGGGAGGT 9493
GTGGCCTGGG CGGGACCGGG GAGTGGCGAG CCCTCAGATG CTGCATATAA GCAGCTGCTT 9553
TCTGCCTGTA CTGGGTCTCT CTGGTTAGAC CAGATCTGAG CCTGGGAGCT CTCTGGCTAA 9613
CTAGGGAACC CACTGCTTAA GCCTCAATAA AGCTTGCCTT GAGTGCTTCA AGTAGTGTGT 9673
GCCCGTCTGT TATGTGACTC TGGTAGCTAG AGATCCCTCA GATCCTTTTA GGCAGTGTGG 9733
AAAATCTCTA GCA 9746

( 2 ) INFORMATION FOR SEQ ID NO:4:

( i ) SEQUENCE CHARACTERISTICS:
        ( A ) LENGTH: 857 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Arg | Val | Lys | Gly | Ile | Arg | Arg | Asn | Tyr | Gln | His | Trp | Trp | Gly | Trp |
| 1 | | | | 5 | | | | | 10 | | | | | 15 | |
| Gly | Thr | Met | Leu | Leu | Gly | Leu | Leu | Met | Ile | Cys | Ser | Ala | Thr | Glu | Lys |
| | | | 20 | | | | | 25 | | | | | 30 | | |
| Leu | Trp | Val | Thr | Val | Tyr | Tyr | Gly | Val | Pro | Val | Trp | Lys | Glu | Ala | Thr |
| | | 35 | | | | | 40 | | | | | 45 | | | |
| Thr | Thr | Leu | Phe | Cys | Ala | Ser | Asp | Ala | Lys | Ala | Tyr | Asp | Thr | Glu | Val |

|  |  |  |  |  |  |  |  |  |  |  |  |  |  |  |
|---|---|---|---|---|---|---|---|---|---|---|---|---|---|---|
|  |  | 50 |  |  |  | 55 |  |  |  | 60 |  |  |  |  |
| His | Asn | Val | Trp | Ala | Thr | His | Ala | Cys | Val | Pro | Thr | Asp | Pro | Asn | Pro |
| 65 |  |  |  | 70 |  |  |  | 75 |  |  |  |  |  | 80 |
| Gln | Glu | Val | Glu | Leu | Val | Asn | Val | Thr | Glu | Asn | Phe | Asn | Met | Trp | Lys |
|  |  |  |  | 85 |  |  |  | 90 |  |  |  |  |  | 95 |
| Asn | Asn | Met | Val | Glu | Gln | Met | His | Glu | Asp | Ile | Ile | Ser | Leu | Trp | Asp |
|  |  |  | 100 |  |  |  | 105 |  |  |  |  | 110 |  |  |
| Gln | Ser | Leu | Lys | Pro | Cys | Val | Lys | Leu | Thr | Pro | Leu | Cys | Val | Thr | Leu |
|  |  | 115 |  |  |  |  | 120 |  |  |  |  | 125 |  |  |
| Asn | Cys | Thr | Asp | Leu | Arg | Asn | Thr | Thr | Thr | Asn | Asn | Ser | Thr | Ala |
| 130 |  |  |  |  | 135 |  |  |  |  | 140 |  |  |  |  |
| Asn | Asn | Asn | Ser | Asn | Ser | Glu | Gly | Thr | Ile | Lys | Gly | Gly | Glu | Met | Lys |
| 145 |  |  |  |  | 150 |  |  |  |  | 155 |  |  |  |  | 160 |
| Asn | Cys | Ser | Phe | Asn | Ile | Thr | Thr | Ser | Ile | Arg | Asp | Lys | Met | Gln | Lys |
|  |  |  |  | 165 |  |  |  |  | 170 |  |  |  |  | 175 |
| Glu | Tyr | Ala | Leu | Leu | Tyr | Lys | Leu | Asp | Ile | Val | Ser | Ile | Asn | Asn | Asp |
|  |  |  | 180 |  |  |  |  | 185 |  |  |  |  | 190 |  |
| Ser | Thr | Ser | Tyr | Arg | Leu | Ile | Ser | Cys | Asn | Thr | Ser | Val | Ile | Thr | Gln |
|  |  | 195 |  |  |  |  | 200 |  |  |  |  | 205 |  |  |
| Ala | Cys | Pro | Lys | Ile | Ser | Phe | Glu | Pro | Ile | Pro | Ile | His | Tyr | Cys | Ala |
| 210 |  |  |  |  | 215 |  |  |  |  |  | 220 |  |  |  |  |
| Pro | Ala | Gly | Phe | Ala | Ile | Leu | Lys | Cys | Asn | Asp | Lys | Lys | Phe | Ser | Gly |
| 225 |  |  |  |  | 230 |  |  |  |  | 235 |  |  |  |  | 240 |
| Lys | Gly | Ser | Cys | Lys | Asn | Val | Ser | Thr | Val | Gln | Cys | Thr | His | Gly | Ile |
|  |  |  |  | 245 |  |  |  |  | 250 |  |  |  |  | 255 |  |
| Arg | Pro | Val | Val | Ser | Thr | Gln | Leu | Leu | Leu | Asn | Gly | Ser | Leu | Ala | Glu |
|  |  |  | 260 |  |  |  |  | 265 |  |  |  |  | 270 |  |  |
| Glu | Glu | Val | Val | Ile | Arg | Ser | Glu | Asn | Phe | Asn | Asp | Asn | Ala | Lys | Thr |
|  |  | 275 |  |  |  |  | 280 |  |  |  |  | 285 |  |  |  |
| Ile | Ile | Val | His | Leu | Asn | Glu | Ser | Val | Gln | Ile | Asn | Cys | Thr | Arg | Pro |
|  | 290 |  |  |  |  | 295 |  |  |  |  | 300 |  |  |  |  |
| Asn | Tyr | Asn | Lys | Arg | Lys | Arg | Ile | His | Ile | Gly | Pro | Gly | Arg | Ala | Phe |
| 305 |  |  |  |  | 310 |  |  |  |  | 315 |  |  |  |  | 320 |
| Tyr | Thr | Thr | Lys | Asn | Ile | Ile | Gly | Thr | Ile | Arg | Gln | Ala | His | Cys | Asn |
|  |  |  |  | 325 |  |  |  |  | 330 |  |  |  |  | 335 |  |
| Ile | Ser | Arg | Ala | Lys | Trp | Asn | Asp | Thr | Leu | Arg | Gln | Ile | Val | Ser | Lys |
|  |  |  | 340 |  |  |  |  | 345 |  |  |  |  | 350 |  |  |
| Leu | Lys | Glu | Gln | Phe | Lys | Asn | Lys | Thr | Ile | Val | Phe | Asn | Gln | Ser | Ser |
|  |  | 355 |  |  |  |  | 360 |  |  |  |  | 365 |  |  |  |
| Gly | Gly | Asp | Pro | Glu | Ile | Val | Met | His | Ser | Phe | Asn | Cys | Gly | Gly | Glu |
|  | 370 |  |  |  |  | 375 |  |  |  |  | 380 |  |  |  |  |
| Phe | Phe | Tyr | Cys | Asn | Thr | Ser | Pro | Leu | Phe | Asn | Ser | Thr | Trp | Asn | Gly |
| 385 |  |  |  |  | 390 |  |  |  |  | 395 |  |  |  |  | 400 |
| Asn | Asn | Thr | Trp | Asn | Asn | Thr | Thr | Gly | Ser | Asn | Asn | Ile | Thr | Leu |
|  |  |  |  | 405 |  |  |  |  | 410 |  |  |  |  | 415 |  |
| Gln | Cys | Lys | Ile | Lys | Gln | Ile | Ile | Asn | Met | Trp | Gln | Glu | Val | Gly | Lys |
|  |  |  | 420 |  |  |  |  | 425 |  |  |  |  | 430 |  |  |
| Ala | Ile | Tyr | Ala | Pro | Pro | Ile | Glu | Gly | Gln | Ile | Arg | Cys | Ser | Ser | Asn |
|  |  | 435 |  |  |  |  | 440 |  |  |  |  | 445 |  |  |  |
| Ile | Thr | Gly | Leu | Leu | Leu | Thr | Arg | Asp | Gly | Gly | Lys | Asp | Thr | Asp | Thr |
|  |  | 450 |  |  |  |  | 455 |  |  |  |  | 460 |  |  |  |
| Asn | Asp | Thr | Glu | Ile | Phe | Arg | Pro | Gly | Gly | Gly | Asp | Met | Arg | Asp | Asn |
| 465 |  |  |  |  | 470 |  |  |  |  | 475 |  |  |  |  | 480 |
| Trp | Arg | Ser | Glu | Leu | Tyr | Lys | Tyr | Lys | Val | Val | Thr | Ile | Glu | Pro | Leu |
|  |  |  |  | 485 |  |  |  |  | 490 |  |  |  |  | 495 |  |

```
Gly Val Ala Pro Thr Lys Ala Lys Arg Arg Val Val Gln Arg Glu Lys
            500                 505                 510
Arg Ala Ala Ile Gly Ala Leu Phe Leu Gly Phe Leu Gly Ala Ala Gly
        515                 520                 525
Ser Thr Met Gly Ala Ala Ser Val Thr Leu Thr Val Gln Ala Arg Leu
    530                 535                 540
Leu Leu Ser Gly Ile Val Gln Gln Asn Asn Leu Leu Arg Ala Ile
545                 550                 555                 560
Glu Ala Gln Gln His Met Leu Gln Leu Thr Val Trp Gly Ile Lys Gln
                565                 570                 575
Leu Gln Ala Arg Ile Leu Ala Val Glu Arg Tyr Leu Lys Asp Gln Gln
            580                 585                 590
Leu Leu Gly Ile Trp Gly Cys Ser Gly Lys Leu Ile Cys Thr Thr Thr
        595                 600                 605
Val Pro Trp Asn Ala Ser Trp Ser Asn Lys Ser Leu Asp Asp Ile Trp
    610                 615                 620
Asn Asn Met Thr Trp Met Gln Trp Glu Arg Glu Ile Asp Asn Tyr Thr
625                 630                 635                 640
Ser Leu Ile Tyr Ser Leu Leu Glu Lys Ser Gln Thr Gln Gln Glu Met
                645                 650                 655
Asn Glu Gln Glu Leu Leu Glu Leu Asp Lys Trp Ala Ser Leu Trp Asn
            660                 665                 670
Trp Phe Asp Ile Thr Asn Trp Leu Trp Tyr Ile Lys Ile Phe Ile Met
        675                 680                 685
Ile Val Gly Gly Leu Val Gly Leu Arg Ile Val Phe Ala Val Leu Ser
    690                 695                 700
Ile Val Asn Arg Val Arg Gln Gly Tyr Ser Pro Leu Ser Leu Gln Thr
705                 710                 715                 720
Arg Pro Pro Val Pro Arg Gly Pro Asp Arg Pro Glu Gly Ile Glu Glu
                725                 730                 735
Glu Gly Gly Glu Arg Asp Arg Asp Thr Ser Gly Arg Leu Val His Gly
            740                 745                 750
Phe Leu Ala Ile Ile Trp Val Asp Leu Arg Ser Leu Phe Leu Phe Ser
        755                 760                 765
Tyr His His Leu Arg Asp Leu Leu Leu Ile Ala Ala Arg Ile Val Glu
    770                 775                 780
Leu Leu Gly Arg Arg Gly Trp Glu Val Leu Lys Tyr Trp Trp Asn Leu
785                 790                 795                 800
Leu Gln Tyr Trp Ser Gln Glu Leu Lys Ser Ala Val Ser Leu Leu
                805                 810                 815
Asn Ala Thr Asp Ile Ala Val Ala Glu Gly Thr Asp Arg Val Ile Glu
            820                 825                 830
Val Leu Gln Arg Ala Gly Arg Ala Ile Leu His Ile Pro Thr Arg Ile
        835                 840                 845
Arg Gln Gly Leu Glu Arg Ala Leu Leu
    850                 855
```

( 2 ) INFORMATION FOR SEQ ID NO:5:

( i ) SEQUENCE CHARACTERISTICS:
        ( A ) LENGTH: 3807 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 648..3215

-continued ( x i ) SEQUENCE DESCRIPTION: SEQ ID NO:5:

| | | | | | |
|---|---|---|---|---|---|
| GATCAAGGGC | CACAGAGGGA | GCCACACAAT | GAATGGACAC | TAGAGCTTTT | AGAGGAGCTT 60 |
| AAGAGTGAAG | CTGTTAGACA | CTTTCCTAGG | ATATGGCTTC | ATGGCTTAGG | GCAACATATC 120 |
| TATGAAACTT | ATGGGGATAC | TTGGGCAGGA | GTGGAAGCCA | TAATAAGAAT | TCTGCAACAA 180 |
| CTGCTGTTTA | TCCATTTCAG | GATTGGGTGC | CAACATAGCA | GAATAGGTAT | TATTCAACAG 240 |
| AGGAGAGCAA | GAAATGGAGC | CAGTAGATCC | TAAACTAGAG | CCCTGGAAGC | ATCCAGGAAG 300 |
| TCAGCCTAAG | ACTGCTTGTA | CCACTTGCTA | TTGTAAAAAG | TGTTGCTTTC | ATTGCCAAGT 360 |
| TTGCTTCATA | ACAAAGGCT | TAGGCATCTC | CTATGGCAGG | AAGAAGCGGA | GACAGCGACG 420 |
| AAGAGCTCCT | CAAGACAGTG | AGACTCATCA | AGTTTCTCTA | TCAAAGCAGT | AAGTAGTACA 480 |
| TGTAATGCAA | GCTTTACAAA | TATCAGCTAT | AGTAGGATTA | GTAGTAGCAG | CAATAATAGC 540 |
| AATAGTTGTG | TGGACCATAG | TATTCATAGA | ATATAGGAAA | ATATTAAGGC | AAAGAAAAAT 600 |
| AGACAGGTTA | ATTGATAGAA | TAACAGAAAG | AGCAGAAGAC | AGTGGCA ATG | AGA GTG 656 |

Met Arg Val
1

| | | | | | | | | | | | | | | | | |
|---|---|---|---|---|---|---|---|---|---|---|---|---|---|---|---|---|
| ACG | GAG | ATC | AGG | AAG | AGT | TAT | CAG | CAC | TGG | TGG | AGA | TGG | GGC | ATC | ATG | 704 |
| Thr | Glu | Ile | Arg | Lys | Ser | Tyr | Gln | His | Trp | Trp | Arg | Trp | Gly | Ile | Met | |
| | 5 | | | | 10 | | | | | 15 | | | | | | |
| CTC | CTT | GGG | ATA | TTA | ATG | ATC | TGT | AAT | GCT | GAA | GAA | AAA | TTG | TGG | GTC | 752 |
| Leu | Leu | Gly | Ile | Leu | Met | Ile | Cys | Asn | Ala | Glu | Glu | Lys | Leu | Trp | Val | |
| 20 | | | | | 25 | | | | | 30 | | | | | 35 | |
| ACA | GTC | TAT | TAT | GGG | GTA | CCT | GTG | TGG | AAA | GAA | GCA | ACC | ACC | ACT | CTA | 800 |
| Thr | Val | Tyr | Tyr | Gly | Val | Pro | Val | Trp | Lys | Glu | Ala | Thr | Thr | Thr | Leu | |
| | | | 40 | | | | | 45 | | | | | 50 | | | |
| TTT | TGT | GCA | TCA | GAT | CGT | AAA | GCA | TAT | GAT | ACA | GAG | GTA | CAT | AAT | GTT | 848 |
| Phe | Cys | Ala | Ser | Asp | Arg | Lys | Ala | Tyr | Asp | Thr | Glu | Val | His | Asn | Val | |
| | | | 55 | | | | | 60 | | | | | 65 | | | |
| TGG | GCC | ACA | CAT | GCC | TGT | GTA | CCC | ACA | GAC | CCC | AAC | CCA | CAA | GAA | GTA | 896 |
| Trp | Ala | Thr | His | Ala | Cys | Val | Pro | Thr | Asp | Pro | Asn | Pro | Gln | Glu | Val | |
| | | 70 | | | | | 75 | | | | | 80 | | | | |
| GAA | TTG | AAA | AAT | GTG | ACA | GAA | AAT | TTT | AAC | ATG | TGG | AAA | AAT | AAC | ATG | 944 |
| Glu | Leu | Lys | Asn | Val | Thr | Glu | Asn | Phe | Asn | Met | Trp | Lys | Asn | Asn | Met | |
| | 85 | | | | | 90 | | | | | 95 | | | | | |
| GTA | GAA | CAA | ATG | CAT | GAG | GAT | ATA | ATC | AGT | TTA | TGG | GAT | CAA | AGC | CTA | 992 |
| Val | Glu | Gln | Met | His | Glu | Asp | Ile | Ile | Ser | Leu | Trp | Asp | Gln | Ser | Leu | |
| 100 | | | | | 105 | | | | | 110 | | | | | 115 | |
| AAG | CCA | TGT | GTA | AAA | TTA | ACC | CCA | CTC | TGT | GTT | ACT | TTA | AAT | TGC | ACT | 1040 |
| Lys | Pro | Cys | Val | Lys | Leu | Thr | Pro | Leu | Cys | Val | Thr | Leu | Asn | Cys | Thr | |
| | | | 120 | | | | | 125 | | | | | 130 | | | |
| GAT | TTG | AGG | AAT | GCT | ACT | AAT | GGG | AAT | GAC | ACT | AAT | ACC | ACT | AGT | AGT | 1088 |
| Asp | Leu | Arg | Asn | Ala | Thr | Asn | Gly | Asn | Asp | Thr | Asn | Thr | Thr | Ser | Ser | |
| | | | 135 | | | | | 140 | | | | | 145 | | | |
| AGC | AGG | GGA | ATG | GTG | GGG | GGA | GGA | GAA | ATG | AAA | AAT | TGC | TCT | TTC | AAT | 1136 |
| Ser | Arg | Gly | Met | Val | Gly | Gly | Gly | Glu | Met | Lys | Asn | Cys | Ser | Phe | Asn | |
| | | | 150 | | | | | 155 | | | | | 160 | | | |
| ATC | ACC | ACA | AAC | ATA | AGA | GGT | AAG | GTG | CAG | AAA | GAA | TAT | GCA | CTT | TTT | 1184 |
| Ile | Thr | Thr | Asn | Ile | Arg | Gly | Lys | Val | Gln | Lys | Glu | Tyr | Ala | Leu | Phe | |
| | 165 | | | | | 170 | | | | | 175 | | | | | |
| TAT | AAA | CTT | GAT | ATA | GCA | CCA | ATA | GAT | AAT | AAT | AGT | AAT | AAT | AGA | TAT | 1232 |
| Tyr | Lys | Leu | Asp | Ile | Ala | Pro | Ile | Asp | Asn | Asn | Ser | Asn | Asn | Arg | Tyr | |
| 180 | | | | | 185 | | | | | 190 | | | | | 195 | |
| AGG | TTG | ATA | AGT | TGT | AAC | ACC | TCA | GTC | ATT | ACA | CAG | GCC | TGT | CCA | AAG | 1280 |
| Arg | Leu | Ile | Ser | Cys | Asn | Thr | Ser | Val | Ile | Thr | Gln | Ala | Cys | Pro | Lys | |
| | | | | 200 | | | | | 205 | | | | | 210 | | |
| GTA | TCC | TTT | GAG | CCA | ATT | CCC | ATA | CAT | TAT | TGT | GCC | CCG | GCT | GGT | TTT | 1328 |
| Val | Ser | Phe | Glu | Pro | Ile | Pro | Ile | His | Tyr | Cys | Ala | Pro | Ala | Gly | Phe | |

-continued

|     |     |     | 215 |     |     |     |     | 220 |     |     |     |     | 225 |     |     |      |
|-----|-----|-----|-----|-----|-----|-----|-----|-----|-----|-----|-----|-----|-----|-----|-----|------|
| GCG | ATT | CTA | AAG | TGT | AAA | GAT | AAG | AAG | TTC | AAT | GGA | AAA | GGA | CCA | TGT | 1376 |
| Ala | Ile | Leu | Lys | Cys | Lys | Asp | Lys | Lys | Phe | Asn | Gly | Lys | Gly | Pro | Cys |      |
|     |     | 230 |     |     |     |     | 235 |     |     |     |     | 240 |     |     |     |      |

| ACA | AAT | GTC | AGC | ACA | GTA | CAA | TGT | ACA | CAT | GGA | ATT | AGG | CCA | GTA | GTA | 1424 |
|-----|-----|-----|-----|-----|-----|-----|-----|-----|-----|-----|-----|-----|-----|-----|-----|------|
| Thr | Asn | Val | Ser | Thr | Val | Gln | Cys | Thr | His | Gly | Ile | Arg | Pro | Val | Val |      |
|     | 245 |     |     |     |     | 250 |     |     |     |     | 255 |     |     |     |     |      |

| TCA | ACT | CAA | CTG | CTG | TTA | AAT | GGC | AGT | CTA | GCA | GAA | GAA | GAG | GTA | GTA | 1472 |
|-----|-----|-----|-----|-----|-----|-----|-----|-----|-----|-----|-----|-----|-----|-----|-----|------|
| Ser | Thr | Gln | Leu | Leu | Leu | Asn | Gly | Ser | Leu | Ala | Glu | Glu | Glu | Val | Val |      |
| 260 |     |     |     |     | 265 |     |     |     |     | 270 |     |     |     |     | 275 |      |

| ATT | AGA | TCC | GCC | AAT | TTC | GCG | GAC | AAT | GCT | AAA | GTC | ATA | ATA | GTA | CAG | 1520 |
|-----|-----|-----|-----|-----|-----|-----|-----|-----|-----|-----|-----|-----|-----|-----|-----|------|
| Ile | Arg | Ser | Ala | Asn | Phe | Ala | Asp | Asn | Ala | Lys | Val | Ile | Ile | Val | Gln |      |
|     |     |     |     | 280 |     |     |     |     | 285 |     |     |     |     | 290 |     |      |

| CTG | AAT | GAA | TCT | GTA | GAA | ATT | AAT | TGT | ACA | AGA | CCC | AAC | AAC | AAT | ACA | 1568 |
|-----|-----|-----|-----|-----|-----|-----|-----|-----|-----|-----|-----|-----|-----|-----|-----|------|
| Leu | Asn | Glu | Ser | Val | Glu | Ile | Asn | Cys | Thr | Arg | Pro | Asn | Asn | Asn | Thr |      |
|     |     |     | 295 |     |     |     |     | 300 |     |     |     |     | 305 |     |     |      |

| AGA | AAA | AGT | ATA | CAT | ATA | GGA | CCA | GGC | AGA | GCA | TTT | TAT | ACA | ACA | GGA | 1616 |
|-----|-----|-----|-----|-----|-----|-----|-----|-----|-----|-----|-----|-----|-----|-----|-----|------|
| Arg | Lys | Ser | Ile | His | Ile | Gly | Pro | Gly | Arg | Ala | Phe | Tyr | Thr | Thr | Gly |      |
|     |     | 310 |     |     |     |     | 315 |     |     |     |     | 320 |     |     |     |      |

| GAA | ATA | ATA | GGA | GAT | ATA | AGA | CAA | GCA | CAT | TGT | AAC | CTT | AGT | AGA | GCA | 1664 |
|-----|-----|-----|-----|-----|-----|-----|-----|-----|-----|-----|-----|-----|-----|-----|-----|------|
| Glu | Ile | Ile | Gly | Asp | Ile | Arg | Gln | Ala | His | Cys | Asn | Leu | Ser | Arg | Ala |      |
|     | 325 |     |     |     |     | 330 |     |     |     |     | 335 |     |     |     |     |      |

| AAA | TGG | AAT | GAC | ACT | TTA | AAT | AAG | ATA | GTT | ATA | AAA | TTA | AGA | GAA | CAA | 1712 |
|-----|-----|-----|-----|-----|-----|-----|-----|-----|-----|-----|-----|-----|-----|-----|-----|------|
| Lys | Trp | Asn | Asp | Thr | Leu | Asn | Lys | Ile | Val | Ile | Lys | Leu | Arg | Glu | Gln |      |
| 340 |     |     |     |     | 345 |     |     |     |     | 350 |     |     |     |     | 355 |      |

| TTT | GGG | AAT | AAA | ACA | ATA | GTC | TTT | AAG | CAC | TCC | TCA | GGA | GGG | GAC | CCA | 1760 |
|-----|-----|-----|-----|-----|-----|-----|-----|-----|-----|-----|-----|-----|-----|-----|-----|------|
| Phe | Gly | Asn | Lys | Thr | Ile | Val | Phe | Lys | His | Ser | Ser | Gly | Gly | Asp | Pro |      |
|     |     |     |     | 360 |     |     |     |     | 365 |     |     |     |     | 370 |     |      |

| GAA | ATT | GTG | ACG | CAC | AGT | TTT | AAT | TGT | GGA | GGG | GAA | TTT | TTC | TAC | TGT | 1808 |
|-----|-----|-----|-----|-----|-----|-----|-----|-----|-----|-----|-----|-----|-----|-----|-----|------|
| Glu | Ile | Val | Thr | His | Ser | Phe | Asn | Cys | Gly | Gly | Glu | Phe | Phe | Tyr | Cys |      |
|     |     |     | 375 |     |     |     |     | 380 |     |     |     |     | 385 |     |     |      |

| AAT | TCA | ACA | CAA | CTG | TTT | AAT | AGT | ACT | TGG | AAT | GTT | ACT | GAA | GAG | TCA | 1856 |
|-----|-----|-----|-----|-----|-----|-----|-----|-----|-----|-----|-----|-----|-----|-----|-----|------|
| Asn | Ser | Thr | Gln | Leu | Phe | Asn | Ser | Thr | Trp | Asn | Val | Thr | Glu | Glu | Ser |      |
|     |     | 390 |     |     |     |     | 395 |     |     |     |     | 400 |     |     |     |      |

| AAT | AAC | ACT | GTA | GAA | AAT | AAC | ACA | ATC | ACA | CTC | CCA | TGC | AGA | ATA | AAA | 1904 |
|-----|-----|-----|-----|-----|-----|-----|-----|-----|-----|-----|-----|-----|-----|-----|-----|------|
| Asn | Asn | Thr | Val | Glu | Asn | Asn | Thr | Ile | Thr | Leu | Pro | Cys | Arg | Ile | Lys |      |
| 405 |     |     |     |     | 410 |     |     |     |     | 415 |     |     |     |     |     |      |

| CAA | ATT | ATA | AAC | ATG | TGG | CAG | GAA | GTA | GGA | AGA | GCA | ATG | TAT | GCC | CCT | 1952 |
|-----|-----|-----|-----|-----|-----|-----|-----|-----|-----|-----|-----|-----|-----|-----|-----|------|
| Gln | Ile | Ile | Asn | Met | Trp | Gln | Glu | Val | Gly | Arg | Ala | Met | Tyr | Ala | Pro |      |
| 420 |     |     |     |     | 425 |     |     |     |     | 430 |     |     |     |     | 435 |      |

| CCC | ATC | AGA | GGA | CAA | ATT | AGA | TGT | TCA | TCA | AAT | ATT | ACA | GGG | CTG | CTA | 2000 |
|-----|-----|-----|-----|-----|-----|-----|-----|-----|-----|-----|-----|-----|-----|-----|-----|------|
| Pro | Ile | Arg | Gly | Gln | Ile | Arg | Cys | Ser | Ser | Asn | Ile | Thr | Gly | Leu | Leu |      |
|     |     |     |     | 440 |     |     |     |     | 445 |     |     |     |     | 450 |     |      |

| TTA | ACA | AGA | GAT | GGT | GGT | CCT | GAG | GAC | AAC | AAG | ACC | GAG | GTC | TTC | AGA | 2048 |
|-----|-----|-----|-----|-----|-----|-----|-----|-----|-----|-----|-----|-----|-----|-----|-----|------|
| Leu | Thr | Arg | Asp | Gly | Gly | Pro | Glu | Asp | Asn | Lys | Thr | Glu | Val | Phe | Arg |      |
|     |     |     | 455 |     |     |     |     | 460 |     |     |     |     | 465 |     |     |      |

| CCT | GGA | GGA | GGA | GAT | ATG | AGG | GAT | AAT | TGG | AGA | AGT | GAA | TTA | TAT | AAA | 2096 |
|-----|-----|-----|-----|-----|-----|-----|-----|-----|-----|-----|-----|-----|-----|-----|-----|------|
| Pro | Gly | Gly | Gly | Asp | Met | Arg | Asp | Asn | Trp | Arg | Ser | Glu | Leu | Tyr | Lys |      |
|     |     | 470 |     |     |     |     | 475 |     |     |     |     | 480 |     |     |     |      |

| TAT | AAA | GTA | GTA | AAA | ATT | GAA | CCA | TTA | GGA | GTA | GCA | CCC | ACC | AAG | GCA | 2144 |
|-----|-----|-----|-----|-----|-----|-----|-----|-----|-----|-----|-----|-----|-----|-----|-----|------|
| Tyr | Lys | Val | Val | Lys | Ile | Glu | Pro | Leu | Gly | Val | Ala | Pro | Thr | Lys | Ala |      |
|     | 485 |     |     |     |     | 490 |     |     |     |     | 495 |     |     |     |     |      |

| AAG | AGA | AGA | GTG | GTG | CAG | AGA | GAA | AAA | AGA | GCA | GTG | GGA | ATA | GGA | GCT | 2192 |
|-----|-----|-----|-----|-----|-----|-----|-----|-----|-----|-----|-----|-----|-----|-----|-----|------|
| Lys | Arg | Arg | Val | Val | Gln | Arg | Glu | Lys | Arg | Ala | Val | Gly | Ile | Gly | Ala |      |
| 500 |     |     |     |     | 505 |     |     |     |     | 510 |     |     |     |     | 515 |      |

| GTG | TTC | CTT | GGG | TTC | TTG | GGA | GCA | GCA | GGA | AGC | ACT | ATG | GGC | GCA | GCG | 2240 |
|-----|-----|-----|-----|-----|-----|-----|-----|-----|-----|-----|-----|-----|-----|-----|-----|------|
| Val | Phe | Leu | Gly | Phe | Leu | Gly | Ala | Ala | Gly | Ser | Thr | Met | Gly | Ala | Ala |      |
|     |     |     |     | 520 |     |     |     |     | 525 |     |     |     |     | 530 |     |      |

| GCA | ATG | ACG | CTG | ACG | GTA | CAG | GCC | AGA | CTA | TTA | TTG | TCT | GGT | ATA | GTG | 2288 |
|-----|-----|-----|-----|-----|-----|-----|-----|-----|-----|-----|-----|-----|-----|-----|-----|------|
| Ala | Met | Thr | Leu | Thr | Val | Gln | Ala | Arg | Leu | Leu | Leu | Ser | Gly | Ile | Val |      |
|     |     |     | 535 |     |     |     |     | 540 |     |     |     |     | 545 |     |     |      |

| | | | | | | | | | | | | | | | |
|---|---|---|---|---|---|---|---|---|---|---|---|---|---|---|---|
| CAA | CAG | CAG | AAC | AAT | CTG | CTG | AGG | GCT | ATT | GAG | GCG | CAA | CAG | CAT | CTG | 2336 |
| Gln | Gln | Gln | Asn | Asn | Leu | Leu | Arg | Ala | Ile | Glu | Ala | Gln | Gln | His | Leu |
| | | 550 | | | | 555 | | | | | 560 | | | | |
| TTG | CAA | CTC | ACA | GTC | TGG | GGC | ATC | AAG | CAG | CTC | CAG | GCA | AGA | GTC | CTG | 2384 |
| Leu | Gln | Leu | Thr | Val | Trp | Gly | Ile | Lys | Gln | Leu | Gln | Ala | Arg | Val | Leu |
| 565 | | | | | 570 | | | | | 575 | | | | | |
| GCT | GTG | GAA | AGA | TAC | CTA | AGG | GAT | CAA | CAG | CTC | CTG | GGG | ATT | TGG | GGT | 2432 |
| Ala | Val | Glu | Arg | Tyr | Leu | Arg | Asp | Gln | Gln | Leu | Leu | Gly | Ile | Trp | Gly |
| 580 | | | | | 585 | | | | | 590 | | | | | 595 |
| TGC | TCT | GGA | AAA | CTC | ATC | TGC | ACC | ACT | GCT | GTG | CCT | TGG | AAT | GCT | AGT | 2480 |
| Cys | Ser | Gly | Lys | Leu | Ile | Cys | Thr | Thr | Ala | Val | Pro | Trp | Asn | Ala | Ser |
| | | | | 600 | | | | | 605 | | | | | 610 | |
| TGG | AGT | AAT | AAA | TCT | CTG | AAT | AAG | ATT | TGG | GAT | AAC | ATG | ACC | TGG | ATA | 2528 |
| Trp | Ser | Asn | Lys | Ser | Leu | Asn | Lys | Ile | Trp | Asp | Asn | Met | Thr | Trp | Ile |
| | | | 615 | | | | | 620 | | | | | 625 | | |
| GAG | TGG | GAC | AGA | GAA | ATT | AAC | AAT | TAC | ACA | AGC | ATA | ATA | TAC | AGC | TTA | 2576 |
| Glu | Trp | Asp | Arg | Glu | Ile | Asn | Asn | Tyr | Thr | Ser | Ile | Ile | Tyr | Ser | Leu |
| | | 630 | | | | 635 | | | | | 640 | | | | |
| ATT | GAA | GAA | TCG | CAG | AAC | CAA | CAA | GAA | AAG | AAT | GAA | CAA | GAA | TTA | TTA | 2624 |
| Ile | Glu | Glu | Ser | Gln | Asn | Gln | Gln | Glu | Lys | Asn | Glu | Gln | Glu | Leu | Leu |
| | 645 | | | | | 650 | | | | | 655 | | | | |
| GAA | TTA | GAT | AAA | TGG | GCA | AGT | TTG | TGG | AAT | TGG | TTT | GAC | ATA | ACA | AAA | 2672 |
| Glu | Leu | Asp | Lys | Trp | Ala | Ser | Leu | Trp | Asn | Trp | Phe | Asp | Ile | Thr | Lys |
| 660 | | | | | 665 | | | | | 670 | | | | | 675 |
| TGG | CTG | TGG | TAT | ATA | AAA | ATA | TTC | ATA | ATG | ATA | GTA | GGA | GGC | TTG | ATA | 2720 |
| Trp | Leu | Trp | Tyr | Ile | Lys | Ile | Phe | Ile | Met | Ile | Val | Gly | Gly | Leu | Ile |
| | | | 680 | | | | | 685 | | | | | 690 | | |
| GGT | TTA | AGA | ATA | GTT | TTT | TCT | GTA | CTT | TCT | ATA | GTG | AAT | AGA | GTT | AGG | 2768 |
| Gly | Leu | Arg | Ile | Val | Phe | Ser | Val | Leu | Ser | Ile | Val | Asn | Arg | Val | Arg |
| | | | 695 | | | | | 700 | | | | | 705 | | |
| CAG | GGA | TAC | TCA | CCA | TTA | TCG | TTT | CAG | ACC | CAC | CTC | CCA | TCC | TCG | AGG | 2816 |
| Gln | Gly | Tyr | Ser | Pro | Leu | Ser | Phe | Gln | Thr | His | Leu | Pro | Ser | Ser | Arg |
| | | 710 | | | | | 715 | | | | | 720 | | | |
| GGA | CCC | GAC | AGG | CCC | GGA | GGA | ATC | GAA | GAA | GAA | GGT | GGA | GAG | AGA | GAC | 2864 |
| Gly | Pro | Asp | Arg | Pro | Gly | Gly | Ile | Glu | Glu | Glu | Gly | Gly | Glu | Arg | Asp |
| 725 | | | | | 730 | | | | | 735 | | | | | |
| AGA | GAC | AGA | TCC | GGT | CCA | TTA | GTG | AAC | GGA | TTC | TTG | GCG | CTT | ATC | TGG | 2912 |
| Arg | Asp | Arg | Ser | Gly | Pro | Leu | Val | Asn | Gly | Phe | Leu | Ala | Leu | Ile | Trp |
| 740 | | | | | 745 | | | | | 750 | | | | | 755 |
| GTC | GAT | CTG | CGG | AGC | CTG | TTC | CTC | TTC | AGC | TAC | CAC | CGC | TTG | AGA | GAC | 2960 |
| Val | Asp | Leu | Arg | Ser | Leu | Phe | Leu | Phe | Ser | Tyr | His | Arg | Leu | Arg | Asp |
| | | | | 760 | | | | | 765 | | | | | 770 | |
| TTA | CTC | TTG | ATT | GTG | ATG | AGG | ATT | GTG | GAA | CTT | CTG | GGA | CTA | GCA | GGG | 3008 |
| Leu | Leu | Leu | Ile | Val | Met | Arg | Ile | Val | Glu | Leu | Leu | Gly | Leu | Ala | Gly |
| | | | 775 | | | | | 780 | | | | | 785 | | |
| GGG | TGG | GAA | GTC | CTC | AAA | TAT | TGG | TGG | AAT | CTC | CTA | CAG | TAT | TGG | AGT | 3056 |
| Gly | Trp | Glu | Val | Leu | Lys | Tyr | Trp | Trp | Asn | Leu | Leu | Gln | Tyr | Trp | Ser |
| | | 790 | | | | | 795 | | | | | 800 | | | |
| CAG | GAA | CTA | AAG | AAT | AGT | GCT | GTT | AGC | TTG | CTC | AAT | GCC | ACA | GCT | GTA | 3104 |
| Gln | Glu | Leu | Lys | Asn | Ser | Ala | Val | Ser | Leu | Leu | Asn | Ala | Thr | Ala | Val |
| 805 | | | | | 810 | | | | | 815 | | | | | |
| GCA | GTA | GCT | GAA | GGG | ACA | GAT | AGG | GTT | ATA | GAA | GTA | TTA | CAG | AGA | GCT | 3152 |
| Ala | Val | Ala | Glu | Gly | Thr | Asp | Arg | Val | Ile | Glu | Val | Leu | Gln | Arg | Ala |
| 820 | | | | | 825 | | | | | 830 | | | | | 835 |
| GTT | AGA | GCT | ATT | CTC | CAC | ATA | CCT | AGA | AGA | ATA | AGA | CAG | GGC | TTG | GAA | 3200 |
| Val | Arg | Ala | Ile | Leu | His | Ile | Pro | Arg | Arg | Ile | Arg | Gln | Gly | Leu | Glu |
| | | | | 840 | | | | | 845 | | | | | 850 | |
| AGG | GCT | TTG | CTA | TAAGATGGGT | | GGCAAGTGGT | | CAAAAAGTAG | | TATAGTCGTA | | | | | | 3252 |
| Arg | Ala | Leu | Leu |
| | | | 855 |

TGGCCTGCTG TAAGGAAAAG AATGAGAAGA ACTGAGCCAG CAGCAGATGG AGTAGGAGCA 3312

```
GTATCTAGAG ACCTGGAAAA ACATGGAGCA ATCACAAGTA GCAATACAGC AGCTAACAAT    3372

GCTGATTGTG CCTGGCTAGA AGCACAAGAG GATGAAGAAG TGGGTTTTCC AGTCAGACCT    3432

CAGGTACCTT TAAGACCAAT GACTCGCAGT GCAGCTATAG ATCTTAGCCA CTTTTTTAAG    3492

AAAAAGGGGG GACTGGAAGG GCTAATTCAC TCCCAAAAAA GACAAGATAT CCTTGATTTG    3552

TGGGTCTACC ACACACAAGG CTACTTCCCT GATTGGCAGA ACTACACACC AGGGCCAGGG    3612

ACCAGATTTC CACTGACCTT TGGATGGTGC TTCAAGCTAG TACCAGTTGA GCCAGAGAAG    3672

GTAGAAGAGG CCAATGAAGG AGAGAACAAC TGCTTGTCAC ACCCTATGAG CCTGCATGGG    3732

ATGGATGACC CGGAGAAAGA AGTGTTAGCA TGGAAGTTTG ACAGCAGCCT AGCATTCCAT    3792

CACGTGGCCC GAGAA                                                    3807
```

( 2 ) INFORMATION FOR SEQ ID NO:6:

( i ) SEQUENCE CHARACTERISTICS:
        ( A ) LENGTH: 855 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Arg Val Thr Glu Ile Arg Lys Ser Tyr Gln His Trp Trp Arg Trp
 1               5                  10                  15

Gly Ile Met Leu Leu Gly Ile Leu Met Ile Cys Asn Ala Glu Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Arg Lys Ala Tyr Asp Thr Glu Val
        50                  55                  60

His Asn Val Trp Ala Thr His Ala Cys Val Pro Thr Asp Pro Asn Pro
 65                  70                  75                  80

Gln Glu Val Glu Leu Lys Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Leu Arg Asn Ala Thr Asn Gly Asn Asp Thr Asn Thr
130                 135                 140

Thr Ser Ser Ser Arg Gly Met Val Gly Gly Gly Glu Met Lys Asn Cys
145                 150                 155                 160

Ser Phe Asn Ile Thr Thr Asn Ile Arg Gly Lys Val Gln Lys Glu Tyr
                165                 170                 175

Ala Leu Phe Tyr Lys Leu Asp Ile Ala Pro Ile Asp Asn Asn Ser Asn
            180                 185                 190

Asn Arg Tyr Arg Leu Ile Ser Cys Asn Thr Ser Val Ile Thr Gln Ala
        195                 200                 205

Cys Pro Lys Val Ser Phe Glu Pro Ile Pro Ile His Tyr Cys Ala Pro
210                 215                 220

Ala Gly Phe Ala Ile Leu Lys Cys Lys Asp Lys Lys Phe Asn Gly Lys
225                 230                 235                 240

Gly Pro Cys Thr Asn Val Ser Thr Val Gln Cys Thr His Gly Ile Arg
                245                 250                 255

Pro Val Val Ser Thr Gln Leu Leu Leu Asn Gly Ser Leu Ala Glu Glu
            260                 265                 270

Glu Val Val Ile Arg Ser Ala Asn Phe Ala Asp Asn Ala Lys Val Ile
```

|     |     |     |     | 275 |     |     |     |     | 280 |     |     |     |     | 285 |     |     |     |
| --- | --- | --- | --- | --- | --- | --- | --- | --- | --- | --- | --- | --- | --- | --- | --- | --- | --- |
| Ile | Val | Gln | Leu | Asn | Glu | Ser | Val | Glu | Ile | Asn | Cys | Thr | Arg | Pro | Asn |
| 290 |     |     |     |     | 295 |     |     |     |     | 300 |
| Asn | Asn | Thr | Arg | Lys | Ser | Ile | His | Ile | Gly | Pro | Gly | Arg | Ala | Phe | Tyr |
| 305 |     |     |     |     | 310 |     |     |     |     | 315 |     |     |     |     | 320 |
| Thr | Thr | Gly | Glu | Ile | Ile | Gly | Asp | Ile | Arg | Gln | Ala | His | Cys | Asn | Leu |
|     |     |     |     |     | 325 |     |     |     |     | 330 |     |     |     |     | 335 |
| Ser | Arg | Ala | Lys | Trp | Asn | Asp | Thr | Leu | Asn | Lys | Ile | Val | Ile | Lys | Leu |
|     |     |     |     | 340 |     |     |     |     | 345 |     |     |     |     | 350 |
| Arg | Glu | Gln | Phe | Gly | Asn | Lys | Thr | Ile | Val | Phe | Lys | His | Ser | Ser | Gly |
|     |     |     |     | 355 |     |     |     |     | 360 |     |     |     |     | 365 |
| Gly | Asp | Pro | Glu | Ile | Val | Thr | His | Ser | Phe | Asn | Cys | Gly | Gly | Glu | Phe |
|     |     | 370 |     |     |     |     | 375 |     |     |     |     | 380 |
| Phe | Tyr | Cys | Asn | Ser | Thr | Gln | Leu | Phe | Asn | Ser | Thr | Trp | Asn | Val | Thr |
| 385 |     |     |     |     | 390 |     |     |     |     | 395 |     |     |     |     | 400 |
| Glu | Glu | Ser | Asn | Asn | Thr | Val | Glu | Asn | Asn | Thr | Ile | Thr | Leu | Pro | Cys |
|     |     |     |     | 405 |     |     |     |     | 410 |     |     |     |     | 415 |
| Arg | Ile | Lys | Gln | Ile | Ile | Asn | Met | Trp | Gln | Glu | Val | Gly | Arg | Ala | Met |
|     |     |     |     | 420 |     |     |     |     | 425 |     |     |     |     | 430 |
| Tyr | Ala | Pro | Pro | Ile | Arg | Gly | Gln | Ile | Arg | Cys | Ser | Ser | Asn | Ile | Thr |
|     |     |     | 435 |     |     |     |     | 440 |     |     |     |     | 445 |
| Gly | Leu | Leu | Leu | Thr | Arg | Asp | Gly | Gly | Pro | Glu | Asp | Asn | Lys | Thr | Glu |
|     | 450 |     |     |     |     | 455 |     |     |     |     | 460 |
| Val | Phe | Arg | Pro | Gly | Gly | Gly | Asp | Met | Arg | Asp | Asn | Trp | Arg | Ser | Glu |
| 465 |     |     |     |     | 470 |     |     |     |     | 475 |     |     |     |     | 480 |
| Leu | Tyr | Lys | Tyr | Lys | Val | Val | Lys | Ile | Glu | Pro | Leu | Gly | Val | Ala | Pro |
|     |     |     |     | 485 |     |     |     |     | 490 |     |     |     |     | 495 |
| Thr | Lys | Ala | Lys | Arg | Arg | Val | Val | Gln | Arg | Glu | Lys | Arg | Ala | Val | Gly |
|     |     |     |     | 500 |     |     |     |     | 505 |     |     |     |     | 510 |
| Ile | Gly | Ala | Val | Phe | Leu | Gly | Phe | Leu | Gly | Ala | Ala | Gly | Ser | Thr | Met |
|     |     |     | 515 |     |     |     |     | 520 |     |     |     |     | 525 |
| Gly | Ala | Ala | Ala | Met | Thr | Leu | Thr | Val | Gln | Ala | Arg | Leu | Leu | Leu | Ser |
|     | 530 |     |     |     |     | 535 |     |     |     |     | 540 |
| Gly | Ile | Val | Gln | Gln | Gln | Asn | Asn | Leu | Leu | Arg | Ala | Ile | Glu | Ala | Gln |
| 545 |     |     |     |     | 550 |     |     |     |     | 555 |     |     |     |     | 560 |
| Gln | His | Leu | Leu | Gln | Leu | Thr | Val | Trp | Gly | Ile | Lys | Gln | Leu | Gln | Ala |
|     |     |     |     | 565 |     |     |     |     | 570 |     |     |     |     | 575 |
| Arg | Val | Leu | Ala | Val | Glu | Arg | Tyr | Leu | Arg | Asp | Gln | Gln | Leu | Leu | Gly |
|     |     |     |     | 580 |     |     |     |     | 585 |     |     |     |     | 590 |
| Ile | Trp | Gly | Cys | Ser | Gly | Lys | Leu | Ile | Cys | Thr | Thr | Ala | Val | Pro | Trp |
|     |     | 595 |     |     |     |     | 600 |     |     |     |     | 605 |
| Asn | Ala | Ser | Trp | Ser | Asn | Lys | Ser | Leu | Asn | Lys | Ile | Trp | Asp | Asn | Met |
| 610 |     |     |     |     | 615 |     |     |     |     | 620 |
| Thr | Trp | Ile | Glu | Trp | Asp | Arg | Glu | Ile | Asn | Asn | Tyr | Thr | Ser | Ile | Ile |
| 625 |     |     |     |     | 630 |     |     |     |     | 635 |     |     |     |     | 640 |
| Tyr | Ser | Leu | Ile | Glu | Glu | Ser | Gln | Asn | Gln | Gln | Glu | Lys | Asn | Glu | Gln |
|     |     |     |     | 645 |     |     |     |     | 650 |     |     |     |     | 655 |
| Glu | Leu | Leu | Glu | Leu | Asp | Lys | Trp | Ala | Ser | Leu | Trp | Asn | Trp | Phe | Asp |
|     |     |     |     | 660 |     |     |     |     | 665 |     |     |     |     | 670 |
| Ile | Thr | Lys | Trp | Leu | Trp | Tyr | Ile | Lys | Ile | Phe | Ile | Met | Ile | Val | Gly |
|     |     | 675 |     |     |     |     | 680 |     |     |     |     | 685 |
| Gly | Leu | Ile | Gly | Leu | Arg | Ile | Val | Phe | Ser | Val | Leu | Ser | Ile | Val | Asn |
|     | 690 |     |     |     |     | 695 |     |     |     |     | 700 |
| Arg | Val | Arg | Gln | Gly | Tyr | Ser | Pro | Leu | Ser | Phe | Gln | Thr | His | Leu | Pro |
| 705 |     |     |     |     | 710 |     |     |     |     | 715 |     |     |     |     | 720 |

```
Ser  Ser  Arg  Gly  Pro  Asp  Arg  Pro  Gly  Ile  Glu  Glu  Gly  Gly
                    725                 730                 735
Glu  Arg  Asp  Arg  Asp  Arg  Ser  Gly  Pro  Leu  Val  Asn  Gly  Phe  Leu  Ala
               740                 745                      750
Leu  Ile  Trp  Val  Asp  Leu  Arg  Ser  Leu  Phe  Leu  Phe  Ser  Tyr  His  Arg
          755                      760                      765
Leu  Arg  Asp  Leu  Leu  Leu  Ile  Val  Met  Arg  Ile  Val  Glu  Leu  Leu  Gly
     770                      775                 780
Leu  Ala  Gly  Gly  Trp  Glu  Val  Leu  Lys  Tyr  Trp  Trp  Asn  Leu  Leu  Gln
785                      790                 795                           800
Tyr  Trp  Ser  Gln  Glu  Leu  Lys  Asn  Ser  Ala  Val  Ser  Leu  Leu  Asn  Ala
                    805                      810                      815
Thr  Ala  Val  Ala  Val  Ala  Glu  Gly  Thr  Asp  Arg  Val  Ile  Glu  Val  Leu
               820                 825                      830
Gln  Arg  Ala  Val  Arg  Ala  Ile  Leu  His  Ile  Pro  Arg  Arg  Ile  Arg  Gln
          835                      840                      845
Gly  Leu  Glu  Arg  Ala  Leu  Leu
     850                 855
```